(12) United States Patent
Ruben

(10) Patent No.: US 7,189,820 B2
(45) Date of Patent: Mar. 13, 2007

(54) ANTIBODIES AGAINST TUMOR NECROSIS FACTOR DELTA (APRIL)

(75) Inventor: Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 287 days.

(21) Appl. No.: 10/151,882

(22) Filed: May 22, 2002

(65) Prior Publication Data

US 2003/0059862 A1    Mar. 27, 2003

Related U.S. Application Data

(60) Provisional application No. 60/293,100, filed on May 24, 2001.

(51) Int. Cl.
  C12P 21/08    (2006.01)
  C12P 21/04    (2006.01)
  C07K 16/00    (2006.01)
  A61K 39/395   (2006.01)
  C12N 7/01     (2006.01)
  C12N 5/06     (2006.01)

(52) U.S. Cl. .............. 530/387.3; 530/388.1; 530/388.23; 530/391.1; 530/391.3; 530/391.7; 424/133.1; 424/135.1; 424/141.1; 424/145.1; 435/69.6; 435/235.1; 435/328

(58) Field of Classification Search ............ 530/387.3, 530/388.1, 388.23, 391.1, 391.3, 391.7; 424/133.1, 135.1, 141.1, 145.1; 435/69.6, 435/235.1, 328
See application file for complete search history.

(56) References Cited

U.S. PATENT DOCUMENTS

| | | | |
|---|---|---|---|
| 5,487,984 A | 1/1996 | Allet et al. | |
| 5,916,771 A | 6/1999 | Hori et al. | |
| 5,925,548 A | 7/1999 | Beutler et al. | |
| 6,171,787 B1 | 1/2001 | Wiley | |
| 6,297,022 B1 | 10/2001 | McDonnell et al. | |
| 6,297,367 B1 | 10/2001 | Tribouley | |
| 6,440,694 B1 | 8/2002 | Bienkowski et al. | |
| 6,506,882 B2 | 1/2003 | Yu et al. | |
| 6,509,170 B1 | 1/2003 | Yu et al. | |
| 6,541,224 B2 | 4/2003 | Yu et al. | |
| 6,635,482 B1 | 10/2003 | Yu et al. | |
| 2002/0055474 A1 | 5/2002 | Busfield | |
| 2002/0072089 A1 | 6/2002 | Holtzman et al. | |
| 2003/0059937 A1 | 3/2003 | Ruben et al. | |
| 2003/0100074 A1 | 5/2003 | Yu et al. | |
| 2003/0166864 A1 | 9/2003 | Yu et al. | |
| 2003/0175208 A1 | 9/2003 | Yu et al. | |
| 2003/0198640 A1 | 10/2003 | Yu et al. | |
| 2003/0223996 A1 | 12/2003 | Ruben et al. | |

FOREIGN PATENT DOCUMENTS

| | | |
|---|---|---|
| EP | 0 911 633 | 4/1999 |
| EP | 0 919 620 | 8/1999 |
| WO | WO93/16178 | 8/1993 |
| WO | WO97/33902 | 9/1997 |
| WO | WO-98/56906 A1 | 12/1998 |
| WO | WO99/00518 | 1/1999 |
| WO | WO99/11791 | 3/1999 |
| WO | WO99/12965 | 3/1999 |
| WO | WO99/28462 | 6/1999 |
| WO | WO99/33980 | 7/1999 |
| WO | WO99/35170 | 7/1999 |
| WO | WO99/50416 | 10/1999 |
| WO | WO99/54460 | 10/1999 |
| WO | WO99/55858 | 11/1999 |
| WO | WO00/26244 | 5/2000 |
| WO | WO00/32776 | 6/2000 |
| WO | WO00/37640 | 6/2000 |
| WO | WO00/50597 | 8/2000 |
| WO | WO00/55320 | 9/2000 |
| WO | WO 200063699 A1 * | 10/2000 |
| WO | WO00/68378 | 11/2000 |

(Continued)

OTHER PUBLICATIONS

Rudikoff et al. Proc. Natl. Acad. Sci. USA, 79:1979-1983, 1982.*
Coleman P. M. Research in Immunology, 145:33-36, 1994.*
Brown et al. The Journal of Immunology, 156:3285-3291, 1996.*
Gruss et al., "Tumor Necrosis Factor Ligand Superfamily: Involvement in the Pathology of Malignant Lymphomas," Blood 85(12):3378-3404, 1995.
Hahne et al., "APRIL, a New Ligand of the Tumor Necrosis Factor Family, Stimulates Tumor Cell Growth," Journal of Experimental Medicine 188(6):1185-1190, 1998.
Kelly et al., "APRIL/TRDL-1, a tumor necrosis factor-like ligand, stimulates cell death," Cancer Research 60(4):1021-1027, 2000.

(Continued)

*Primary Examiner*—Sheel J. Huff
*Assistant Examiner*—David J. Blanchard
(74) *Attorney, Agent, or Firm*—Human Genome Sciences, Inc.

(57) ABSTRACT

The present invention relates to antibodies and related molecules that immunospecifically bind to Tumor Necrosis Factor Delta (TNF-delta; APRIL). The present invention also relates to methods and compositions for detecting, diagnosing, prognosing, treating, preventing, or ameliorating a disease or disorder associated with aberrant APRIL or APRIL receptor expression or aberrant function of APRIL or APRIL receptor, comprising antibodies or fragments or variants thereof, or related molecules, that immunospecifically bind to APRIL. In particular, the present invention further relates to methods and compositions for detecting, diagnosing, prognosing, preventing, treating or ameliorating autoimmune diseases or disorder, such as systemic lupus erythematosus Rheumatoid arthritis, and Sjögren's syndrome, or cancers of the immune system, particularly B cell cancers such as non-Hodgkin's lymphoma and multiple myeloma, comprising administering to an animal, preferably a human, an effective amount of one or more antibodies or fragments or variants thereof, or related molecules, that immunospecifically bind to APRIL.

52 Claims, 3 Drawing Sheets

FOREIGN PATENT DOCUMENTS

| WO | WO00/77256 | 12/2000 |
| --- | --- | --- |
| WO | WO01/24811 | 4/2001 |
| WO | WO01/25256 | 4/2001 |
| WO | WO01/58949 | 8/2001 |
| WO | WO01/60397 | 8/2001 |
| WO | WO01/077291 | 10/2001 |
| WO | WO01/81417 | 11/2001 |
| WO | WO01/87979 | 11/2001 |
| WO | WO02/038766 | 5/2002 |
| WO | WO02/064829 | 8/2002 |
| WO | WO02/094852 | 11/2002 |
| WO | WO03/014294 | 2/2003 |
| WO | WO03/022877 | 3/2003 |
| WO | WO03/035846 | 5/2003 |
| WO | WO03/040307 | 5/2003 |

OTHER PUBLICATIONS

Marsters et al., "Interaction of the TNF homologues BlyS and APRIL with the TNF receptor homologues BCMA and TACI," Current Biology 10(13):785-788, 2000.

Wu et al., "Tumor Necrosis Factor (TNF) Receptor Superfamily Member TACI is a High Affinity Receptor for TNF Family Members APRIL and BLyS," Journal of Biological Chemistry 275(45):35478-35485, 2000.

Rennert et al., "A Soluble Form of B Cell Maturation Antigen, a Receptor for the Tumor Necrosis Factor Family Member APRIL, Inhibits Tumor Cell Growth," Journal of Experimental Medicine 192(11):1677-1683, 2000.

Ware, C., "APRIL and BAFF Connect Autoimmunity and Cancer," Journal of Experimental Medicine 192(11):F35-F37, 2000.

Yu et al., "APRIL and TALL-1 and receptors BCMA and TACI: system for regulating humoral immunity," Nature Immunology 1(3):252-256, 2000.

Roth et al., "APRIL, a new member of the tumor necrosis factor family, modulates death ligand-induced apoptosis," Cell Death and Differentiation 8:403-410, 2001.

Von Bulow et al., "Regulation of the T-Independent Humoral Response by TACI," Immunity 14:573-582, 2001.

Xu et al., "B-Cell Maturation Protein, Which Binds the Tumor Necrosis Factor Family Members BAFF and APRIL, Is Dispensable for Humoral Immune Responses," Molecular and Cellular Biology 21(12):4067-4074, 2001.

Khare et al., "The role of TALL-1 and APRIL in immune regulation," TRENDS In Immunology 22(2):61-63, 2001.

Laabi et al., "Lymphocyte Survival—Ignorance is BLys," Science 289(5481):883, 2000.

Shu et al., "TALL-1 is a novel member of the TNF family that is down-regulated by mitogens," Journal of Leukocyte Biology 65:680-683, 1999.

Lopez-Fraga et al., "Biologically active APRIL is secreted following intracellular processing in the Golgi apparatus by furin convertase," EMBO Reports 2(10):945-951, 2001.

Roschke et al., "BLyS and APRIL Form Biologically Active Heterotrimers That Are Expressed in Patients with Systemic Immune-Based Rheumatic Diseases," Journal of Immunology 169:4314-4321, 2002.

Pradet-Balade et al., "An endogenous hybrid mRNA encodes TWE-PRIL, a functional cell surface TWEAK-APRIL fusion protein," EMBO Journal, 21(21):5711-5720, 2002.

Litinskiy et al., "DCs induce CD40-independent immunoglobulin class switching through BLyS and APRIL," Nature Immunology 3(9):822-829, Sep. 2002.

Macpherson et al., "BLySsful interactions between DCs and B cells," Nature Immunology 3(9):798-800, Sep. 2002.

Golub, E.S. and Green, D.R., *Immunology: a Synthesis*, $2^{nd}$ edition, Sunderland, MA:Sinauer Associates, Inc., pp. 153-154 (1991).

Deng et al., "Basis for selection of improved carbohydrate-binding single-chain antibodies from synthetic gene libraries," *Proc. Natl. Acad. Sci. USA*, 92:4992-4996 (May 1995).

Barbas et al., "In vitro evolution of a neutralizing human antibody to human immunodeficiency virus type 1 to enhance affinity and broaden strain cross-reactivity," *Proc. Natl. Acad. Sci. USA*, 91:3809-3813 (Apr. 1994).

Deng et al., "Selection of Antibody Single-chain Variable Fragments with Improved Carbohydrate Binding by Phage Display," *J. Biol. Chem.*, 269(13):9533-9538 (Apr. 1, 1994).

Schier et al., "Isolation of Picomolar Affinity Anti-c-erbB-2 Single-chain Fv by Molecular Evolution of the Complementarity Determining Regions in the Center of the Antibody Binding Site," *J. Mol. Biol.*, 263:551-567 (1996).

Seshasyaee et al, "Loss of TACI Causes Fatal Lymphoproliferation and Autoimmunity, Establishing TACI as an Inhibitory BLyS Receptor," *Immunity*, 18:279-288 (2003).

* cited by examiner

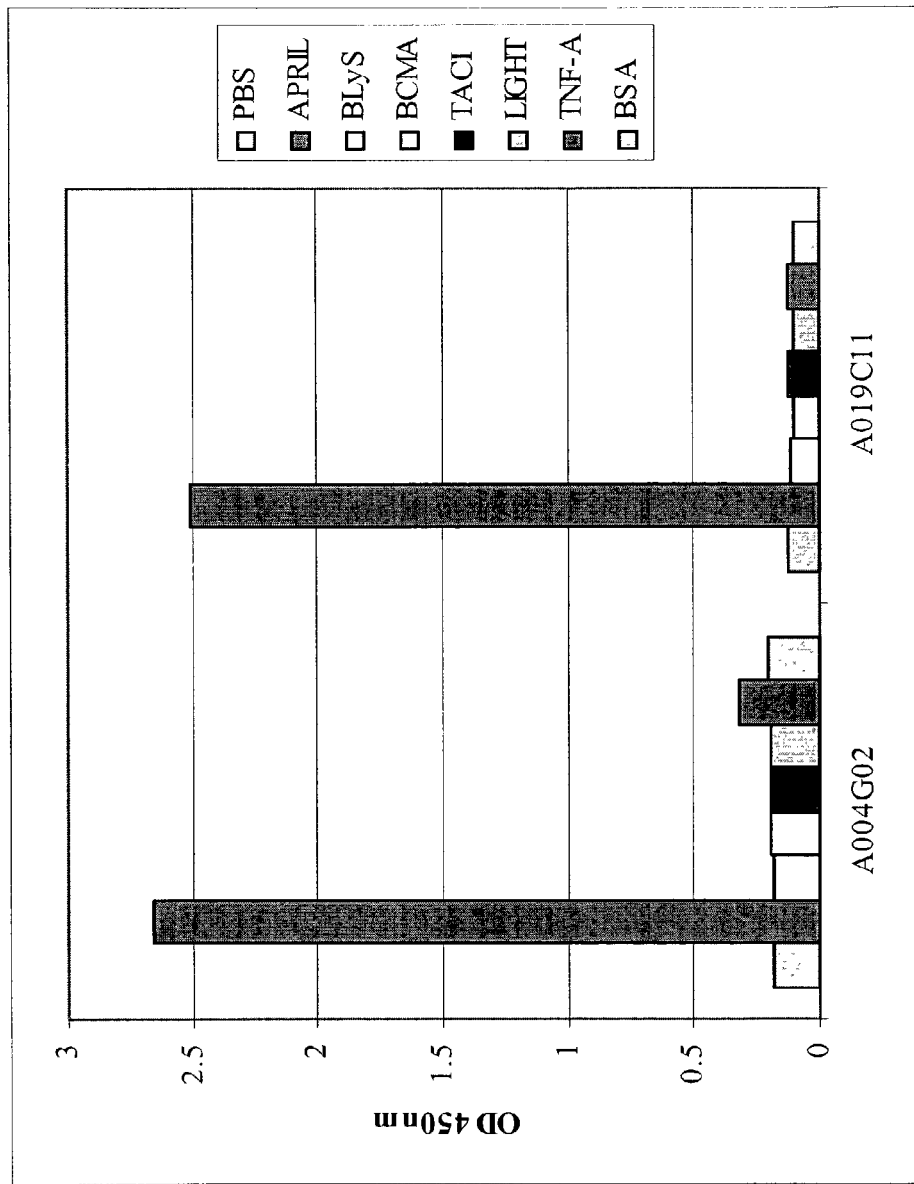

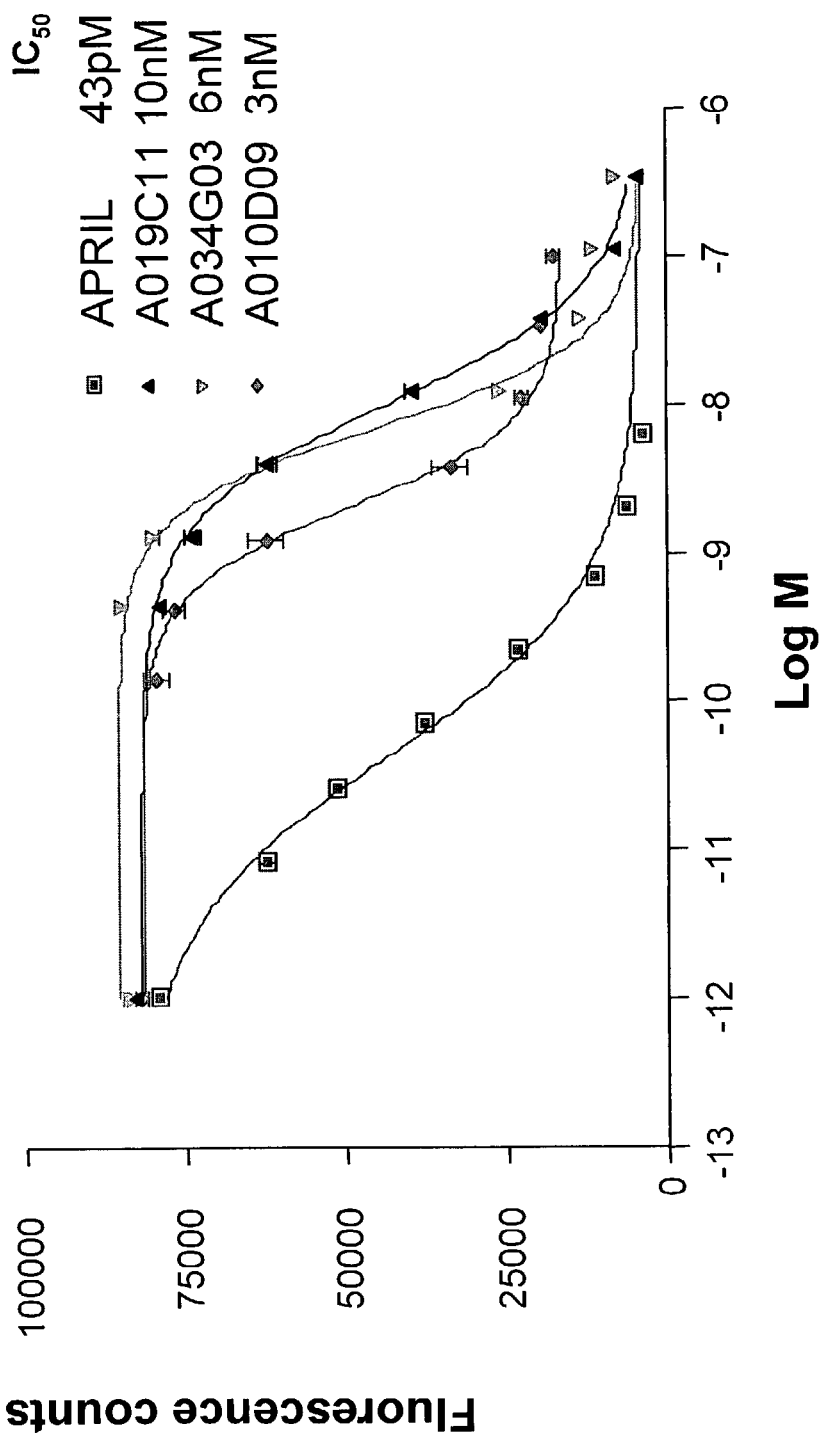

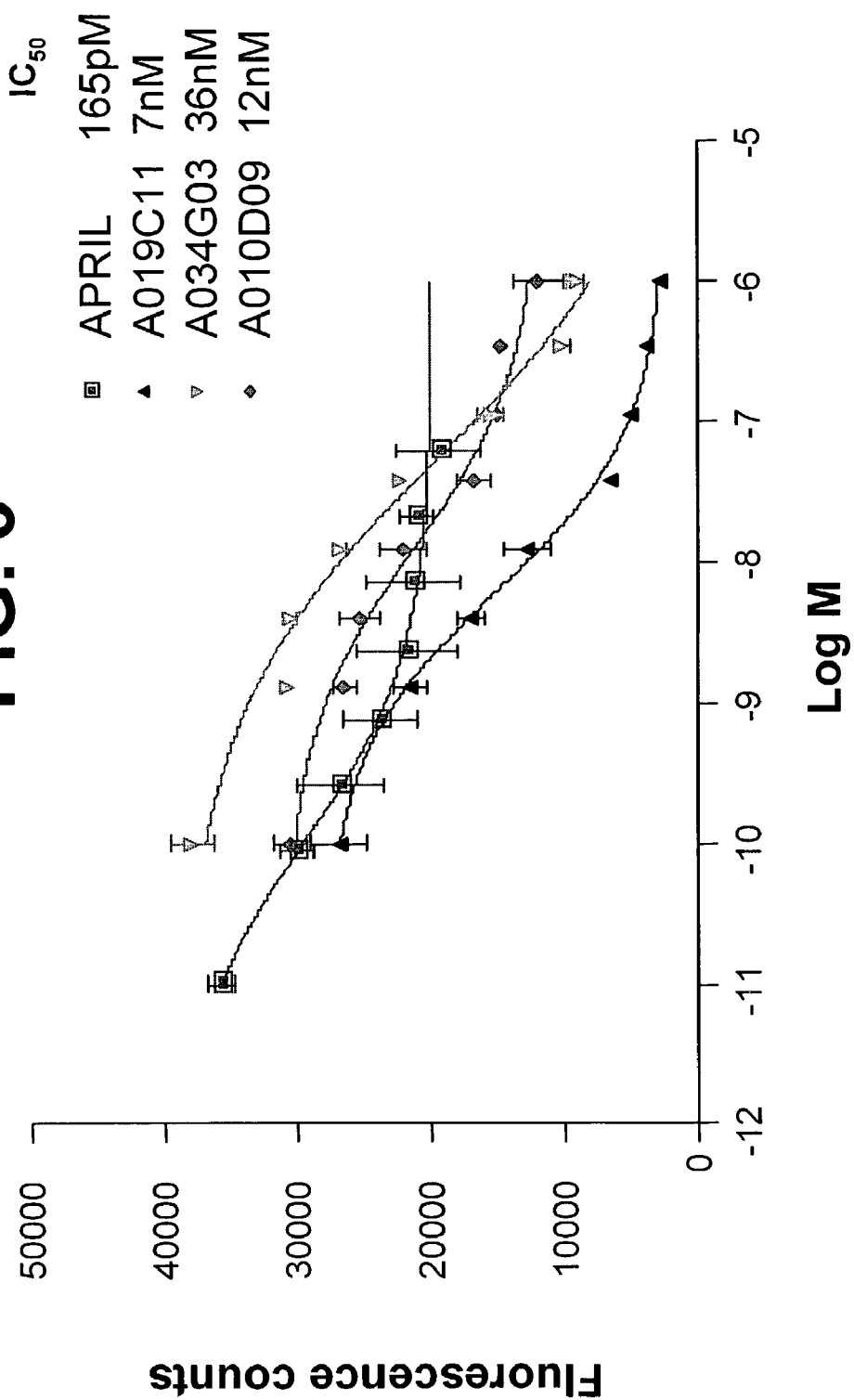

ANTIBODIES AGAINST TUMOR NECROSIS FACTOR DELTA (APRIL)

RELATED APPLICATIONS

This application claims the benefit of priority under 35 U.S.C. § 119(e) based on U.S. Provisional Application Ser. No. 60/293,100 filed May 24, 2001.

INTRODUCTION

The present invention relates to antibodies and related molecules that immunospecifically bind to Tumor Necrosis Factor Delta (TNF-delta; APRIL). The present invention also relates to methods and compositions for detecting, diagnosing, prognosing, treating, preventing, or ameliorating a disease or disorder associated with aberrant APRIL or APRIL receptor expression or aberrant function of APRIL or APRIL receptor, comprising antibodies or fragments or variants thereof, or related molecules, that immunospecifically bind to APRIL. In particular, the present invention further relates to methods and compositions for detecting, diagnosing, prognosing, preventing, treating or ameliorating autoimmune diseases or disorder, such as systemic lupus erythematosus Rheumatoid arthritis, and Sjögren's syndrome, or cancers of the immune system, particularly B cell cancers such as non-Hodgkin's lymphoma and multiple myeloma, comprising administering to an animal, preferably a human, an effective amount of one or more antibodies or fragments or variants thereof, or related molecules, that immunospecifically bind to APRIL.

BACKGROUND OF THE INVENTION

Tumor Necrosis Factor delta (TNF-delta; APRIL) is a member of the tumor necrosis factor ("TNF") superfamily that induces both in vivo and in vitro B cell proliferation and differentiation (See e.g. U.S. Patent Application Nos. 60/016,812; 60/211,537; 60/241,952; 60/254,875; 60/277,978; and Ser. No. 08/815,783 (now U.S. Pat. No. 6,509,170); and International Publication No. WO97/33902; and Yu et al., Nature Immunol. 1(3):252–256 (2000)). APRIL is distinguishable from other B cell growth and differentiation factors such as IL-2, IL-4, IL-5, IL-6, IL-7, IL-13, IL-15, CD40L, or CD27L (CDT0) by its monocyte-specific gene and protein expression pattern and its specific receptor distribution and biological activity on B lymphocytes. APRIL expression is not detected in natural killer ("NK") cells, T cells or B cells, but is restricted to cells of myeloid origin. The gene encoding APRIL has been mapped to chromosome 17p13.

APRIL is expressed as a 250 amino acid type II membrane-bound polypeptide and a soluble 146 amino acid polypeptide (SEQ ID NO:37). The $NH_2$-terminus of the soluble form of APRIL begins at $Ala^{88}$ of SEQ ID NO:36 (which is equivalent to Ala 105 of SEQ ID NO:37). Soluble recombinant APRIL has been shown to induce in vitro proliferation of murine splenic B cells and to bind to a cell-surface receptor on these cells and also on T cells (Yu et al., 2000 supra). Soluble APRIL administration to mice has been shown to result in an increase in B cell numbers in the spleen and mesenteric lymph node, and an increase in serum IgM levels (Yu et al., 2000 supra).

Based upon its expression pattern and biological activity, APRIL has been suggested to be involved in the exchange of signals between B cells, T cells and monocytes or their differentiated progeny. As such, antibodies and related molecules that immunospecifically bind to APRIL may find medical utility in, for example, the treatment of B cell disorders and T cell disorders associated with for example autoimmunity, neoplasia, or immunodeficiency syndromes.

SUMMARY OF THE INVENTION

The present invention encompasses antibodies (including molecules comprising, or alternatively consisting of, antibody fragments or variants thereof) that immunospecifically bind to a polypeptide or polypeptide fragment of APRIL. In particular, the invention encompasses antibodies (including molecules comprising, or alternatively consisting of, antibody fragments or variants thereof) that immunospecifically bind to a polypeptide or polypeptide fragment of human APRIL (e.g., polypeptides encoded by SEQ ID NO:35, polypeptides encoded by the cDNA contained in ATCC Deposit number 97377 deposited Dec. 8, 1995, or the polypeptides of SEQ ID Nos:36 and/or 37) or APRIL expressed on human monocytes.

The present invention also encompasses methods and compositions for detecting, diagnosing, or prognosing diseases or disorders associated with aberrant APRIL or APRIL receptor expression or aberrant function of APRIL or APRIL receptor in an animal, preferably a mammal, and most preferably a human, comprising, or alternatively consisting of, use of antibodies (including molecules comprising, or alternatively consisting of, antibody fragments or variants thereof) that immunospecifically bind to APRIL. Diseases and disorders which can be detected, diagnosed, or prognosed with the antibodies (including molecules comprising, or alternatively consisting of, antibody fragments or variants thereof) of the invention include, but are not limited to, immune disorders (e.g., autoimmune diseases including lupus, rheumatoid arthritis, Sjögren's Syndrome, multiple sclerosis, myasthenia gravis, Hashimoto's disease; immunodeficiency syndrome, and inflammatory disorders such as asthma, allergic disorders, and rheumatoid arthritis), infectious diseases (e.g., AIDS), and proliferative disorders (e.g., leukemia, carcinoma, and lymphoma). The present invention further encompasses methods and compositions for preventing, treating or ameliorating diseases or disorders associated with aberrant APRIL or APRIL receptor expression or aberrant function of APRIL or APRIL receptor in an animal, preferably a mammal, and most preferably a human, comprising, or alternatively consisting of, administering to said animal an effective amount of one or more antibodies (including molecules comprising, or alternatively consisting of, antibody fragments or variants thereof) that immunospecifically bind to APRIL. Diseases and disorders which can be prevented, treated or ameliorated by administering an effective amount of an antibody of the invention include, but are not limited to, immune disorders (e.g., autoimmune diseases including lupus, rheumatoid arthritis, Sjögren's Syndrome, multiple sclerosis, myasthenia gravis, Hashimoto's disease; immunodeficiency syndrome, and inflammatory disorders such as asthma, allergic disorders, and rheumatoid arthritis), infectious diseases (e.g., AIDS), and proliferative disorders (e.g., leukemia, carcinoma, and lymphoma).

Using phage display technology, single chain antibody molecules ("scFvs") that immunospecifically bind to APRIL polypeptides have been identified (Example 1). Molecules comprising, or alternatively consisting of, fragments or variants of these scFvs (e.g., including VH domains, VH CDRs, VL domains, or VL CDRs having an amino acid sequence of any one of those referred to in Table 1), that immunospecifically bind APRIL polypeptides, are also encompassed by the invention, as are nucleic acid molecules that encode these APRIL polypeptide binding scFvs, and/or molecules.

In particular, the invention relates to scFvs comprising, or alternatively consisting of, an amino acid sequence selected from the group consisting of SEQ ID NOs: 13–15, 16–20, and 21–24, and most preferably SEQ ID NOs:13–14, 16, and 21–22, as referred to in Table 1. In specific embodiments, the present invention relates to scFvs that immunospecifically bind APRIL polypeptides and inhibit APRIL binding to both BCMA and TACI, said scFvs comprising, or alternatively consisting of, an amino acid sequence of SEQ ID NOs: 13–15, and most preferably SEQ ID NOs: 13–14, as referred to in Table 1, below. In other embodiments, the present invention also relates to scFvs that immunospecifically bind APRIL polypeptides and inhibit APRIL binding to BCMA while partially inhibiting APRIL binding to TACI, said scFvs comprising, or alternatively consisting of, an amino acid sequence of SEQ ID NOs: 16–20, and most preferably SEQ ID NOs: 16–17, as referred to in Table 1. In further embodiments, the present invention relates to scFvs that immunospecifically bind APRIL polypeptides and partially inhibit APRIL binding to both BCMA and TACI, said scFvs comprising, or alternatively consisting of, an amino acid sequence of SEQ ID NOs: 21–24, and most preferably SEQ ID NOs: 21–22, as referred to in Table 1. In yet further embodiments, the present invention relates to scFvs that immunospecifically bind APRIL polypeptides and do not inhibit APRIL binding to BCMA or TACI. The invention also encompasses molecules comprising, or alternatively consisting of, fragments or variants of these scFvs (e.g., including VH domains, VH CDRs, VL domains, or VL CDRs having an amino acid sequence of any one of those referred to in Table 1), that immunospecifically bind APRIL polypeptides and fully and/or partially inhibit binding of APRIL to BCMA and/or TACI. Also encompassed by the invention, are nucleic acid molecules encoding these APRIL-binding scFvs, and/or molecules, as described, for example, as SEQ ID NOs: 1–12, in Table 1.

The present invention provides antibodies (including molecules comprising, or alternatively consisting of, antibody fragments or variants thereof) that immunospecifically bind to a polypeptide or polypeptide fragment of APRIL, said antibodies comprising, or alternatively consisting of, a polypeptide having the amino acid sequence of any one of the variable heavy ("VH") domains referred to in Table 1, below, or any one of the variable light ("VL") domains referred to in Table 1. In a preferred embodiment, antibodies of the present invention comprise, or alternatively consist of, a polypeptide having the amino acid sequence of a VH domain contained in SEQ ID NOs:13–14, 15–16, 17–20, 21–22 or 23–24, as referred to in Table 1. In another preferred embodiment, antibodies (including molecules comprising or alternatively consisting of, antibody fragments or variants thereof) of the present invention comprise, or alternatively consist of, a polypeptide having the amino acid sequence of a VL domain contained in SEQ ID NOs: 13–14, 15–16, 17–20, 21–22 or 23–24, as referred to in Table 1. The present invention also encompasses molecules comprising, or alternatively consisting of, fragments or variants of these antibodies (e.g., including VH domains, VH CDRs, VL domains, or VL CDRs having an amino acid sequence of any one of those referred to in Table 1), that immunospecifically bind APRIL polypeptides. Also encompassed by the invention, are nucleic acid molecules encoding these APRIL-binding antibodies, and/or molecules, as described, for example, in SEQ ID NOs: 1–12, in Table 1.

The present invention also provides antibodies (including molecules comprising or alternatively consisting of, antibody fragments or variants thereof) that immunospecifically bind to a polypeptide or a polypeptide fragment of APRIL, said antibodies comprising, or alternatively consisting of, a polypeptide having the amino acid sequence of any one of the VH domains referred to in Table 1, below, and any one of the VL domains referred to in Table 1. In a preferred embodiment, the antibodies of the invention comprise or alternatively consist of, a polypeptide having the amino acid sequence of a VH and VL domain contained in the same scFv referred to in Table 1. In another preferred embodiment, antibodies of the present invention, comprise, or alternatively consist of, a VH domain from an scFv contained in any one of SEQ ID NOs:13–14, 15–16, 17–20, 21–22 or 23–24, as disclosed in Table 1, and a VL domain from an scFv contained in any one of SEQ ID NOs:13–14, 15–16, 17–20, 21–22 or 23–24, as disclosed in Table 1. In another preferred embodiment, antibodies of the present invention comprise, or alternatively consist of, the VH and VL domain from a single scFv contained in SEQ ID NOs: 13–14, 15–16, 17–20, 21–22 or 23–24, as disclosed in Table 1. The present invention also encompasses molecules comprising, or alternatively consisting of, fragments or variants of these antibodies (e.g., including VH domains, VH CDRs, VL domains, or VL CDRs having an amino acid sequence of any one of those referred to in Table 1), that immunospecifically bind APRIL polypeptides. Also encompassed by the invention, are nucleic acid molecules encoding these APRIL-binding antibodies, and/or molecules, as described, for example, in SEQ ID NOs: 1–12, in Table 1.

The present invention also provides antibodies (including molecules comprising, or alternatively consisting of, antibody fragments or variants thereof) that immunospecifically bind to a polypeptide or a polypeptide fragment of APRIL, said antibodies comprising, or alternatively consisting of, a polypeptide having the amino acid sequence of any one, two, three or more of the VH complementarity determining regions ("CDRs") (i.e., VH CDR1, VH CDR2, or VH CDR3) referred to in Table 1 and/or any one, two, three or more of the VL CDRs (i.e., VL CDR1, VL CDR2, or VL CDR3) referred to in Table 1. In one embodiment, antibodies of the present invention comprise, or alternatively consist of, a polypeptide having the amino acid sequence of any one of the VH CDR1s referred to in Table 1 and/or any one of the VL CDR1s referred to in Table 1. In another embodiment, antibodies of the present invention comprise, or alternatively consist of, a polypeptide having the amino acid sequence of any one of the VH CDR2s referred to in Table 1 and/or any one of the VL CDR2s referred to in Table 1. In a preferred embodiment, antibodies of the present invention comprise, or alternatively consist of, a polypeptide having the amino acid sequence of any one of the VH CDR3s referred to in Table 1 and/or any one of the VL CDR3s referred to in Table 1. The present invention also encompasses molecules comprising, or alternatively consisting of, fragments or variants of these antibodies (e.g., including VH domains, VH CDRs, VL domains, or VL CDRs having an amino acid sequence of any one of those referred to in Table 1), that immunospecifically bind APRIL polypeptides. Also encompassed by the invention, are nucleic acid molecules encoding these APRIL-binding antibodies, and/or molecules, as described, for example, in SEQ ID NOs: 1–12, in Table 1.

In another embodiment, antibodies of the present invention (including molecules comprising, or alternatively consisting of, antibody fragments or variants thereof) immunospecifically bind to a polypeptide or polypeptide fragment of APRIL, and comprise, or alternatively consist of, a polypeptide having the amino acid sequence of any one of the VH CDR1s referred to in Table 1, any one of the VH CDR2s referred to in Table 1, and/or any one of the VH CDR3s referred to in Table 1. In another embodiment, antibodies of the present invention comprise, or alternatively consist of, a polypeptide having the amino acid sequence of any one of the VL CDR1s referred to in Table 1, any one of the VL CDR2s referred to in Table 1, and/or any one of the VL CDR3s referred to in Table 1. In a preferred embodiment, antibodies of the present invention comprise, or alternatively consist of, at least one, two, three, four, five, six, or more CDRs that correspond to the same scFv referred to in Table 1, more preferably where CDR1, CDR2, and CDR3 of the VL domain correspond to the same scFv or where CDR1, CDR2, and CDR3 of the VH domain correspond to the same scFv, and most preferably where all six CDRs correspond to the same scFv referred to in Table 1. The present invention also encompasses molecules comprising, or alternatively consisting of, fragments or variants of these antibodies (e.g., including VH domains, VH CDRs, VL domains, or VL CDRs having an amino acid sequence of any one of those referred to in Table 1), that immunospecifically bind APRIL polypeptides. Also encompassed by the invention, are nucleic acid molecules encoding these APRIL-binding antibodies, and/or molecules, as described, for example, in SEQ ID NOs: 1–12, in Table 1.

The present invention also provides antibodies (including molecules comprising, or alternatively consisting of, antibody fragments or variants thereof) that: immunospecifically bind to a soluble form of APRIL (e.g., a polypeptide consisting of amino acids 88–233 of SEQ ID NO:36); that immunospecifically bind to a membrane-bound form of APRIL (e.g., a polypeptide consisting of amino acids 1–233 of SEQ ID NO:36, 1–250 of SEQ ID NO:37 or an APRIL polypeptide expressed on the surface of monocytes) and/or that immunospecifically bind to both soluble and membrane-bound forms of APRIL. In a preferred embodiment, antibodies of the present invention immunospecifically bind to a soluble form of APRIL and comprise, or alternatively consist of, a VH domain, VH CDR1, VH CDR2, VH CDR3, VL domain, VL CDR1, VL CDR2, and/or VL CDR3 of one or more scFvs that immunospecifically bind to a soluble form of APRIL. In another preferred embodiment, antibodies of the present invention immunospecifically bind to a membrane-bound form of APRIL and comprise, or alternatively consist of, a VH domain, VH CDR1, VH CDR2, VH CDR3, VL domain, VL CDR1, VL CDR2, and/or VL CDR3 of one or more scFvs that immunospecifically bind to a membrane-bound form of APRIL. In yet another preferred embodiment, antibodies of the present invention immunospecifically bind to soluble and membrane-bound forms of APRIL and comprise, or alternatively consist of, a VH domain, VH CDR1, VH CDR2, VH CDR3, VL domain, VL CDR1, VL CDR2, and/or VL CDR3 of one or more scFvs that immunospecifically binds to soluble and membrane-bound forms of APRIL. In another preferred embodiment, antibodies of the present invention comprise, or alternatively consist of, a VH domain and a VL domain of the same scFv disclosed in Table 1, which antibodies immunospecifically bind to a soluble form of APRIL, a membrane-bound form of APRIL, or both soluble and membrane-bound forms of APRIL. Also encompassed by the present invention are nucleic acid molecules encoding these antibodies, including, for example, the polynucleotide sequences contained in SEQ ID NOs: 1–12, as described in Table 1. Molecules comprising, or alternatively consisting of, fragments or variants of these antibodies (e.g., including VH domains, VH CDRs, VL domains, or VL CDRs having an amino acid sequence of any one of those referred to in Table 1), that immunospecifically bind a soluble form of APRIL, a membrane-bound form of APRIL, or both soluble and membrane-bound forms of APRIL, are also encompassed by the invention. Also encompassed by the invention are nucleic acid molecules that encode these antibodies, and/or molecules, including the polynucleotide sequences SEQ ID NOs: 1–12, as described in Table 1.

A VH domain of an amino acid sequence disclosed herein may be combined with a VL domain of an amino acid sequence disclosed herein, or other VL domains, to provide a VH/VL pairing representing an antigen-binding site of an antibody. Similarly, a VL domain of an amino acid sequence disclosed herein may be combined with a VH domain of an amino acid sequence disclosed herein, or other VH domains. Further, one or more CDRs disclosed herein may be taken from a VH or VL domain and incorporated into a suitable framework as discussed infra.

The present invention provides antibodies (including molecules comprising, or alternatively consisting of, antibody fragments or variants thereof (including derivatives)) comprising, or alternatively consisting of, of VH domains, VL domains and/or CDRs described herein, which antibodies, immunospecifically bind to APRIL (e.g., soluble APRIL and membrane-bound APRIL) and can be routinely assayed for immunospecific binding to APRIL using methods known in the art, such as, for example, the immunoassays disclosed infra. Antibodies and antibody fragments or variants (including derivatives) of the invention may include, for example, one or more amino acid sequence alterations (addition, deletion, substitution and/or insertion of an amino acid residue). These alterations may be made in one or more framework regions and/or one or more CDR's. The antibodies of the invention (including antibody fragments, and variants and derivative thereof) can be routinely made by methods known in the art. Molecules comprising, or alternatively consisting of, fragments or variants of any of the VH domains, VH CDRs, VL domains, and VL CDRs whose sequences are specifically disclosed herein may be employed in accordance with the present invention. Nucleic acid molecules encoding these antibodies and molecules (including fragments, variants, and derivatives), as described, for example, in SEQ ID NOs: 1–12, in Table 1, are also encompassed by the invention.

The present invention also provides panels of antibodies (including molecules comprising, or alternatively consisting of, antibody fragments or variants) wherein the panel members correspond to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), antiidiotypic (anti-Id) antibodies, and scFvs). The present invention further provides mixtures of antibodies, wherein the mixture corresponds to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), antiidiotypic (anti-Id) antibodies, and scFvs). The present invention also provides for compositions comprising, or alternatively consisting of, one, two, three, four, five, ten, fifteen, twenty, or more antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more antibodies or fragments or variants thereof. Alternatively, a composition of the invention may comprise, or alternatively consist of, nucleic acid molecules encoding one or more antibodies of the invention, as described, for example, in SEQ ID NOs: 1–12, in Table 1.

The present invention also provides for fusion proteins comprising an antibody (including molecules comprising, or alternatively consisting of, antibody fragments or variants thereof) of the invention, and a heterologous polypeptide (i.e., a polypeptide unrelated to an antibody or antibody domain). Nucleic acid molecules encoding these fusion proteins are also encompassed by the invention. A composition of the present invention may comprise, or alternatively consist of, one, two, three, four, five, ten, fifteen, twenty or more fusion proteins of the invention. Alternatively, a composition of the invention may comprise, or alternatively consist of, nucleic acid molecules encoding one, two, three, four, five, ten, fifteen, twenty or more fusion proteins of the invention.

The present invention also provides for a nucleic acid molecule, generally isolated, encoding an antibody (including molecules such as scFvs, which comprise, or alternatively consist of, an antibody fragment or variant thereof) of the invention, as described, for example, in SEQ ID NOs: 1–12, in Table 1. The present invention also provides a host cell transformed with a nucleic acid molecule of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

The present invention also encompasses methods and compositions for detecting, diagnosing and/or prognosing diseases or disorders associated with aberrant APRIL or APRIL receptor expression or aberrant APRIL or APRIL receptor function in an animal, preferably a mammal, and most preferably a human, comprising using antibodies (including molecules which comprise, or alternatively consist of, antibody fragments or variants thereof) that immunospecifically bind to APRIL. Diseases and disorders which can be detected, diagnosed or prognosed with the antibodies of the invention include, but are not limited to, immune disorders (e.g., autoimmune diseases including lupus, rheumatoid arthritis, Sjögren's Syndrome, multiple sclerosis, myasthenia gravis, Hashimoto's disease; immunodeficiency syndrome, and inflammatory disorders such as asthma, allergic disorders, and rheumatoid arthritis), infectious diseases (e.g., AIDS), and proliferative disorders (e.g., leukemia, carcinoma, and lymphoma).

In specific embodiments, the present invention encompasses methods and compositions for detecting, diagnosing and/or prognosing diseases or disorders associated with hypergammaglobulinemia (e.g., AIDS, autoimmune diseases, and some immunodeficiencies). In other specific embodiments, the present invention encompasses methods and compositions for detecting, diagnosing and/or prognosing diseases or disorders associated with hypogammaglobulinemia (e.g., an immunodeficiency).

The present invention further encompasses methods and compositions for preventing, treating or ameliorating diseases or disorders associated with aberrant APRIL or APRIL receptor expression or aberrant APRIL or APRIL receptor function in an animal, preferably a mammal, and most preferably a human, comprising administering to said animal an effective amount of one or more antibodies (including molecules which comprise, or alternatively consist of, antibody fragments or variants thereof) that immunospecifically bind to APRIL. Diseases and disorders which can be prevented, treated or inhibited by administering an effective amount of one or more antibodies or molecules of the invention include, but are not limited to, immune disorders (e.g., autoimmune diseases including lupus, rheumatoid arthritis, Sjögren's Syndrome, multiple sclerosis, myasthenia gravis, Hashimoto's disease; immunodeficiency syndrome, and inflammatory disorders such as asthma, allergic disorders, and rheumatoid arthritis), infectious diseases (e.g., AIDS), and proliferative disorders (e.g., leukemia, carcinoma, and lymphoma).

In specific embodiments, the present invention encompasses methods and compositions (e.g., antagonistic anti-APRIL antibodies) for preventing, treating or ameliorating diseases or disorders associated with hypergammaglobulinemia (e.g., AIDS, autoimmune diseases, and some immunodeficiency syndromes). In other specific embodiments, the present invention encompasses methods and compositions (e.g., agonistic anti-APRIL antibodies) for preventing, treating or ameliorating diseases or disorders associated with hypogammaglobulinemia (e.g., an immunodeficiency syndrome).

Autoimmune and inflammatory disorders, diseases, or conditions that may be detected, diagnosed, prognosed, or monitored using the antibodies of the invention include, but are not limited to, autoimmune hemolytic anemia (including, but not limited to cryoglobinemia or Coombs positive anemia), autoimmune neonatal thrombocytopenia, idiopathic thrombocytopenic purpura, autoimmune thrombocytopenic purpura, autoimmune neutropenia, autoimmunocytopenia, hemolytic anemia, antiphospholipid syndrome, dermatitis (e.g. atopic dermatitis), gluten-sensitive enteropathy, allergic encephalomyelitis, myocarditis, relapsing polychondritis, rheumatic heart disease, glomerulonephritis (e.g., primary glomerulonephritis and IgA nephropathy), Multiple Sclerosis, Neuritis, Uveitis Ophthalmia, Polyendocrinopathies, Purpura (e.g., Henloch-Schoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, diabetes mellitus (e.g. Type I diabetes mellitus or insulin dependent diabetes mellitus), juvenile onset diabetes, autoimmune inflammatory eye, autoimmune thyroiditis, hypothyroidism (i.e., Hashimoto's thyroiditis), systemic lupus erythematosus, discoid lupus, Goodpasture's syndrome, Pemphigus, Receptor autoimmunities such as, for example, (a) Graves' Disease , (b) Myasthenia Gravis, and (c) insulin resistance, rheumatoid arthritis, scleroderma with anti-collagen antibodies, mixed connective tissue disease, polymyositis/dermatomyositis, pernicious anemia (Addison's disease), idiopathic Addison's disease, infertility, bullous pemphigoid, Sjögren's syndrome, adrenergic drug resistance (including adrenergic drug resistance with asthma or cystic fibrosis), chronic active hepatitis, primary biliary cirrhosis, other endocrine gland failure, vitiligo, vasculitis, post-MI cardiotomy syndrome, urticaria, asthma, inflammatory myopathies, and other inflammatory, granulomatous, degenerative, and atrophic disorders, and other disorders such as inflammatory skin diseases including psoriasis and sclerosis, responses associated with inflammatory bowel disease (such as Crohn's disease and ulcerative colitis), respiratory distress syndrome (including adult respiratory distress syndrome, ARDS), meningitis, encephalitis, colitis, allergic conditions such as eczema and other conditions involving infiltration of T cells and chronic inflammatory responses, atherosclerosis, leukocyte adhesion deficiency, Reynaud's syndrome, and immune responses associated with acute and delayed hypersensitivity mediated by cytokines and T-lymphocytes typically found in tuberculosis, sarcoidosis, granulomatosis and diseases involving leukocyte diapedesis, central nervous system (CNS) inflammatory disorder, multiple organ injury syndrome, antigen-antibody complex mediated diseases, anti-glomerular basement membrane disease, Lambert-Eaton myasthenic syndrome, Becket's disease, giant cell arteritis, immune complex nephritis, IgM polyneuropathies or autoimmune thrombocytopenia etc.

Immunodeficiencies that may be detected, diagnosed, prognosed, or monitored using the antibodies of the invention include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

BRIEF DESCRIPTION OF THE DRAWINGS

FIG. 1. ELISA results for two scFvs, A004G02 and A019C11, that immunospecifically bind to APRIL, but do not bind to or cross-react with BLyS, BCMA, TACI, LIGHT, or TNF-alpha or BSA.

FIG. 2. The results for three scFvs, A019C11, A034G03 and A010D09, in an assay to measure the ability of the antibodies of the invention to inhibit APRIL binding to BCMA.

FIG. 3. The results for three scFvs, A019C11, A034G03 and A010D09, in an assay to measure the ability of the antibodies of the invention to inhibit APRIL binding to TACI.

DEFINITIONS

The term "antibody," as used herein, refers to immunoglobulin molecules and immunologically active portions of immunoglobulin molecules, i.e., molecules that contain an antigen-binding site that immunospecifically binds an antigen. As such, the term antibody encompasses not only whole antibody molecules, but also antibody fragments as well as variants (including derivatives) of antibodies and antibody fragments. Examples of molecules which are described by the term "antibody" in this application include, but are not limited to: single chain Fvs (scFvs), Fab fragments, Fab' fragments, F(ab')$_2$, disulfide linked Fvs (sdFvs), Fvs, and fragments comprising or alternatively consisting of, either a VL or a VH domain. The term "single chain Fv" or "scFv" as used herein refers to a polypeptide comprising a VL domain of antibody linked to a VH domain of an antibody. Antibodies that immunospecifically bind to APRIL may have cross-reactivity with other antigens. Preferably, antibodies that immunospecifically bind to APRIL do not cross-react with other antigens. Antibodies that immunospecifically bind to APRIL can be identified, for example, by immunoassays or other techniques known to those of skill in the art, e.g., the immunoassays described in the Examples below.

Antibodies of the invention include, but are not limited to, monoclonal, multispecific, human or chimeric antibodies, single chain antibodies, Fab fragments, F(ab') fragments, antiidiotypic (anti-Id) antibodies (including, e.g., anti-Id antibodies to antibodies of the invention), and epitope-binding fragments of any of the above. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule.

Preferably, an antibody of the invention comprises, or alternatively consists of, a VH domain, VH CDR, VL domain, or VL CDR having an amino acid sequence of any one of those referred to in Table 1, or a fragment or variant thereof.

The term "variant" as used herein refers to a polypeptide that possesses a similar or identical function as an antibody (including molecules comprising, or alternatively consisting of, antibody fragments or variants thereof) that immunospecifically binds to a polypeptide or polypeptide fragment of APRIL, but does not necessarily comprise a similar or identical amino acid sequence as an anti-APRIL antibody or antibody fragment thereof, or possess a similar or identical structure as an anti-APRIL antibody or antibody fragment thereof. A variant having a similar amino acid refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of an anti-APRIL antibody or antibody fragment thereof (including a VH domain, VHCDR, VL domain, or VLCDR) having an amino acid sequence of any one of those referred to in Table 1 described herein; (b) a polypeptide encoded by a nucleotide sequence, the complementary sequence of which hybridizes under stringent conditions to a nucleotide sequence encoding an antibody (including molecules comprising, or alternatively consisting of, antibody fragments or variants thereof) that immunospecifically binds to a polypeptide or polypeptide fragment of APRIL (e.g., SEQ ID NOs:1–12); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, identical to the nucleotide sequence encoding an anti-APRIL antibody or antibody fragment thereof (including a VH domain, VHCDR, VL domain, or VLCDR) having an amino acid sequence of any one of those referred to in Table 1, described herein. A polypeptide with similar structure to an anti-APRIL antibody or antibody fragment thereof, described herein refers to a polypeptide that has a similar secondary, tertiary or quarternary structure of an anti-APRIL antibody, or antibody fragment thereof, described herein. The structure of a polypeptide can be determined by methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity=number of identical overlapping positions/ total number of positions×100%). In one embodiment, the two sequences are the same length.

The determination of percent identity between two sequences can be accomplished using a mathematical algorithm known to those of skill in the art. An example of a mathematical algorithm for comparing two sequences is the algorithm of Karlin and Altschul *Proc. Natl. Acad. Sci. USA* 87:2264–2268(1990), modified as in Karlin and Altschul *Proc. Natl. Acad. Sci. USA* 90:5873–5877(1993). The BLASTn and BLASTx programs of Altschul, et al. *J. Mol. Biol.* 215:403–410(1990) have incorporated such an algorithm. BLAST nucleotide searches can be performed with the BLASTn program, score=100, wordlength=12 to obtain nucleotide sequences homologous to a nucleic acid molecules of the invention. BLAST protein searches can be performed with the BLASTx program, score=50, wordlength=3 to obtain amino acid sequences homologous to a protein molecules of the invention. To obtain gapped alignments for comparison purposes, Gapped BLAST can be utilized as described in Altschul et al. *Nucleic Acids Res.* 25:3389–3402(1997). Alternatively, PSI-BLAST can be used to perform an iterated search which detects distant relationships between molecules (Id.). When utilizing BLAST, Gapped BLAST, and PSI-BLAST programs, the default parameters of the respective programs (e.g., BLASTx and BLASTn) can be used. (See the National Center for Biotechnology Information website which is maintained by the United States National Library of Medicine)

Another example of a mathematical algorithm utilized for the comparison of sequences is the algorithm of Myers and Miller, CABIOS (1989). The ALIGN program (version 2.0) which is part of the GCG sequence alignment software package has incorporated such an algorithm. Other algorithms for sequence analysis known in the art include ADVANCE and ADAM as described in Torellis and Robotti *Comput. Appl. Biosci.*, 10:3–5(1994); and FASTA described in Pearson and Lipman *Proc. Natl. Acad. Sci.* 85:2444–8 (1988). Within FASTA, ktup is a control option that sets the sensitivity and speed of the search.

The term "derivative" as used herein, refers to a variant polypeptide of the invention that comprises, or alternatively consists of, an antibody of the invention that immunospecifically binds to APRIL, or a fragment or variant thereof, which has been altered by the introduction of amino acid residue substitutions, deletions or additions. The term "derivative" as used herein also refers to an antibody of the invention, that immunospecifically binds to APRIL, or a fragment or variant thereof, which has been modified, e.g., by the covalent attachment of any type of molecule to the polypeptide. For example, but not by way of limitation, an anti-APRIL antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of an anti-APRIL antibody, may be modified by chemical modifications using techniques known to those of skill in the art, including, but not limited to, specific chemical cleavage, acetylation, formylation, metabolic synthesis of tunicamycin, etc. Further, a derivative of an anti-APRIL antibody, may contain one or more non-classical amino acids. A polypeptide derivative possesses a similar or identical function as an anti-APRIL antibody, or fragment or variant thereof, described herein.

The term "epitopes" as used herein refers to portions of APRIL having antigenic or immunogenic activity in an animal, preferably a mammal. An epitope having immunogenic activity is a portion of APRIL that elicits an antibody response in an animal. An epitope having antigenic activity is a portion of APRIL to which an antibody immunospecifically binds as determined by any method known in the art, for example, by the immunoassays described herein. Antigenic epitopes need not necessarily be immunogenic.

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues, of the amino acid sequence of APRIL, or an anti-APRIL antibody (including molecules such as scFv's, that comprise, or alternatively consist of, antibody fragments or variants thereof) that immunospecifically binds to APRIL.

The term "fusion protein" as used herein refers to a polypeptide that comprises, or alternatively consists of, an amino acid sequence of an anti-APRIL antibody of the invention and an amino acid sequence of a heterologous polypeptide (i.e., a polypeptide unrelated to an antibody or antibody domain).

The term "host cell" as used herein refers to the particular subject cell transfected with a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

DETAILED DESCRIPTION OF THE INVENTION

The present invention encompasses antibodies (including molecules comprising, or alternatively consisting of, antibody fragments or variants thereof) that immunospecifically bind to APRIL or a fragment of APRIL. In particular, the invention provides antibodies such as, for example, single chain Fvs (scFvs) having an amino acid sequence of any one of SEQ ID NOs:13–24, as referred to in Table 1. In particular, the present invention encompasses antibodies that immunospecifically bind to a polypeptide, a polypeptide fragment, or an epitope of human APRIL (e.g., polypeptides encoded by SEQ ID NO:35, polypeptides encoded by the cDNA contained in ATCC Deposit number 97377 deposited Dec. 8, 1995, or the polypeptides of SEQ ID NOs:36, and/or 37) or APRIL expressed on human monocytes (as determined by immunoassays known in the art for assaying specific antibody-antigen binding).

The antibodies of the invention may bind APRIL polypeptides wherein said polypeptides are monomers or multimers (i.e., dimers, trimers, tetramers and higher multimers). Accordingly, the present invention relates to antibodies that bind monomers and multimers of the APRIL polypeptides of the invention, their preparation, and compositions (preferably, pharmaceutical compositions) containing them. In specific embodiments, the APRIL polypeptides bound by the antibodies of the invention are monomers, dimers, trimers or tetramers. In additional embodiments, the polypeptides bound by the antibodies of the invention of the invention are at least dimers, at least trimers, or at least tetramers.

APRIL multimers bound by the antibodies of the invention may be the result of hydrophobic, hydrophilic, ionic and/or covalent associations and/or may be indirectly linked, by for example, liposome formation. Thus, in one embodiment, APRIL multimers, such as, for example, homodimers or homotrimers, are formed when polypeptides of the invention contact one another in solution. In another embodiment, APRIL heteromultimers, such as, for example, APRIL heterotrimers or APRIL heterotetramers, are formed when polypeptides of the invention contact antibodies to the polypeptides of the invention (including antibodies to the heterologous polypeptide sequence in a fusion protein of the invention) in solution. In other embodiments, APRIL multimers are formed by covalent associations with and/or between the APRIL polypeptides of the invention. Such covalent associations may involve one or more amino acid residues contained in the polypeptide sequence (e.g., that recited in SEQ ID NO:36 or SEQ ID NO:37). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in an APRIL fusion protein. In one example, covalent associations are between the heterologous sequence contained in a fusion protein (see, e.g., U.S. Pat. No. 5,478,925). In a specific example, the covalent associations are between the heterologous sequence contained in an APRIL-Fc fusion protein. In another specific example, covalent associations of fusion proteins of the invention are between the heterologous polypeptide sequence from another TNF family ligand/receptor member that is capable of forming covalently associated multimers, such as for example, oseteoprotegerin (see, e.g., International Publication No. WO 98/49305, the contents of which are herein incorporated by reference in their entirety). In another specific example, covalent associations of fusion proteins of the invention are between heterologous polypeptide sequence from CD40L, or a soluble fragment thereof. In another embodiment, two or more APRIL polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple APRIL polypeptides separated by peptide linkers may be produced using conventional recombinant DNA technology.

Antibodies of the invention may bind APRIL polypeptides where said polypeptides are monomers or multimers (i.e., dimers, trimers, tetramers and higher multimers). Accordingly, the present invention relates to antibodies that bind monomers and multimers of the APRIL polypeptides of the invention, their preparation, and compositions (preferably, pharmaceutical compositions) containing them. In specific embodiments, the antibodies of the invention bind APRIL polypeptides where said polypeptides are monomers, dimers, trimers or tetramers. In additional embodiments, the antibodies of the invention bind APRIL polypeptides where said polypeptides are at least dimers, at least trimers, or at least tetramers.

Antibodies of the invention may bind multimeric APRIL polypeptides where said polypeptides are homomers. An APRIL homomer refers to a multimer containing only APRIL polypeptides (including APRIL fragments, variants, and fusion proteins, as described herein). These homomers may contain APRIL polypeptides having identical or different amino acid sequences, e.g., as contained in SEQ ID NOs:36 and 37. In specific embodiments, the antibodies of the invention bind an APRIL multimer where said multimer is a homodimer (e.g., containing two APRIL polypeptides having identical or different amino acid sequences) or a homotrimer (e.g., containing three APRIL polypeptides having identical or different amino acid sequences). In a preferred embodiment, the antibodies of the invention bind homotrimers of APRIL. In additional embodiments, the antibodies of the invention bind a homomeric APRIL multimer where said multimer is at least a homodimer, at least a homotrimer, or at least a homotetramer.

Antibodies of the invention may bind multimeric APRIL polypeptides where said polypeptides are heteromers. Heteromeric APRIL refers to a multimer containing heterologous polypeptides (i.e., polypeptides of a different protein) in addition to APRIL polypeptides having identical or different amino acid sequences, as contained in SEQ ID NO:36 and SEQ ID NO:37. In a specific embodiment, the antibodies of the invention bind an APRIL multimer where said multimer is a heterodimer, a heterotrimer, or a heterotetramer, containing APRIL polypeptides having identical or different amino acid sequences. In additional embodiments, the antibodies of the invention bind a heteromeric APRIL multimer where said multimer is at least a heterodimer, at least a heterotrimer, or at least a heterotetramer. In highly preferred embodiments, the antibodies of the invention bind a heteromeric APRIL multimer where said multimers is a heterotrimer comprising both APRIL polypeptides, (having identical or different amino acid sequences, e.g., as contained in SEQ ID NOs: 36 and 37), and BLyS polypeptides (SEQ ID NO:38, GenBank Accession No. AF132600; Moore et al, Science 285(5425):260–263 (1999)). In one highly preferred embodiment, the antibodies of the invention bind a heteromeric APRIL multimer where said multimer is a heterotrimer comprising one APRIL polypeptide and two BLyS polypeptides. In another highly preferred embodiment, the antibodies of the invention bind a heteromeric APRIL multimer where said multimer is a heterotrimer comprising two APRIL polypeptides and one BLyS polypeptide. In other preferred embodiments, antibodies of the invention bind APRIL/BLyS heteromers comprising at least one APRIL polypeptide and at least one BLyS polypeptide. In a further nonexclusive embodiment, the antibodies of the invention bind APRIL heteromers where said heteromers contain CD40 ligand polypeptide sequence(s), or biologically active fragment(s) or variant(s) thereof.

Antibodies that bind APRIL polypeptides may bind them as isolated polypeptides or in their naturally occurring state. For, example antibodies of the present invention may bind recombinantly produced APRIL polypeptides. In a specific embodiment, antibodies of the present invention bind an APRIL polypeptide purified from a cell culture wherein the cells in said cell culture comprise a polynucleotide encoding amino acids 1 to 250 of SEQ ID NO:37. In alternative embodiments antibodies of the present invention may bind APRIL/BLyS heteromers, particularly, APRIL/BLyS heterotrimers, heterotrimers purified from a cell culture wherein the cells in said cell culture comprise a polynucleotide encoding amino acids 1 to 250 of SEQ ID NO:37 and 1–285 of SEQ ID NO:38 operably associated with a regulatory sequence that controls gene expression.

The antibodies of the invention, in binding APRIL polypeptides, whether they exist as monomers, homomultimers (i.e., homodimers, homotrimers, homotetramers and higher homomultimers), or heteromultimers (i.e., heterodimers, heterotrimers, heterotetramers and higher heteromultimers), may regulate interaction of APRIL monomers, homomultimers, and/or heteromultimers with their receptors. In specific embodiments, the antibodies of the invention inhibit binding of APRIL to BCMA (GenBank Accession Nos. AX087843 and NP_001183; International Publication Nos. WO 01/12812 and WO 01/24811). In further specific embodiments, the antibodies of the invention inhibit binding of APRIL to TACI (GenBank Accession Nos. AF023614 and AAC51790; International Publication Nos. WO WO98/39361 and WO00/58362, each of which are hereby incorporated in their entireties). In further specific embodiments, the antibodies of the invention inhibit binding of APRIL to both BCMA and TACI. In yet further specific embodiments, the antibodies of the invention inhibit binding of APRIL to BCMA and partially inhibit APRIL binding to TACI. In yet further specific embodiments, the antibodies of the invention inhibit binding of APRIL to TACI and partially inhibit APRIL binding to BCMA. In yet further specific embodiments, the antibodies of the invention inhibit binding of APRIL to BCMA but do not inhibit APRIL binding to TACI. In yet further specific embodiments, the antibodies of the invention inhibit binding of APRIL to TACI but do not inhibit APRIL binding to BCMA. In yet further specific embodiments, the antibodies of the invention do not inhibit binding of APRIL to BCMA or TACI. Exemplary assays for assessing the ability of an antibody of the invention to inhibit APRIL binding to BCMA and/or TACI are described in Example 2.

In other specific embodiments, the antibodies of the invention partially inhibit binding of APRIL to BCMA. In further specific embodiments, the antibodies of the invention partially inhibit binding of APRIL to TACI. In further specific embodiments, the antibodies of the invention partially inhibit binding of APRIL to both BCMA and TACI. In yet further specific embodiments, the antibodies of the invention partially inhibit binding of APRIL to BCMA but do not inhibit APRIL binding to TACI. In yet further specific embodiments, the antibodies of the invention partially inhibit binding of APRIL to TACI but do not inhibit APRIL binding to BCMA. In further specific embodiments, the antibodies of the invention do not inhibit binding of APRIL to BCMA or TACI.

The present invention also encompasses antibodies (including molecules comprising, or alternatively consisting of, antibody fragments or variants thereof) that immunospecifically bind to APRIL polypeptides, which antibodies comprise, or alternatively consist of, all or a portion of a heavy and/or light chain variable domain of the scFvs referred to in Table 1.

The present invention also encompasses methods and compositions for detecting, diagnosing and/or prognosing diseases or disorders associated with aberrant APRIL or APRIL receptor expression or aberrant APRIL or APRIL receptor function in an animal, preferably a mammal, and most preferably a human, comprising using antibodies (including molecules which comprise, or alternatively consist of, antibody fragments or variants thereof) that immunospecifically bind to APRIL. Diseases and disorders which can be detected, diagnosed or prognosed with the antibodies of the invention include, but are not limited to, immune disorders (e.g., autoimmune diseases including lupus, rheumatoid arthritis, Sjögren's Syndrome, multiple sclerosis, myasthenia gravis, Hashimoto's disease; immunodeficiency syndrome, and inflammatory disorders such as asthma, allergic disorders, and rheumatoid arthritis), infectious diseases (e.g., AIDS), and proliferative disorders (e.g., leukemia, carcinoma, and lymphoma).

The present invention further encompasses methods and compositions for preventing, treating or ameliorating diseases or disorders associated with aberrant APRIL or APRIL receptor expression or aberrant APRIL or APRIL receptor function in an animal, preferably a mammal, and most preferably a human, comprising administering to said animal an effective amount of one or more antibodies (including molecules which comprise, or alternatively consist of, antibody fragments or variants thereof) that immunospecifically bind to APRIL. Diseases and disorders which can be prevented, treated or inhibited by administering an effective amount of one or more antibodies or molecules of the invention include, but are not limited to, immune disorders (e.g., autoimmune diseases including lupus, rheumatoid arthritis, Sjögren's Syndrome, multiple sclerosis, myasthenia gravis, Hashimoto's disease; immunodeficiency syndrome, and inflammatory disorders such as asthma, allergic disorders, and rheumatoid arthritis), infectious diseases (e.g., AIDS), and proliferative disorders (e.g., leukemia, carcinoma, and lymphoma).

Anti-APRIL Antibodies

The antibodies of the present invention were discovered, in part, using phage display technology. Single chain antibody molecules ("scFvs") displayed on the surface of phage particles were screened to identify those scFvs that immunospecifically bind to APRIL polypeptides. The present invention encompasses the scFvs and portions thereof that were identified to immunospecifically bind to APRIL polypeptides, including fragments and variants thereof. In particular, the present invention encompasses scFvs comprising, or alternatively consisting of, an amino acid sequence of SEQ ID NOs: 13–24, as referred to in Table 1. Preferably, the scFvs of the present invention comprise, or alternatively consist of, an amino acid sequence of SEQ ID NOs:13, 16, 21, or 22. The scFvs include scFvs that bind APRIL polypeptides and inhibit APRIL binding to BCMA and to TACI (e.g., scFvs comprising, or alternatively consisting of, an amino acid sequence of SEQ ID NOs: 13–15), scFvs that bind to APRIL polypeptides and inhibit APRIL binding to BCMA and partially inhibit APRIL binding to TACI (e.g., scFvs comprising, or alternatively consisting of, an amino acid sequence of SEQ ID NOs: 16–20), scFvs that bind to APRIL polypeptides and partially inhibit binding of APRIL to BCMA and to TACI (e.g., scFvs comprising, or alternatively consisting of, an amino acid sequence of SEQ ID NOs: 21–24), and scFvs that bind to APRIL polypeptides and do not inhibit APRIL binding to BCMA or TACI.

invention comprise the amino acid sequence of a VH CDR and VL CDR from the same scFv referred to in Table 1. In alternative embodiments, scFvs of the present invention comprise the amino acid sequence of a VH CDR and VL CDR from different scFvs referred to in Table 1. Molecules comprising, or alternatively consisting of, antibody fragments or variants of the scFvs referred to in Table 1 that immunospecifically bind to APRIL are also encompassed by the invention. The present invention further encompasses nucleic acid molecules encoding these scFvs, molecules, fragments and/or variants, as described, for example, in Table 1.

TABLE 1 scFvs that Immunospecifically Bind to APRIL

| Clone ID | scFv nt SEQ ID NO | scFv AA SEQ ID NO | AAs of VL | AAs of VL CDR1 | AAs VL CDR2 | AAs of VL CDR3 | AAs of VH | AAs of VH CDR1 | AAs of VH CDR2 | AAs of VH CDR3 | VHCDR3 Sequence | VHCDR3 SEQ ID NO: |
|---|---|---|---|---|---|---|---|---|---|---|---|---|
| A019C11 | 1 | 13 | 142–252 | 164–176 | 192–198 | 231–241 | 1–125 | 26–35 | 50–66 | 99–114 | GGRLAGSTVFTPAFEY | 25 |
| A013B07 | 2 | 14 | 142–252 | 164–176 | 192–198 | 231–241 | 1–125 | 26–35 | 50–66 | 99–114 | GGRLAGSTVFTPAFEY | 25 |
| A020F03 | 1 | 13 | 142–252 | 164–176 | 192–198 | 231–241 | 1–125 | 26–35 | 50–66 | 99–114 | GGRLAGSTVFTPAFEY | 25 |
| A004G02 | 3 | 15 | 135–245 | 157–169 | 185–191 | 224–234 | 1–119 | 26–35 | 50–66 | 99–108 | SNPQYDAFDI | 26 |
| A027A11 | 4 | 16 | 132–242 | 154–167 | 183–189 | 222–231 | 1–116 | 26–35 | 50–66 | 99–105 | GSQAFEI | 27 |
| A034G03 | 5 | 17 | 136–248 | 158–171 | 187–193 | 226–237 | 1–119 | 26–35 | 50–66 | 99–108 | GNTGPRPFDP | 28 |
| A034H05 | 6 | 18 | 139–249 | 161–173 | 189–195 | 228–238 | 1–122 | 26–35 | 50–66 | 99–111 | SGGDGYRDYGMDL | 29 |
| A053H04 | 7 | 19 | 136–248 | 158–171 | 187–193 | 226–237 | 1–119 | 26–35 | 50–66 | 99–108 | GNTGPRPFDP | 28 |
| A030D09 | 8 | 20 | 142–250 | 164–174 | 190–196 | 229–239 | 1–127 | 26–35 | 50–66 | 99–116 | SWYYDILTGYWDYYY | 30 |
| A010D09 | 9 | 21 | 134–241 | 157–167 | 183–189 | 222–230 | 1–118 | 26–35 | 50–66 | 99–107 | DLSRLGMDV | 31 |
| A027B01 | 10 | 22 | 133–240 | 156–166 | 182–188 | 221–229 | 1–117 | 26–35 | 50–66 | 99–106 | GISAGMDV | 32 |
| A027H08 | 11 | 23 | 132–239 | 155–165 | 181–187 | 220–228 | 1–117 | 26–35 | 50–66 | 99–106 | GISGGMDV | 33 |
| A024G01 | 12 | 24 | 148–254 | 170–180 | 196–202 | 235–243 | 1–131 | 26–35 | 50–66 | 99–120 | VSRTSYYDVLTDNNRYSYYMDV | 34 |

Molecules comprising, or alternatively consisting of, fragments or variants of these scFvs, that immunospecifically bind to APRIL are also encompassed by the invention, as are nucleic acid molecules encoding these scFvs, molecules, fragments and/or variants, as recited, for example, as SEQ ID NOs:1–12 in Table 1.

In one embodiment of the present invention, scFvs that immunospecifically bind to APRIL comprise a polypeptide having the amino acid sequence of any one of the VH domains referred to in Table 1 and/or any one of the VL domains referred to in Table 1. In preferred embodiments, scFvs of the present invention comprise the amino acid sequence of a VH domain and VL domain from the same scFv referred to in Table 1. In alternative embodiments, scFvs of the present invention comprise the amino acid sequence of a VH domain and VL domain from different scFvs referred to in Table 1. In another embodiment, scFvs that immunospecifically bind to APRIL, comprise a polypeptide having the amino acid sequence of any one, two, three, or more of the VH CDRs referred to in Table 1 and/or any one, two, three, or more of the VL CDRs referred to in Table 1. In preferred embodiments, scFvs of the present In another embodiment of the present invention, an scFv that immunospecifically binds to APRIL polypeptides, inhibiting binding of APRIL to both BCMA and TACI, comprises, or alternatively consists of, an amino acid sequence of SEQ ID NOs:13–15 as referred to in Table 1. In a preferred embodiment, an scFv that immunospecifically binds to APRIL polypeptides, inhibiting binding of APRIL to both BCMA and TACI, comprises, or alternatively consists of, the amino acid sequence of SEQ ID NO:15. In an even more preferred embodiment, an scFv that immunospecifically binds to APRIL polypeptides, inhibiting binding of APRIL to both BCMA and TACI, comprises, or alternatively consists of, the amino acid sequence of SEQ ID NO:14. In a most preferred embodiment, an scFv that immunospecifically binds to APRIL polypeptides, inhibiting binding of APRIL to both BCMA and TACI, comprises, or alternatively consists of, the amino acid sequence of SEQ ID NO:13. Molecules comprising, or alternatively consisting of, fragments or variants of these scFvs, that immunospecifically bind to APRIL polypeptides, inhibiting APRIL binding to BCMA and TACI, are also encompassed by the invention. Also encompassed by the invention are nucleic acid molecules encoding these scFvs, molecules, fragments and/or variants, for example, SEQ ID NOs:1–3 referred to in Table 1.

In another embodiment of the present invention, an scFv that immunospecifically binds APRIL polypeptides, inhibiting APRIL binding to BCMA and partially inhibiting APRIL binding to TACI, comprises, or alternatively consists of, an amino acid sequence of SEQ ID NOs:16–20 as referred to in Table 1. In a preferred embodiment, an scFv that immunospecifically binds APRIL polypeptides, inhibiting APRIL binding to BCMA while partially inhibiting APRIL binding to TACI, comprises, or alternatively consists of, an amino acid sequence of SEQ ID NOs:17–20. In an even more preferred embodiment, an scFv that immunospecifically binds APRIL polypeptides, inhibiting APRIL binding to BCMA while partially inhibiting APRIL binding to TACI, comprises, or alternatively consists of, the amino acid sequence of SEQ ID NO:16. Molecules comprising, or alternatively consisting of, fragments or variants of these scFvs, that immunospecifically bind to APRIL polypeptides, inhibiting APRIL binding to BCMA and partially inhibiting APRIL binding to TACI, are also encompassed by the invention. Also encompassed by the invention are nucleic acid molecules encoding these scFvs, molecules, fragments and/or variants, for example, SEQ ID NOs:4–8 referred to in Table 1.

In another embodiment of the present invention, an scFv that immunospecifically binds APRIL polypeptides, partially inhibiting binding of APRIL to both BCMA and TACI, comprises, or alternatively consists of, an amino acid sequence of SEQ ID NOs:21–24 as referred to in Table 1. In a preferred embodiment, an scFv that immunospecifically binds APRIL polypeptides, partially inhibiting binding of APRIL to both BCMA and TACI, comprises, or alternatively consists of, an amino acid sequence of SEQ ID NOs:23–24. In a most preferred embodiment, an scFv that immunospecifically binds APRIL polypeptides, partially inhibiting binding of APRIL to both BCMA and TACI, comprises, or alternatively consists of, an amino acid sequence of SEQ ID NOs:21–22. Molecules comprising, or alternatively consisting of, fragments or variants of these scFvs, that immunospecifically bind to APRIL polypeptides, partially inhibiting APRIL binding to BCMA and TACI, are also encompassed by the invention. Also encompassed by the invention are nucleic acid molecules encoding these scFvs, molecules, fragments and/or variants, for example, SEQ ID NOs:9–12 referred to in Table 1.

In another embodiment of the present invention, an scFv that immunospecifically binds APRIL polypeptides, without inhibiting binding of APRIL to BCMA or TACI, comprises, or alternatively consists of, an amino acid sequence of SEQ ID NOs:13–24 as referred to in Table 1. Molecules comprising, or alternatively consisting of, fragments or variants of these scFvs, that immunospecifically bind to APRIL polypeptides, without inhibiting APRIL binding to BCMA or TACI, are also encompassed by the invention. Also encompassed by the invention are nucleic acid molecules encoding these scFvs, molecules, fragments and/or variants, for example, SEQ ID NOs:1–12 referred to in Table 1.

In another embodiment of the present invention, scFvs that immunospecifically bind APRIL polypeptides, inhibiting APRIL binding to both BCMA and TACI, comprise a polypeptide having the amino acid sequence of any one of the VH domains contained in SEQ ID NOs:13–15 as disclosed in Table 1 and/or any one of the VL domains contained in SEQ ID NOs:13–15 as disclosed in Table 1. In preferred embodiments, scFvs that immunospecifically bind APRIL polypeptides, inhibiting APRIL binding to both BCMA and TACI, comprise a polypeptide having the amino acid sequence of a VH domain and a VL domain from the same scFv referred to in Table 1. In alternative embodiments, scFvs that immunospecifically bind APRIL polypeptides, inhibiting APRIL binding to both BCMA and TACI, comprise a polypeptide having amino acid sequence of a VH domain and VL domain from different scFvs referred to in Table 1.

In another embodiment of the present invention, scFvs that immunospecifically bind APRIL polypeptides, inhibiting APRIL binding to both BCMA and TACI, comprise a polypeptide having the amino acid sequence of any one of the VH CDRs contained in SEQ ID NOs:13–15 as disclosed in Table 1 and/or any one of the VL CDRs contained in SEQ ID NOs:13–15 as disclosed in Table 1. In preferred embodiments, scFvs that immunospecifically bind APRIL polypeptides, inhibiting APRIL binding to both BCMA and TACI, comprise a polypeptide having the amino acid sequence of a VH-CDR and a VL CDR from the same scFv referred to in Table 1. In alternative embodiments, scFvs that immunospecifically bind APRIL polypeptides, inhibiting APRIL binding to both BCMA and TACI, comprise a polypeptide having amino acid sequence of a VH CDR and VL CDR from different scFvs referred to in Table 1. In another embodiment, scFvs that immunospecifically bind APRIL polypeptides, inhibiting APRIL binding to both BCMA and TACI, comprise a polypeptide having the amino acid sequence of any one, two, three, or more of the VH CDRs contained in SEQ ID NOs:13–15 as disclosed in Table 1 and/or any one, two, three, or more of the VL CDRs contained in contained SEQ ID NOs:13–15, as disclosed in Table 1. In a preferred embodiment, scFvs that immunospecifically bind APRIL polypeptides, inhibiting APRIL binding to both BCMA and TACI, comprise a polypeptide having the amino acid sequence of any one of the VH CDR3s contained in SEQ ID NOs:13–15 as disclosed in Table 1 and/or any one of the VL CDR3s contained in SEQ ID NOs:13–15 as disclosed in Table 1. In preferred embodiments, scFvs that immunospecifically bind APRIL polypeptides, inhibiting APRIL binding to both BCMA and TACI, comprise a polypeptide having the amino acid sequence of a VH CDR3 and VL CDR3 from the same scFv referred to in Table 1. In alternative embodiments, scFvs that immunospecifically bind APRIL polypeptides, inhibiting APRIL binding to both BCMA and TACI, comprise a polypeptide having the of the amino acid sequence of a VH CDR3 and VL CDR3 from different scFvs referred to in Table 1. Molecules comprising, or alternatively consisting of, fragments or variants of these scFvs, that immunospecifically bind to APRIL polypeptides, inhibiting APRIL binding to BCMA and TACI, are also encompassed by the invention, as are nucleic acid molecules encoding these scFvs, molecules, fragments and/or variants, as described, for example, in Table 1.

In another embodiment of the present invention, scFvs that immunospecifically bind APRIL polypeptides, inhibiting APRIL binding to BCMA and partially inhibiting APRIL binding to TACI, comprise a polypeptide having the amino acid sequence of any one of the VH domains contained in SEQ ID NOs:16–20 as disclosed in Table 1 and/or any one of the VL domains contained in SEQ ID NOs:16–20 as disclosed in Table 1. In preferred embodiments, scFvs that immunospecifically bind APRIL polypeptides, inhibiting APRIL binding to BCMA and partially inhibiting APRIL binding to TACI, comprise a polypeptide having the amino acid sequence of a VH domain and a VL domain from the same scFv referred to in Table 1. In alternative embodiments, scFvs that immunospecifically bind APRIL polypeptides, inhibiting APRIL binding to BCMA and partially inhibiting APRIL binding to TACI, comprise a polypeptide having the amino acid sequence of a VH domain and VL domain from different scFvs referred to in Table 1.

In another embodiment of the present invention, scFvs that immunospecifically bind APRIL polypeptides, inhibiting APRIL binding to BCMA and partially inhibiting APRIL binding to TACI, comprise a polypeptide having the amino acid sequence of any one of the VH CDRs contained in SEQ ID NOs:16–20 as disclosed in Table 1 and/or any one of the VL CDRs contained in SEQ ID NOs:16–20 as disclosed in Table 1. In preferred embodiments, scFvs that immunospecifically bind APRIL polypeptides, inhibiting APRIL binding to BCMA and partially inhibiting APRIL binding to TACI, comprise a polypeptide having the amino acid sequence of a VH CDR and a VL CDR from the same scFv referred to in Table 1. In alternative embodiments, scFvs that immunospecifically bind APRIL polypeptides, inhibiting APRIL binding to BCMA and partially inhibiting APRIL binding to TACI, comprise a polypeptide having amino acid sequence of a VH CDR and VL CDR from different scFvs referred to in Table 1. In another embodiment, scFvs that immunospecifically bind APRIL polypeptides, inhibiting APRIL binding to BCMA and partially inhibiting APRIL binding to TACI, comprise a polypeptide having the amino acid sequence of any one, two, three, or more of the VH CDRs contained in SEQ ID NOs:16–20 as disclosed in Table 1 and/or any one, two, three, or more of the VL CDRs contained in contained SEQ ID NOs:16–20, as disclosed in Table 1. In a preferred embodiment, scFvs that immunospecifically bind APRIL polypeptides, inhibiting APRIL binding to BCMA and partially inhibiting APRIL binding to TACI, comprise a polypeptide having the amino acid sequence of any one of the VH CDR3s contained in SEQ ID NOs:16–20 as disclosed in Table 1 and/or any one of the VL CDR3s contained in SEQ ID NOs: 16–20 as disclosed in Table 1. In preferred embodiments, scFvs that immunospecifically bind APRIL polypeptides, inhibiting APRIL binding to BCMA and partially inhibiting APRIL binding to TACI, comprise a polypeptide having the amino acid sequence of a VH CDR3 and VL CDR3 from the same scFv referred to in Table 1. In alternative embodiments, scFvs that immunospecifically bind APRIL polypeptides, inhibiting APRIL binding to BCMA and partially inhibiting APRIL binding to TACI, comprise a polypeptide having the of the amino acid sequence of a VH CDR3 and VL CDR3 from different scFvs referred to in Table 1. Molecules comprising, or alternatively consisting of, fragments or variants of these scFvs, that immunospecifically bind to APRIL polypeptides, inhibiting APRIL binding to BCMA and partially inhibiting APRIL binding to TACI, are also encompassed by the invention, as are nucleic acid molecules encoding these scFvs, molecules, fragments and/or variants, as described, for example, in Table 1.

In another embodiment of the present invention, scFvs that immunospecifically bind APRIL polypeptides, partially inhibiting APRIL binding to both BCMA and TACI, comprise a polypeptide having the amino acid sequence of any one of the VH domains contained in SEQ ID NOs:21–24 as disclosed in Table 1 and/or any one of the VL domains contained in SEQ ID NOs:21–24 as disclosed in Table 1. In preferred embodiments, scFvs that immunospecifically bind APRIL polypeptides, partially inhibiting APRIL binding to both BCMA and TACI, comprise a polypeptide having the amino acid sequence of a VH domain and a VL domain from the same scFv referred to in Table 1. In alternative embodiments, scFvs that immunospecifically bind APRIL polypeptides, partially inhibiting APRIL binding to both BCMA and TACI, comprise a polypeptide having amino acid sequence of a VH domain and VL domain from different scFvs referred to in Table 1.

In another embodiment of the present invention, scFvs that immunospecifically bind APRIL polypeptides, partially inhibiting APRIL binding to both BCMA and TACI, comprise a polypeptide having the amino acid sequence of any one of the VH CDRs contained in SEQ ID NOs:21–24 as disclosed in Table 1 and/or any one of the VL CDRs contained in SEQ ID NOs:21–24 as disclosed in Table 1. In preferred embodiments, scFvs that immunospecifically bind APRIL polypeptides, partially inhibiting APRIL binding to both BCMA and TACI, comprise a polypeptide having the amino acid sequence of a VH CDR and a VL CDR from the same scFv referred to in Table 1. In alternative embodiments, scFvs that immunospecifically bind APRIL polypeptides, partially inhibiting APRIL binding to both BCMA and TACI, comprise a polypeptide having amino acid sequence of a VH CDR and VL CDR from different scFvs referred to in Table 1. In another embodiment, scFvs that immunospecifically bind APRIL polypeptides, partially inhibiting APRIL binding to both BCMA and TACI, comprise a polypeptide having the amino acid sequence of any one, two, three, or more of the VH CDRs contained in SEQ ID NOs:21–24 as disclosed in Table 1 and/or any one, two, three, or more of the VL CDRs contained in contained SEQ ID NOs:21–24, as disclosed in Table 1. In a preferred embodiment, scFvs that immunospecifically bind APRIL polypeptides, partially inhibiting APRIL binding to both BCMA and TACI, comprise a polypeptide having the amino acid sequence of any one of the VH CDR3s contained in SEQ ID NOs:21–24 as disclosed in Table 1 and/or any one of the VL CDR3s contained in SEQ ID NOs: 21–24 as disclosed in Table 1. In preferred embodiments, scFvs that immunospecifically bind APRIL polypeptides, partially inhibiting APRIL binding to both BCMA and TACI, comprise a polypeptide having the amino acid sequence of a VH CDR3 and VL CDR3 from the same scFv referred to in Table 1. In alternative embodiments, scFvs that immunospecifically bind APRIL polypeptides, partially inhibiting APRIL binding to both BCMA and TACI, comprise a polypeptide having the of the amino acid sequence of a VH CDR3 and VL CDR3 from different scFvs referred to in Table 1. Molecules comprising, or alternatively consisting of, fragments or variants of these scFvs, that immunospecifically bind to APRIL polypeptides, partially inhibiting APRIL binding to BCMA and TACI, are also encompassed by the invention, as are nucleic acid molecules encoding these scFvs, molecules, fragments and/or variants, as described, for example, in Table 1.

In another embodiment of the present invention, scFvs that immunospecifically bind APRIL polypeptides, without inhibiting APRIL binding to BCMA or TACI, comprise a polypeptide having the amino acid sequence of any one of the VH domains contained in SEQ ID NOs:13–24 as disclosed in Table 1 and/or any one of the VL domains contained in SEQ ID NOs:13–24 as disclosed in Table 1. In preferred embodiments, scFvs that immunospecifically bind APRIL polypeptides, without inhibiting APRIL binding to BCMA or TACI, comprise a polypeptide having the amino acid sequence of a VH domain and a VL domain from the same scFv referred to in Table 1. In alternative embodiments, scFvs that immunospecifically bind APRIL polypeptides, without inhibiting APRIL binding to BCMA or TACI, comprise a polypeptide having amino acid sequence of a VH domain and VL domain from different scFvs referred to in Table 1.

In another embodiment of the present invention, scFvs that immunospecifically bind APRIL polypeptides, without inhibiting APRIL binding to BCMA or TACI, comprise a polypeptide having the amino acid sequence of any one of the VH CDRs contained in SEQ ID NOs:13–24 as disclosed in Table 1 and/or any one of the VL CDRs contained in SEQ ID NOs:13–24 as disclosed in Table 1. In preferred embodiments, scFvs that immunospecifically bind APRIL polypeptides, without inhibiting APRIL binding to BCMA or TACI, comprise a polypeptide having the amino acid sequence of a VH CDR and a VL CDR from the same scFv referred to in Table 1. In alternative embodiments, scFvs that immunospecifically bind APRIL polypeptides, without inhibiting APRIL binding to BCMA or TACI, comprise a polypeptide having amino acid sequence of a VH CDR and VL CDR from different scFvs referred to in Table 1. In another embodiment, scFvs that immunospecifically bind APRIL polypeptides, without inhibiting APRIL binding to BCMA or TACI, comprise a polypeptide having the amino acid sequence of any one, two, three, or more of the VH CDRs contained in SEQ ID NOs:13–24 as disclosed in Table 1 and/or any one, two, three, or more of the VL CDRs contained in contained SEQ ID NOs:13–24, as disclosed in Table 1. In a preferred embodiment, scFvs that immunospecifically bind APRIL polypeptides, without inhibiting APRIL binding to BCMA or TACI, comprise a polypeptide having the amino acid sequence of any one of the VH CDR3s contained in SEQ ID NOs:13–24 as disclosed in Table 1 and/or any one of the VL CDR3s contained in SEQ ID NOs:13–24 as disclosed in Table 1. In preferred embodiments, scFvs that immunospecifically bind APRIL polypeptides, without inhibiting APRIL binding to BCMA or TACI, comprise a polypeptide having the amino acid sequence of a VH CDR3 and VL CDR3 from the same scFv referred to in Table 1. In alternative embodiments, scFvs that immunospecifically bind APRIL polypeptides, without inhibiting APRIL binding to BCMA or TACI, comprise a polypeptide having the of the amino acid sequence of a VH CDR3 and VL CDR3 from different scFvs referred to in Table 1. Molecules comprising, or alternatively consisting of, fragments or variants of these scFvs, that immunospecifically bind to APRIL polypeptides, without inhibiting APRIL binding to BCMA or TACI, are also encompassed by the invention, as are nucleic acid molecules encoding these scFvs, molecules, fragments and/or variants, as described, for example, in Table 1.

The present invention provides antibodies (including molecules comprising, or alternatively consisting of, antibody fragments or variants thereof) that immunospecifically bind to a polypeptide or a polypeptide fragment of APRIL. In particular, the invention provides antibodies corresponding to the scFvs referred to in Table 1, such scFvs may routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule, as described in more detail in Example 4.

In one embodiment, the invention provides antibodies (including molecules comprising, or alternatively consisting of, antibody fragments or variants thereof) wherein said antibodies comprise, or alternatively consist of, a polypeptide having an amino acid sequence of any one of the VH domains contained in the sequences referred to in Table 1. The present invention also provides antibodies that immunospecifically bind to a polypeptide, or polypeptide fragment of APRIL, wherein said antibodies comprise, or alternatively consist of, a polypeptide having an amino acid sequence of any one, two, three, or more of the VH CDRs contained in the sequences referred to in Table 1. Molecules comprising, or alternatively consisting of, these antibodies, or antibody fragments or variants thereof, that immunospecifically bind to APRIL or an APRIL fragment are also encompassed by the invention, as are nucleic acid molecules encoding these antibodies, molecules, fragments and/or variants.

In one embodiment of the present invention, antibodies (including molecules comprising, or alternatively consisting of, antibody fragments or variants thereof) that immunospecifically bind APRIL, comprise, or alternatively consist of, a polypeptide having the amino acid sequence of a VH CDR referred to in Table 1. In particular, the invention provides antibodies that immunospecifically bind APRIL, comprising, or alternatively consisting of, a polypeptide having the amino acid sequence of a VH CDR1 contained in SEQ ID NOs:13–15, 16–20, or 21–24 as disclosed in Table 1. In another embodiment, antibodies that immunospecifically bind APRIL, comprise, or alternatively consist of, a polypeptide having the amino acid sequence of a VH CDR2 contained in SEQ ID NOs:13–15, 16–20, or 21–24 as disclosed in Table 1. In a preferred embodiment, antibodies that immunospecifically bind APRIL, comprise, or alternatively consist of a polypeptide having the amino acid sequence of a VH CDR3 contained in SEQ ID NOs:13–15, 16–20, or 21–24 as disclosed in Table 1. In yet another embodiment, antibodies that immunospecifically bind APRIL, comprise, or alternatively consist of, a polypeptide having the amino acid sequence of a VH CDR1 contained in SEQ ID NOs:13–15, 16–20, or 21–24 as disclosed in Table 1; and/or a VH CDR2 contained in SEQ ID NOs:13–15, 16–20, or 21–24 as disclosed in Table 1; and/or a VH CDR3 contained in SEQ ID NOs:13–15, 16–20, or 21–24 as disclosed in Table 1. Preferably, antibodies of the invention comprise, or alternatively consist of, VH CDRs that are derived from the same scFv as disclosed in Table 1. Molecules comprising, or alternatively consisting of, fragments or variants of these antibodies that immunospecifically bind to APRIL are also encompassed by the invention, as are nucleic acid molecules encoding these antibodies, molecules, fragments or variants, as described, for example, in Table 1.

The present invention provides antibodies (including molecules comprising, or alternatively consisting of, antibody fragments or variants) that immunospecifically bind to a polypeptide, or polypeptide fragment of APRIL. In particular, the invention provides antibodies wherein said antibodies comprise, or alternatively consist of, a VL domain having an amino acid sequence of any one of the VL domains referred to in Table 1. The present invention also provides antibodies that immunospecifically bind to a polypeptide or polypeptide fragment of APRIL, wherein said antibodies comprise, or alternatively consist of, a VL CDR having an amino acid sequence of any one, two, three, or more of the VL CDRs contained in the sequences referred to in Table 1. Molecules comprising, or alternatively consisting of, fragments or variants of these antibodies that immunospecifically bind to APRIL are also encompassed by the invention, as are nucleic acid molecules encoding these antibodies, molecules, fragments or variants.

In one embodiment of the present invention, antibodies (including molecules comprising, or alternatively consisting of, antibody fragments or variants thereof) that immunospecifically bind APRIL, comprise, or alternatively consist of, a polypeptide having the amino acid sequence of a VL CDR referred to in Table 1. In particular, the invention provides antibodies that immunospecifically bind APRIL, comprising, or alternatively consisting of, a polypeptide having the amino acid sequence of a VL CDR1 contained in SEQ ID NOs:13–15, 16–20, or 21–24 as disclosed in Table 1. In another embodiment, antibodies that immunospecifically bind APRIL comprise, or alternatively consist of, a polypeptide having the amino acid sequence of a VL CDR2 contained in SEQ ID NOs:13–15, 16–20, or 21–24 as disclosed in Table 1. In a preferred embodiment, antibodies comprise, or alternatively consist of, a polypeptide having the amino acid sequence of a VL CDR3 contained in SEQ ID NOs: 13–15, 16–20, or 21–24 as disclosed in Table 1. In yet another embodiment, antibodies that immunospecifically bind APRIL comprise, or alternatively consist of: a polypeptide having the amino acid sequence of a VL CDR1 contained in SEQ ID NOs:13–15, 16–20, or 21–24 as disclosed in Table 1; and/or a VL CDR2 contained in SEQ ID NOs:13–15, 16–20, or 21–24 as disclosed in Table 1; and/or a VL CDR3 contained in SEQ ID NOs:13–15, 16–20, or 21–24 as disclosed in Table 1. Preferably, antibodies of the invention comprise, or alternatively consist of, VL CDRs that are derived from the same scFv as disclosed in Table 1. Molecules comprising, or alternatively consisting of, fragments or variants of these antibodies, that immunospecifically bind to APRIL are also encompassed by the invention, as are nucleic acid molecules encoding these antibodies, molecules, fragments or variants, referred to in Table 1.

The present invention also provides antibodies (including molecules comprising, or alternatively consisting of, antibody fragments or variants thereof) that immunospecifically bind to a polypeptide or a polypeptide fragment of APRIL, wherein said antibodies comprise, or alternatively consist of, a VH domain of one of the scFvs referred to in Table 1 combined with a VL domain of one of the scFvs referred to in Table 1, or other VL domain. The present invention further provides antibodies (including molecules comprise, or alternatively consist of, antibody fragments or variants thereof) that immunospecifically bind to a polypeptide or a polypeptide fragment of APRIL, wherein said antibodies comprise, or alternatively consist of, a VL domain of one of the scFvs referred to in Table 1 combined with a VH domain of one of the scFvs referred to in Table 1, or other VH domain. In a preferred embodiment, antibodies that immunospecifically bind to a polypeptide or a polypeptide fragment of APRIL, comprise, or alternatively consist of, a polypeptide having the amino acid sequence of a VH domain contained SEQ ID NOs:13–15, 16–20, or 21–24 as disclosed in Table 1 and a VL domain contained in contained SEQ ID NOs:13–15, 16–20, or 21–24 as disclosed in Table 1. In a further preferred embodiment, the antibodies of the invention comprise, or alternatively consist of, a VH and a VL domain from the same scFv as disclosed in Table 1. Molecules comprising, or alternatively consisting of, fragments or variants of these antibodies, that immunospecifically bind to APRIL are also encompassed by the invention, as are nucleic acid molecules encoding these antibodies, molecules, fragments or variants, as described, for example, in Table 1.

The present invention also provides antibodies (including molecules comprising, or alternatively consisting of, antibody fragments or variants) that immunospecifically bind to a polypeptide or polypeptide fragment of APRIL, wherein said antibodies comprise, or alternatively consist of, one, two, three, or more VH CDRs and one, two, three or more VL CDRs, as referred to in Table 1. In particular, the invention provides for antibodies that immunospecifically bind to a polypeptide or polypeptide fragment of APRIL, wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs referred to in Table 1. In a preferred embodiment, one or more of these combinations are from the same scFv as disclosed in Table 1. Molecules comprising, or alternatively consisting of, fragments or variants of these antibodies, that immunospecifically bind to APRIL are also encompassed by the invention, as are nucleic acid molecules encoding these antibodies, molecules, fragments or variants.

In a preferred embodiment the invention provides antibodies wherein the VH CDRX (where X=1, 2, or 3) and VL CDRY (where Y=1, 2, or 3) are from scFvs with the same specificity (e.g., from scFvs that bind APRIL polypeptides and inhibit, partially inhibit, or do not inhibit APRIL binding to BCMA and/or TACI). Molecules comprising, or alternatively consisting of, fragments or variants of these antibodies, that immunospecifically bind to APRIL are also encompassed by the invention, as are nucleic acid molecules encoding these antibodies, molecules, fragments or variants.

The term "antibody," as used herein, refers to immunoglobulin molecules and immunologically active portions of immunoglobulin molecules, i.e., molecules that contain an antigen-binding site that immunospecifically bind an antigen. As such, the term "antibody" encompasses not only whole antibody molecules, but also antibody fragments, as well as variants (including derivatives) of antibodies and antibody fragments. Antibodies of the invention include, but are not limited to, monoclonal, multispecific, human or chimeric antibodies, single chain antibodies, single chain Fvs (scFvs), Fab fragments, F(ab')$_2$ fragments, Fd fragments, disulfide-linked Fvs (sdFvs), antiidiotypic (anti-Id) antibodies (including, e.g., anti-Id antibodies to antibodies of the invention), and epitope-binding fragments of any of the above. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule. The antibodies of the present invention also include molecules comprising, or alternatively consisting of, a polypeptide having an amino acid sequence of a portion of an amino acid sequence contained in SEQ ID NOs:13–15, 16–20, or 21–24. Preferably, an antibody of the invention comprises, or alternatively consists of, a polypeptide having an amino acid sequence of a VH domain, VH CDR, VL domain, or VL CDR of any one those contained in the sequences referred to in Table 1. Antibodies of the invention also include molecules comprising, or alternatively consisting of, fragments or variants of the above antibodies that immunospecifically bind APRIL.

Most preferably the antibodies of the present invention are whole antibodies or antibody fragments that immunospecifically bind human APRIL. Antibody fragments of the invention that immunospecifically bind human APRIL include, but are not limited to, Fab, Fab' and F(ab')$_2$, Fd fragments, single-chain Fvs (scFv), single-chain antibodies, disulfide-linked Fvs (sdFvs), fragments comprising, or alternatively consisting of, either a VL or VH domain, and epitope binding fragments of any of the above.

APRIL-binding antibody fragments, including single-chain antibodies, may comprise, or alternatively consist of, the variable region(s) alone or in combination with the entirety or a portion of the following: hinge region, CH1, CH2, and CH3 domains. In a preferred embodiment, the antibodies of the invention comprise, or alternatively consist of, a polypeptide that immunospecifically binds to APRIL, said polypeptide comprising, or alternatively consisting of, one, two, three, four, five, six or more CDRs referred to in Table 1, preferably a polypeptide having an amino acid sequence of a VH CDR3 and/or a VL CDR3 contained in SEQ ID NOs:13–15, 16–20, 21–24, 25–26, 27–30 or 31–34 as disclosed in Table 1. Most preferably, antibodies of the invention comprise, or alternatively consist of, one, two, three, four, five, six or more CDRs from the same scFv, as referred to in Table 1. The antibodies of the invention may be from any animal origin, including birds and mammals. Preferably, the antibodies are human, murine (e.g., mouse and rat), donkey, sheep, rabbit, goat, guinea pig, camel, horse, or chicken. Most preferably, the antibodies are human antibodies. As used herein, "human" antibodies include antibodies having the amino acid sequence of a human immunoglobulin and include antibodies isolated from human immunoglobulin libraries and xenomice or other organisms that have been genetically engineered to produce human antibodies. For a detailed discussion of a few of the technologies for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; and Lonberg and Huszar, Int. Rev. Immunol. 13:65–93 (1995), which are incorporated by reference herein in their entirety. Human antibodies or "humanized" chimeric monoclonal antibodies can be produced using techniques described herein or otherwise known in the art. For example, methods for producing chimeric antibodies are known in the art. See, for review, the following references which are hereby incorporated in their entirety: Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985). In addition, companies such as Abgenix, Inc. (Freemont, Calif.) and Genpharm (San Jose, Calif.) can be engaged to provide human antibodies directed against a selected antigen using technology similar to that described above.

The antibodies of the present invention may be monovalent, bivalent, trivalent or multivalent. For example, monovalent scFvs can be multimerized either chemically or by association with another protein or substance. An scFv that is fused to a hexahistidine tag or a Flag tag can be multimerized using Ni-NTA agarose (Qiagen) or using anti-Flag antibodies (Stratagene, Inc.).

The antibodies of the present invention may be monospecific, bispecific, trispecific or of greater multispecificity. Multispecific antibodies may be specific for different epitopes of an APRIL polypeptide, or fragment thereof, or may be specific for both an APRIL polypeptide, or fragment thereof, and a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

The antibodies of the invention (including molecules comprising, or alternatively consisting of, antibody fragments or variants thereof) may bind immunospecifically to human APRIL (e.g., a polypeptide having the amino acid sequence of human APRIL (SEQ ID NOs:36 and/or 37) or APRIL expressed on human monocytes. Preferably, the antibodies of the invention bind immunospecifically to human and monkey APRIL. Also preferably, the antibodies of the invention bind immunospecifically to human APRIL and murine APRIL. More preferably, antibodies of the invention, bind immunospecifically and with higher affinity to human APRIL than to murine APRIL.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In a specific embodiment, antibodies of the present invention cross react with BLyS. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under hybridization conditions (as described herein).

In preferred embodiments, the antibodies of the present invention (including molecules comprising, or alternatively consisting of, antibody fragments or variants thereof), immunospecifically bind to APRIL and do not cross-react with any other antigens. In more preferred embodiments, the antibodies of the invention immunospecifically bind to APRIL and do not cross-react with TRAIL, BLyS, Endokine-alpha, TNF-alpha, TNF-beta, Fas-L or LIGHT, TACI, or BCMA (see, for example, Example 2). In further preferred embodiments, the antibodies of the invention immunospecifically bind to APRIL and BLyS and do not cross-react with any other antigens. In yet further preferred embodiments, the antibodies of the invention immunospecifically bind to APRIL and BLyS and do not cross-react with TRAIL, Endokine-alpha, TNF-alpha, TNF-beta, Fas-L or LIGHT.

The present invention also provides for a nucleic acid molecule, generally isolated, encoding an antibody of the invention (including molecules comprising, or alternatively consisting of, antibody fragments or variants thereof), as contained, for example, in SEQ ID NOs:1–12 in Table 1. In one embodiment, a nucleic acid molecule of the invention encodes an antibody comprising, or alternatively consisting of, a VH domain having an amino acid sequence of any one of the VH domains referred to in Table 1. In another embodiment, a nucleic acid molecule of the present invention encodes an antibody comprising, or alternatively consisting of, a VH CDR1 having an amino acid sequence of any one of the VH CDR1s referred to in Table 1. In another embodiment, a nucleic acid molecule of the present invention encodes an antibody comprising, or alternatively consisting of, a VH CDR2 having an amino acid sequence of any one of the VH CDR2s referred to in Table 1. In yet another embodiment, a nucleic acid molecule of the present invention encodes an antibody comprising, or alternatively consisting of, a VH CDR3 having an amino acid sequence of any one of the VH CDR3s referred to in Table 1. Nucleic acid molecules encoding antibodies that immunospecifically bind APRIL and comprise, or alternatively consist of, fragments or variants of the VH domains and/or VH CDRs are also encompassed by the invention.

In another embodiment, a nucleic acid molecule of the invention encodes an antibody (including molecules comprising, or alternatively consisting of, antibody fragments or variants thereof), comprising, or alternatively consisting of, a VL domain having an amino acid sequence of any one of the VL domains referred to in Table 1. In another embodiment, a nucleic acid molecule of the present invention encodes an antibody comprising, or alternatively consisting of, a VL CDR1 having amino acid sequence of any one of the VL CDR1s referred to in Table 1. In another embodiment, a nucleic acid molecule of the present invention encodes an antibody comprising, or alternatively consisting of, a VL CDR2 having an amino acid sequence of any one of the VL CDR2s referred to in Table 1. In yet another embodiment, a nucleic acid molecule of the present invention encodes an antibody comprising, or alternatively consisting of, a VL CDR3 having an amino acid sequence of any one of the VL CDR3s referred to in Table 1. Nucleic acid encoding antibodies that immunospecifically bind APRIL and comprise, or alternatively consist of, fragments or variants of the VL domains and/or VLCDR(s) are also encompassed by the invention.

In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains referred to in Table 1 and a VL domain having an amino acid sequence of any one of the VL domains referred to in Table 1. In another embodiment, a nucleic acid molecule of the invention encodes an antibody comprising, or alternatively consisting of, a VH CDR1, a VL CDR1, a VH CDR2, a VL CDR2, a VH CDR3, a VL CDR3, or any combination thereof having an amino acid sequence referred to in Table 1. Nucleic acid encoding antibodies that immunospecifically bind APRIL and comprise, or alternatively consist of, fragments or variants of the VL and/or domains and/or VHCDR(s) and/or VLCDR(s) are also encompassed by the invention.

The present invention also provides antibodies that comprise, or alternatively consist of, variants (including derivatives) of the VH domains, VH CDRs, VL domains, and VL CDRs described herein, which antibodies immunospecifically bind to APRIL. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. In specific embodiments, the variants encode substitutions of VHCDR3. In a preferred embodiment, the variants have conservative amino acid substitutions at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind APRIL). Following mutagenesis, the encoded protein may routinely be expressed and the functional and/or biological activity of the encoded protein, (e.g., ability to immunospecifically bind APRIL) can be determined using techniques described herein or by routinely modifying techniques known in the art.

The antibodies of the invention include derivatives (i.e., variants) that are modified, e.g., by the covalent attachment of any type of molecule to the antibody such that covalent attachment does not affect the ability of the antibody to immunospecifically bind to APRIL. For example, but not by way of limitation, derivatives of the invention include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

In a specific embodiment, an antibody of the invention (including a molecule comprising, or alternatively consisting of, an antibody fragment or variant thereof), that immunospecifically binds APRIL, comprises, or alternatively consists of, an amino acid sequence encoded by a nucleotide sequence that hybridizes to a nucleotide sequence that is complementary to that encoding one of the VH or VL domains referred to in Table 1 under stringent conditions, e.g., hybridization to filter-bound DNA in 6× sodium chloride/sodium citrate (SSC) at about 45° C. followed by one or more washes in 0.2×SSC/0.1% SDS at about 50–65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1–6.3.6 and 2.10.3). In another embodiment, an antibody of the invention that immunospecifically binds to APRIL, comprises, or alternatively consists of, an amino acid sequence encoded by a nucleotide sequence that hybridizes to a nucleotide sequence that is complementary to that encoding one of the VH CDRs or VL CDRs referred to in Table 1 under stringent conditions, e.g., hybridization under conditions as described above, or under other stringent hybridization conditions which are known to those of skill in the art. In another embodiment, an antibody of the invention that immunospecifically binds to APRIL, comprises, or alternatively consists of, an amino acid sequence encoded by a nucleotide sequence that hybridizes to a nucleotide sequence that is complementary to that encoding one of the VH CDR3s referred to in Table 1 under stringent conditions e.g., hybridization under conditions as described above, or under other stringent hybridization conditions which are known to those of skill in the art. Nucleic acid molecules encoding these antibodies are also encompassed by the invention.

In another embodiment, an antibody (including a molecule comprising, or alternatively consisting of, an antibody fragment or variant thereof), that immunospecifically binds to APRIL comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VH domains referred to in Table 1. In another embodiment, an antibody of the invention that immunospecifically binds to APRIL comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VH CDRs referred to in Table 1. In another embodiment, an antibody of the invention that immunospecifically binds to APRIL comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to any one of the VH CDR3s referred to in Table 1. Nucleic acid molecules encoding these antibodies are also encompassed by the invention.

In another embodiment, an antibody of the invention (including a molecule comprising, or alternatively consisting of, an antibody fragment or variant thereof), that immunospecifically binds to APRIL comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VL domains referred to in Table 1. In another embodiment, an antibody of the invention that immunospecifically binds to APRIL comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VL CDRs referred to in Table 1. In another embodiment, an antibody of the invention that immunospecifically binds to APRIL comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VL CDR3s referred to in Table 1. Nucleic acid molecules encoding these antibodies are also encompassed by the invention.

Antibodies of the present invention (including molecules comprising, or alternatively consisting of, antibody fragments or variants thereof) may also be described or specified in terms of their binding affinity to the soluble form of APRIL and/or membrane-bound form of APRIL. In specific embodiments, antibodies of the invention bind APRIL polypeptides, or fragments or variants thereof, with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention bind APRIL polypeptides or fragments or variants thereof with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind APRIL polypeptides or fragments or variants thereof with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times^{-13}$ M, $10^{-13}$ M, $5\times10^{-14}$ M, $10^{-14}$ M, $5\times10^{-15}$ M, or $10^{-15}$ M. The invention encompasses antibodies that bind APRIL polypeptides with a dissociation constant or $K_D$ that is within any one of the ranges that are between each of the individual recited values. The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to bind to APRIL, the ability to substantially block APRIL/APRIL receptor (e.g., TACI and BCMA) binding, or the ability to block APRIL mediated biological activity (e.g., stimulation of B cell proliferation, differentiation, immunoglobulin production, and B cell survival). Optionally, the antibodies of the invention will bind to the same epitope as at least one of the antibodies specifically referred to herein. Such epitope binding can be routinely determined using assays known in the art.

The present invention also provides for antibodies (including molecules comprising, or alternatively consisting of, antibody fragments or variants thereof), that neutralize APRIL or a fragment thereof, said antibodies comprising, or alternatively consisting of, a portion (i.e., a VH domain, VL domain, VH CDR1, VH CDR2, VH CDR3, VL CDR1, VL CDR2, or VL CDR3) of an scFv referred to in Table 1, more preferably having an amino acid sequence contained in SEQ ID NOs:21–24, even more preferably having an amino acid sequence contained in SEQ ID NOs:16–20, and even more preferably having an amino acid sequence contained in SEQ ID NOs:13–15, as disclosed in Table 1, or a fragment or variant thereof. By an antibody that "neutralizes APRIL or a fragment thereof" is meant an antibody that diminishes or abolishes the ability of APRIL to bind to its receptor (e.g., TACI and BCMA), to stimulate B cell proliferation, to stimulate immunoglobulin secretion by B cells, and/or to stimulate the APRIL receptor signaling cascade. In one embodiment, an antibody that neutralizes APRIL or a fragment thereof, comprises, or alternatively consists of, a polypeptide having the amino acid sequence of a VH domain contained in SEQ ID NOs:13–15, 16–20, or 21–24 as disclosed in Table 1, or a fragment or variant thereof. In another embodiment, an antibody that neutralizes APRIL or a fragment thereof, comprises, or alternatively consists of, a polypeptide having the amino acid sequence of a VL domain contained in SEQ ID NOs:13–15, 16–20, or 21–24 as disclosed in Table 1, or a fragment or variant thereof. In another embodiment, an antibody that neutralizes APRIL or a fragment thereof, comprises, or alternatively consists of, a polypeptide having the amino acid sequence of a VH CDR domain in SEQ ID NOs:13–15, 16–20, or 21–24 as disclosed in Table 1, or a fragment or variant thereof. In a preferred embodiment, an antibody that neutralizes APRIL or a fragment thereof, comprises, or alternatively consists of, a polypeptide having the amino acid sequence of a VH CDR3 contained in SEQ ID NOs: SEQ ID NOs:13–15, 16–20, or 21–24 as disclosed in Table 1, or a fragment or variant thereof. In another embodiment, an antibody that neutralizes APRIL or a fragment thereof, comprises, or alternatively consists of, a polypeptide having the amino acid sequence of a VL CDR domain contained in SEQ ID NOs:13–15, 16–20, or 21–24 as disclosed in Table 1, or a fragment or variant thereof. In another preferred embodiment, an antibody that neutralizes APRIL or a fragment thereof, comprises, or alternatively consists of, a polypeptide having the amino acid sequence of a VL CDR3 contained in SEQ ID NOs:13–15, 16–20, or 21–24 as disclosed in Table 1, or a fragment or variant thereof. Nucleic acid molecules encoding these antibodies, as described, for example, as SEQ ID NOs:1–12 in Table 1, are also encompassed by the invention.

The present invention also provides for antibodies (including molecules comprising, or alternatively consisting of, antibody fragments or variants thereof), that inhibit (i.e., diminish or abolish) APRIL mediated B cell proliferation as determined by any method known in the art such as, for example, the assays described in Examples 5 and 6, infra, said antibodies comprising, or alternatively consisting of, a portion (e.g., a VH domain, VL domain, VH CDR1, VH CDR2, VH CDR3, VL CDR1, VL CDR2, or VL CDR3) of an scFv having an amino acid sequence contained in SEQ ID NOs:13–15, 16–20, or 21–24 as disclosed in Table 1 or a fragment or variant thereof. In one embodiment, an antibody that inhibits APRIL mediated B cell proliferation, comprises, or alternatively consists of, a polypeptide having the amino acid sequence of a VH domain contained in SEQ ID NOs:13–15, 16–20, or 21–24 as disclosed in Table 1, or a fragment or variant thereof. In another embodiment, an antibody that inhibits APRIL mediated B cell proliferation, comprises, or alternatively consists of, a polypeptide having the amino acid sequence of a VL domain contained in SEQ ID NOs:13–15, 16–20, or 21–24 as disclosed in Table 1, or a fragment or variant thereof. In a preferred embodiment, an antibody that inhibits APRIL mediated B cell proliferation, comprises, or alternatively consists of, a polypeptide having the amino acid sequence of a VH CDR contained in SEQ ID NOs:13–15, 16–20, or 21–24 as disclosed in Table 1, or a fragment or variant thereof. In another preferred embodiment, an antibody that inhibits APRIL mediated B cell proliferation, comprises, or alternatively consists of, a polypeptide having the amino acid sequence of a VL CDR contained SEQ ID NOs:13–15, 16–20, or 21–24 as disclosed in Table 1, or a fragment or variant thereof. In a preferred embodiment, an antibody that inhibits APRIL mediated B cell proliferation, comprises, or alternatively consists of, a polypeptide having the amino acid sequence of a VH CDR3 contained in SEQ ID NOs:13–15, 16–20, or 21–24 as disclosed in Table 1, or a fragment or variant thereof. In another embodiment, an antibody that inhibits APRIL mediated B cell proliferation, comprises, or alternatively consists of, a polypeptide having the amino acid sequence of a VL CDR3 contained SEQ ID NOs:13–15, 16–20, or 21–24 as disclosed in Table 1, or a fragment or variant thereof. Nucleic acid molecules encoding these antibodies, as described, for example, in Table 1, are also encompassed by the invention.

The present invention also provides for antibodies (including molecules comprising, or alternatively consisting of, antibody fragments or variants thereof), that inhibit (i.e., diminish or abolish) APRIL mediated immunoglobulin production as determined by any method known in the art, said antibodies comprising, or alternatively consisting of, a portion (e.g., a VH domain, VL domain, VH CDR1, VH CDR2, VH CDR3, VL CDR1, VL CDR2, or VL CDR3) of an scFv having an amino acid sequence contained in SEQ ID NOs: 13–24 as disclosed in Table 1 or a fragment or variant thereof. In one embodiment, an antibody that inhibits APRIL mediated immunoglobulin production, comprises, or alternatively consists of, a polypeptide having the amino acid sequence of a VH domain contained in SEQ ID NOs:13–24 as disclosed in Table 1, or a fragment or variant thereof. In another embodiment, an antibody that inhibits APRIL mediated immunoglobulin production, comprises, or alternatively consists of, a polypeptide having the amino acid sequence of a VL domain contained in SEQ ID NOs:13–24 as disclosed in Table 1, or a fragment or variant thereof. In a preferred embodiment, an antibody that inhibits APRIL mediated immunoglobulin production, comprises, or alternatively consists of, a polypeptide having the amino acid sequence of a VH CDR contained in SEQ ID NOs:13–24 as disclosed in Table 1, or a fragment or variant thereof. In another preferred embodiment, an antibody that inhibits APRIL mediated immunoglobulin production, comprises, or alternatively consists of, a polypeptide having the amino acid sequence of a VL CDR contained SEQ ID NOs:13–24 as disclosed in Table 1, or a fragment or variant thereof. In a preferred embodiment, an antibody that inhibits APRIL mediated immunoglobulin production, comprises, or alternatively consists of, a polypeptide having the amino acid sequence of a VH CDR3 contained in SEQ ID NOs:13–24 as disclosed in Table 1, or a fragment or variant thereof. In another preferred embodiment, an antibody that inhibits APRIL mediated immunoglobulin production, comprises, or alternatively consists of, a polypeptide having the amino acid sequence of a VL CDR3 contained SEQ ID NOs:13–24 as disclosed in Table 1, or a fragment or variant thereof. Nucleic acid molecules encoding these antibodies, as described, for example, in Table 1, are also encompassed by the invention.

The present invention also provides for antibodies (including molecules comprising, or alternatively consisting of, antibody fragments or variants thereof), that inhibit (i.e., diminish or abolish) APRIL mediated B cell survival as determined by any method known in the art such as, for example, the assays described in Examples 5 and 6, infra, said antibodies comprising, or alternatively consisting of, a portion (e.g., a VH domain, VL domain, VH CDR1, VH CDR2, VH CDR3, VL CDR1, VL CDR2, or VL CDR3) of an scFv having an amino acid sequence contained in SEQ ID NOs:13–24 as disclosed in Table 1 or a fragment or variant thereof. In one embodiment, an antibody that inhibits APRIL mediated B cell survival, comprises, or alternatively consists of, a polypeptide having the amino acid sequence of a VH domain contained in SEQ ID NOs:13–24 as disclosed in Table 1, or a fragment or variant thereof. In another embodiment, an antibody that inhibits APRIL mediated B cell survival, comprises, or alternatively consists of, a polypeptide having the amino acid sequence of a VL domain contained in SEQ ID NOs:13–24 as disclosed in Table 1, or a fragment or variant thereof. In a preferred embodiment, an antibody that inhibits APRIL mediated B cell survival, comprises, or alternatively consists of, a polypeptide having the amino acid sequence of a VH CDR contained in SEQ ID NOs:13–24 as disclosed in Table 1, or a fragment or variant thereof. In another preferred embodiment, an antibody that inhibits APRIL mediated B cell survival, comprises, or alternatively consists of, a polypeptide having the amino acid sequence of a VL CDR contained SEQ ID NOs:13–24 as disclosed in Table 1, or a fragment or variant thereof. In a preferred embodiment, an antibody that inhibits APRIL mediated B cell survival, comprises, or alternatively consists of, a polypeptide having the amino acid sequence of a VH CDR3 contained in SEQ ID NOs:13–24 as disclosed in Table 1, or a fragment or variant thereof. In another preferred embodiment, an antibody that inhibits APRIL mediated B cell survival, comprises, or alternatively consists of, a polypeptide having the amino acid sequence of a VL CDR3 contained SEQ ID NOs:13–24 as disclosed in Table 1, or a fragment or variant thereof. Nucleic acid molecules encoding these antibodies, as described, for example, in Table 1, are also encompassed by the invention.

The present invention also provides for antibodies (including molecules comprising, or alternatively consisting of, antibody fragments or variants thereof), that enhance the activity of APRIL or a fragment thereof, said antibodies comprising, or alternatively consisting of, a portion (i.e., a VH domain, VL domain, VH CDR1, VH CDR2, VH CDR3, VL CDR1, VL CDR2, or VL CDR3) of an scFv having an amino acid sequence contained in SEQ ID NOs:13–15, 16–20, or 21–24 as disclosed in Table 1, or a fragment or variant thereof. By an antibody that "enhances the activity of APRIL or a fragment thereof" is meant an antibody increases the ability of APRIL to bind to its receptor (e.g., TACI, BCMA), to stimulate B cell proliferation, to stimulate immunoglobulin secretion by B cells, to enhance B cell survival and/or to stimulate the APRIL receptor signaling cascade. In one embodiment, an antibody that enhances the activity of APRIL or a fragment thereof, comprises, or alternatively consists of, a polypeptide having the amino acid sequence of a VH domain contained in SEQ ID NOs:13–15, 16–20, or 21–24 as disclosed in Table 1, or a fragment or variant thereof. In another embodiment, an antibody that enhances the activity of APRIL or a fragment thereof, comprises, or alternatively consists of, a polypeptide having the amino acid sequence of a VL domain contained in SEQ ID NOs:13–15, 16–20, or 21–24 as disclosed in Table 1, or a fragment or variant thereof. In another embodiment, an antibody that enhances the activity of APRIL or a fragment thereof, comprises, or alternatively consists of, a polypeptide having the amino acid sequence of a VH CDR domain contained in SEQ ID NOs:13–15, 16–20, or 21–24 as disclosed in Table 1, or a fragment or variant thereof. In a preferred embodiment, an antibody that enhances the activity of APRIL or a fragment thereof, comprises, or alternatively consists of, a polypeptide having the amino acid sequence of a VH CDR3 contained in SEQ ID NOs:13–15, 16–20, or 21–24 as disclosed in Table 1, or a fragment or variant thereof. In another embodiment, an antibody that enhances APRIL or a fragment thereof, comprises, or alternatively consists of, a polypeptide having the amino acid sequence of a VL CDR domain contained in SEQ ID NOs:13–15, 16–20, or 21–24 as disclosed in Table 1, or a fragment or variant thereof. In another preferred embodiment, an antibody that enhances the activity of APRIL or a fragment thereof, comprises, or alternatively consists of, a polypeptide having the amino acid sequence of a VL CDR3 contained in SEQ ID NOs:13–15, 16–20, or 21–24 as disclosed in Table 1, or a fragment or variant thereof. Nucleic acid molecules encoding these antibodies, as contained, for example, in SEQ ID NOs:1–12 in Table 1, are also encompassed by the invention.

The present invention also provides for antibodies (including molecules comprising, or alternatively consisting of, antibody fragments or variants thereof), that stimulate APRIL mediated B cell proliferation as determined by any method known in the art, such as, for example, the assays described in Examples 5 and 6, infra, said antibodies comprising, or alternatively consisting of, a portion (e.g., a VH domain, VL domain, VH CDR1, VH CDR2, VH CDR3, VL CDR1, VL CDR2, or VL CDR3) of an scFv having an amino acid sequence of SEQ ID NOs:13–15, 16–20, or 21–24 as disclosed in Table 1 or a fragment or variant thereof. In one embodiment, an antibody that stimulates APRIL mediated B cell proliferation, comprises, or alternatively consists of, a polypeptide having the amino acid sequence of a VH domain contained in SEQ ID NOs:13–15, 16–20, or 21–24 as disclosed in Table 1, or a fragment or variant thereof. In another embodiment, an antibody that stimulates APRIL mediated B cell proliferation, comprises, or alternatively consists of, a polypeptide having the amino acid sequence of a VL domain contained in SEQ ID NOs:13–15, 16–20, or 21–24 as disclosed in Table 1, or a fragment or variant thereof. In a preferred embodiment, an antibody that stimulates APRIL mediated B cell proliferation, comprises, or alternatively consists of, a polypeptide having the amino acid sequence of a VH CDR contained in SEQ ID NOs: 13–15, 16–20, or 21–24 as disclosed in Table 1, or a fragment or variant thereof. In another preferred embodiment, an antibody that stimulates APRIL mediated B cell proliferation, comprises, or alternatively consists of, a polypeptide having the amino acid sequence of a VL CDR contained in SEQ ID NOs:13–15, 16–20, or 21–24 as disclosed in Table 1, or a fragment or variant thereof. In a preferred embodiment, an antibody that stimulates APRIL mediated B cell proliferation, comprises, or alternatively consists of, a polypeptide having the amino acid sequence of a VH CDR3 contained in SEQ ID NOs:13–15, 16–20, or 21–24 as disclosed in Table 1, or a fragment or variant thereof. In another preferred embodiment, an antibody that stimulates APRIL mediated B cell proliferation, comprises, or alternatively consists of, a polypeptide having the amino acid sequence of a VL CDR3 contained in SEQ ID NOs: 13–15, 16–20, or 21–24 as disclosed in Table 1, or a fragment or variant thereof. Nucleic acid molecules encoding these antibodies, as contained, for example, in SEQ ID NOs:1–12 in Table 1, are also encompassed by the invention.

The present invention also provides for antibodies (including molecules comprising, or alternatively consisting of, antibody fragments or variants thereof), that immunospecifically bind to APRIL polypeptides and do not inhibit, enhance or stimulate the activity of APRIL, or stimulate B cell proliferation as determined by any method known in the art, such as, for example, the assays described in Examples 5 and 6, infra, said antibodies comprising, or alternatively consisting of, a portion (e.g., a VH domain, VL domain, VH CDR1, VH CDR2, VH CDR3, VL CDR1, VL CDR2, or VL CDR3) of an scFv having an amino acid sequence of SEQ ID NOs:13–15, 16–20, or 21–24 as disclosed in Table 1 or a fragment or variant thereof. In one embodiment, an antibody that immunospecifically binds to APRIL polypeptides and does not inhibit, enhance or stimulate the activity of APRIL, or stimulate B cell proliferation, comprises, or alternatively consists of, a polypeptide having the amino acid sequence of a VH domain contained in SEQ ID NOs:13–15, 16–20, or 21–24 as disclosed in Table 1, or a fragment or variant thereof. In another embodiment, an antibody that immunospecifically binds to APRIL polypeptides and does not inhibit, enhance or stimulate the activity of APRIL, or stimulate B cell proliferation, comprises, or alternatively consists of, a polypeptide having the amino acid sequence of a VL domain contained in SEQ ID NOs: 13–15, 16–20, or 21–24 as disclosed in Table 1, or a fragment or variant thereof. In a preferred embodiment, an antibody that immunospecifically binds to APRIL polypeptides and does not inhibit, enhance or stimulate the activity of APRIL, or stimulate B cell proliferation, comprises, or alternatively consists of, a polypeptide having the amino acid sequence of a VH CDR contained in SEQ ID NOs: 13–15, 16–20, or 21–24 as disclosed in Table 1, or a fragment or variant thereof. In another preferred embodiment, an antibody that immunospecifically binds to APRIL polypeptides and does not inhibit, enhance or stimulate the activity of APRIL, or stimulate B cell proliferation, comprises, or alternatively consists of, a polypeptide having the amino acid sequence of a VL CDR contained in SEQ ID NOs:13–15, 16–20, or 21–24 as disclosed in Table 1, or a fragment or variant thereof. In a preferred embodiment, an antibody that immunospecifically binds to APRIL polypeptides and does not inhibit, enhance or stimulate the activity of APRIL, or stimulate B cell proliferation, comprises, or alternatively consists of, a polypeptide having the amino acid sequence of a VH CDR3 contained in SEQ ID NOs: 13–15, 16–20, or 21–24 as disclosed in Table 1, or a fragment or variant thereof. In another preferred embodiment, an antibody that immunospecifically binds to APRIL polypeptides and does not inhibit, enhance or stimulate the activity of APRIL, or stimulate B cell proliferation, comprises, or alternatively consists of, a polypeptide having the amino acid sequence of a VL CDR3 contained in SEQ ID NOs:13–15, 16–20, or 21–24 as disclosed in Table 1, or a fragment or variant thereof. Nucleic acid molecules encoding these antibodies, as contained, for example, in SEQ ID NOs:1–12 in Table 1, are also encompassed by the invention.

The present invention also provides for fusion proteins comprising, or alternatively consisting of, an antibody (including molecules comprising, or alternatively consisting of, antibody fragments or variants thereof), that immunospecifically binds to APRIL, and a heterologous polypeptide. Preferably, the heterologous polypeptide to which the antibody is fused to is useful for B-cell function or is useful to target the antibody to B-cells. In an alternative preferred embodiment, the heterologous polypeptide to which the antibody is fused is useful for monocyte cell function or is useful to target the antibody to a monocyte. In one embodiment, a fusion protein of the invention comprises, or alternatively consists of, a polypeptide having the amino acid sequence of any one or more of the VH domains referred to in Table 1 or the amino acid sequence of any one or more of the VL domains referred to in Table 1 or fragments or variants thereof, and a heterologous polypeptide sequence. In another embodiment, a fusion protein of the present invention comprises, or alternatively consists of, a polypeptide having the amino acid sequence of any one, two, three, or more of the VH CDRs referred to in Table 1, or the amino acid sequence of any one, two, three, or more of the VL CDRs referred to in Table 1, or fragments or variants thereof, and a heterologous polypeptide sequence. In a preferred embodiment, the fusion protein comprises, or alternatively consists of, a polypeptide having the amino acid sequence of, a VH CDR3 referred to in Table 1, or fragment or variant thereof, and a heterologous polypeptide sequence, which fusion protein immunospecifically binds to APRIL. In another embodiment, a fusion protein comprises, or alternatively consists of a polypeptide having the amino acid sequence of at least one VH domain referred to in Table 1 and the amino acid sequence of at least one VL domain referred to in Table 1 or fragments or variants thereof, and a heterologous polypeptide sequence. Preferably, the VH and VL domains of the fusion protein correspond to the same scFv referred to in Table 1. In yet another embodiment, a fusion protein of the invention comprises, or alternatively consists of a polypeptide having the amino acid sequence of any one, two, three or more of the VH CDRs referred to in Table 1 and the amino acid sequence of any one, two, three or more of the VL CDRs referred to in Table 1, or fragments or variants thereof, and a heterologous polypeptide sequence. Preferably, two, three, four, five, six, or more of the VHCDR(s) or VLCDR(s) correspond to the same scFv referred to in Table 1. Nucleic acid molecules encoding these fusion proteins are also encompassed by the invention.

The present invention also provides for mixtures of antibodies (including scFvs and other molecules comprising, or alternatively consisting of, antibody fragments or variants thereof) that immunospecifically bind to APRIL, wherein the mixture has at least one, two, three, four, five or more different antibodies of the invention. In particular, the invention provides for mixtures of different antibodies that immunospecifically bind APRIL polypeptides, regulating APRIL binding to its receptors (e.g. BCMA and TACI). In specific embodiments, the invention provides mixtures of at least 2, preferably at least 4, at least 6, at least 8, at least 10, at least 12, at least 15, at least 20, or at least 25 different antibodies that immunospecifically bind to APRIL, wherein at least 1, at least 2, at least 4, at least 6, or at least 10, antibodies of the mixture is an antibody of the invention. In a specific embodiment, each antibody of the mixture is an antibody of the invention.

The present invention also provides for panels of antibodies (including scFvs and other molecules comprising, or alternatively consisting of, antibody fragments or variants thereof) that immunospecifically bind to APRIL, wherein the panel has at least one, two, three, four, five or more different antibodies of the invention. In particular, the invention provides for panels of different antibodies that immunospecifically bind APRIL polypeptides, regulating APRIL binding to its receptors (e.g. BCMA and TACI). In specific embodiments, the invention provides for panels of antibodies that have different affinities for APRIL, different specificities for APRIL, or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000, antibodies. Panels of antibodies can be used, for example, in 96 well plates for assays such as ELISAs.

The present invention further provides for compositions comprising, one or more antibodies (including scFvs and other molecules comprising, or alternatively consisting of, antibody fragments or variants of the invention). In one embodiment, a composition of the present invention comprises, one, two, three, four, five, or more antibodies that comprise or alternatively consist of, a polypeptide having an amino acid sequence of any one or more of the VH domains contained in SEQ ID NOs:13–15, 16–20, or 21–24, as disclosed in Table 1, or a variant thereof. In another embodiment, a composition of the present invention comprises, one, two, three, four, five, or more antibodies that comprise, or alternatively consist of, a polypeptide having an amino acid sequence of any one or more of the VH CDR1s contained in SEQ ID NOs:13–15, 16–20, or 21–24, as disclosed in Table 1, or a variant thereof. In another embodiment, a composition of the present invention comprises, one, two, three, four, five or more antibodies that comprise, or alternatively consist of, a polypeptide having an amino acid sequence of any one or more of the VH CDR2s contained in SEQ ID NOs:13–15, 16–20, or 21–24, as disclosed in Table 1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3s contained in SEQ ID NOs:13–15, 16–20, or 21–24, as disclosed in Table 1 or a variant thereof. In another embodiment, a composition of the present invention comprises, one, two, three, four, five, or more antibodies that comprise, or alternative consist of, a polypeptide having an amino acid sequence of any one or more of the VL domains contained in SEQ ID NOs:13–15, 16–20, or 21–24, as disclosed in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR1s contained in SEQ ID NOs:13–15, 16–20, or 21–24, as disclosed in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR2s contained SEQ ID NOs:13–15, 16–20, or 21–24, as disclosed in Table 1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3s contained in SEQ ID NOs:13–15, 16–20, or 21–24, as disclosed in Table 1, or a variant thereof. Nucleic acid molecules encoding the antibodies of these compositions, as disclosed for example, as SEQ ID NOs:1–12 in Table 1, are also encompassed by the invention.

In a preferred embodiment, a composition of the present invention comprises, one, two, three, four, five, or more antibodies that comprise, or alternatively consist of, a polypeptide having an amino acid sequence of any one or more of the VH domains in disclosed in Table 1, or a variant thereof, and an amino acid sequence of any one or more of the VL domains disclosed in Table 1, or a variant thereof wherein the VH and VL domains are from scFvs with the same specificity (e.g., from scFvs that bind APRIL (SEQ ID NOs:13–24)). In a preferred embodiment the invention provides antibodies wherein the VH CDRX (where X=1,2, or 3) and VL CDRY (where Y=1,2, or 3) are from scFvs with the same specificity (e.g., from scFvs that bind APRIL (SEQ ID NOs:13–24)). In yet another embodiment, a composition of the present invention comprises one or more fusion proteins.

As discussed in more detail below, a composition of the invention may be used either alone or in combination with other compositions. The antibodies (including scFvs and other molecules comprising, or alternatively consisting of antibody fragments or variants of the present invention) may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Antibodies of the present invention (including scFvs and other molecules comprising, or alternatively consisting of antibody fragments or variants of the present invention) may be used, for example, but not limited to, to purify and detect APRIL, and to target the polypeptides of the present invention to cells expressing membrane-bound APRIL or APRIL receptor, including both in vitro and in vivo diagnostic and therapeutic methods. For example, the antibodies have use in immunoassays for qualitatively and quantitatively measuring levels of APRIL in biological samples. See, e.g., Harlow et al., Antibodies: A Laboratory Manual, (Cold Spring Harbor Laboratory Press, 2nd ed. 1988) (incorporated by reference herein in its entirety).

Methods for Producing Antibodies

The antibodies of the invention (including scFvs and other molecules comprising, or alternatively consisting of antibody fragments or variants of the invention) can be produced by any method known in the art for the synthesis of antibodies, in particular, by chemical synthesis or preferably, by recombinant expression techniques.

The single chain Fvs disclosed in Table 1 were generated using phage display methods known in the art. Furthermore, other scFvs that immunospecifically bind APRIL may be generated using phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues) or synthetic cDNA libraries. The DNA encoding the VH and VL domains are joined together by an scFv linker by PCR and cloned into a phagemid vector (e.g., p CANTAB 6 or pComb 3 HSS). The vector is electroporated in E. coli and the E. coli is infected with helper phage. Phages used in these methods are typically filamentous phages including fd and M13, and the VH and VL domains are usually recombinantly fused to either the phage gene III or gene VIII. Phage expressing an antigen-binding domain that binds to an antigen of interest (i.e., APRIL or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41–50 (1995); Ames et al., J. Immunol. Methods 184: 177–186 (1995); Kettleborough et al., Eur. J. Immunol. 24:952–958 (1994); Persic et al., Gene 187 9–18 (1997); Burton et al., Advances in Immunology 57:191–280(1994); PCT application No. PCT/GB91/O1 134; PCT publications WO 90/02809; WO 91/10737; WO 92/01047; WO 92/18619; WO 93/11236; WO 95/15982; WO 95/20401; WO97/13844; and U.S. Pat. Nos. 5,698,426; 5,223,409;

5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); Sawai et al., AJRI 34:26–34 (1995); and Better et al., Science 240:1041–1043 (1988) (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human patients. See also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. In a specific embodiment, antibodies of the present invention comprise one or more VH and VL domains corresponding to the human scFvs of the invention and framework regions from another immunoglobulin molecule, preferably a human immunoglobulin molecule. In a specific embodiment, antibodies of the present invention comprise one or more CDRs corresponding to the human scFvs of the invention and framework regions from another immunoglobulin molecule, preferably a human immunoglobulin molecule. In other embodiments, an antibody of the present invention comprises one, two, three, four, five, six or more VL CDRs or VH CDRs corresponding to one or more of the human scFvs referred to in Table 1, or fragments or variants thereof, and framework regions (and, optionally CDRs not derived from the scFvs in Table 1) from a human immunoglobulin molecule. In a preferred embodiment, an antibody of the present invention comprises a VH CDR3, VL CDR3, or both, of the same scFv, or different scFvs referred to in Table 1, or fragments or variants thereof, and framework regions from a human immunoglobulin.

A chimeric antibody is a molecule in which different portions of the antibody are derived from different immunoglobulin molecules such as antibodies having a variable region derived from a human antibody and a non-human immunoglobulin constant region. Methods for producing chimeric antibodies are known in the art. See e.g., Morrison, Science 229:1202 (1985); Oi et al., BioTechniques 4:214 (1986); Gillies et al., J. Immunol. Methods 125:191–202 (1989); U.S. Pat. Nos. 5,807,715; 4,816,567; and 4,816,397, which are incorporated herein by reference in their entirety. Chimeric antibodies comprising one or more CDRs from human species and framework regions from a non-human immunoglobulin molecule (e.g., framework regions from a canine or feline immunoglobulin molecule) can be produced using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska et al., PNAS 91:969–973 (1994)), and chain shuffling (U.S. Pat. No. 5,565,332). In a preferred embodiment, chimeric antibodies comprise a human CDR3 having an amino acid sequence of any one of the VH CDR3s or VL CDR3s referred to in Table 1, or a variant thereof, and non-human framework regions or human framework regions different from those of the frameworks in the corresponding scFv disclosed in Table 1. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.)

Further, the antibodies of the invention can, in turn, be utilized to generate anti-idiotype antibodies that "mimic" APRIL polypeptides using techniques well known to those skilled in the art. (See, e.g., Greenspan & Bona, FASEB J. 7(5):437–444 (1993); and Nissinoff, J. Immunol. 147(8): 2429–2438 (1991)). For example, antibodies of the invention which bind to APRIL and competitively inhibit the binding of APRIL to its receptor (as determined by assays well known in the art such as, for example, that disclosed, infra) can be used to generate antiidiotypes that "mimic" an APRIL ligand/receptor-binding domain and, as a consequence, bind to and neutralize APRIL receptors (e.g., TACI, BCMA, and TR20). Such neutralizing anti-idiotypes (including molecules comprising, or alternatively consisting of, antibody fragments or variants, such as Fab fragments of such anti-idiotypes) can be used in therapeutic regimens to neutralize APRIL. For example, such anti-idiotypic antibodies can be used to bind APRIL ligands/receptors, and thereby block APRIL mediated biological activity. Alternatively, anti-idiotypes that "mimic" an APRIL binding domain may bind to APRIL receptor(s) and induce APRIL receptor mediated signaling (e.g., activation of nuclear factor of activated T cells (NF-AT), nuclear factor-kappa B (NF-kappa B), and/or AP-1). Such agonistic anti-idiotypes (including agonistic Fab fragments of these anti-idiotypes) can be used in therapeutic regimens to induce or enhance APRIL receptor mediated signaling. For example, such anti-idiotypic antibodies can be used to bind APRIL ligands/receptors, and thereby stimulate APRIL mediated biological activity (e.g., B cell proliferation and/or immunoglobulin production).

Once an antibody molecule of the invention (including molecules comprising, or alternatively consisting of, antibody fragments or variants thereof) has been chemically synthesized or recombinantly expressed, it may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

Polynucleotides Encoding an Antibody

The invention provides polynucleotides comprising, or alternatively consisting of, a nucleotide sequence encoding an antibody of the invention (including molecules comprising, or alternatively consisting of, antibody fragments or variants thereof). The invention also encompasses polynucleotides that hybridize under high stringency, or alternatively, under intermediate or lower stringency hybridization conditions, e.g., as defined supra, to polynucleotides complementary to nucleic acids having a polynucleotide sequence that encodes an antibody of the invention or a fragment or variant thereof.

The polynucleotides may be obtained, and the nucleotide sequence of the polynucleotides determined, by any method known in the art. Since the amino acid sequences of the scFv antibodies and VH domains, VL domains and CDRs thereof, are known (as described in Table 1), nucleotide sequences encoding these antibodies can be determined using methods well known in the art, i.e., the nucleotide codons known to encode the particular amino acids are assembled in such a way to generate a nucleic acid that encodes the antibody, of the invention. Such a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody (including molecules comprising, or alternatively consisting of, antibody fragments or variants thereof) may be generated from nucleic acid from a suitable source. If a clone containing a nucleic acid encoding a particular antibody is not available, but the sequence of the antibody molecule is known (e.g., SEQ ID NO:1–12, Table 1), a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody (including molecules comprising, or alternatively consisting of, antibody fragments or variants thereof) is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the VH and VL domains referred to in Table 1, or fragments or variants thereof, is inserted within framework regions using recombinant DNA techniques known in the art. In a specific embodiment, one, two, three, four, five, six, or more of the CDRs referred to in Table 1, or fragments or variants thereof, is inserted within framework regions using recombinant DNA techniques known in the art. The framework regions may be naturally occurring or consensus framework regions, and preferably human framework regions (see, e.g., Chothia et al., J. Mol. Biol. 278: 457–479 (1998) for a listing of human framework regions, the contents of which are hereby incorporated by reference in its entirety). Preferably, the polynucleotides generated by the combination of the framework regions and CDRs encode an antibody (including molecules comprising, or alternatively consisting of, antibody fragments or variants thereof) that specifically binds to APRIL. Preferably, as discussed supra, polynucleotides encoding variants of antibodies or antibody fragments having one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules, or antibody fragments or variants, lacking one or more intrachain disulfide bonds. Other alterations to the polynucleotide are encompassed by the present invention and fall within the ordinary skill of the art.

Recombinant Expression of an Antibody

Recombinant expression of an antibody of the invention (including scFvs and other molecules comprising, or alternatively consisting of, antibody fragments or variants thereof (e.g., a heavy or light chain of an antibody of the invention or a portion thereof or a single chain antibody of the invention)), requires construction of an expression vector(s) containing a polynucleotide that encodes the antibody. Once a polynucleotide encoding an antibody molecule (e.g., a whole antibody, a heavy or light chain of an antibody, or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art, can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464, the contents of each of which are hereby incorporated by reference in its entirety) and the variable domain of the antibody may be cloned into such a vector for expression of the entire heavy chain, the entire light chain, or both the entire heavy and light chains.

The expression vector(s) is/are transferred to a host cell by conventional techniques and the transfected cells are then cultured by conventional techniques to produce an antibody of the invention. Thus, the invention includes host cells containing polynucleotide(s) encoding an antibody of the invention (e.g., whole antibody, a heavy or light chain thereof, or portion thereof, or a single chain antibody of the invention, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., NS0, CHO, COS, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified, may be desirable. Such vectors include, but are not limited to, the *E. coli* expression vector pUR278 (Ruther et al., EMBO 1. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) may be used as a vector to express foreign genes. The virus grows in *Spodoptera frugiperda* cells. Antibody coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, NS0, CHO, VERY, BHK, HeLa, COS, NSO, MDCK, 293, 3T3, W138, and in particular, breast cancer cell lines such as, for example, BT483, Hs578T, HTB2, BT2O and T47D, and normal mammary gland cell line such as, for example, CRL7O3O and HsS78Bst.

For long-term, high-yield production of recombinant proteins, stable expression is preferred. For example, cell lines which stably express the antibody, may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); TIB TECH 11(5):155–215 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the coding sequence of the antibody, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NS0) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are incorporated in their entireties by reference herein. Additionally, glutamine synthase expression vectors that may be used according to the present invention are commercially available from suppliers, including, for example Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are incorporated in their entireties by reference herein.

The host cell may be co-transfected with two expression vectors of the invention, the first vector encoding a heavy chain derived polypeptide and the second vector encoding a light chain derived polypeptide. The two vectors may contain identical selectable markers, which enable equal expression of heavy and light chain polypeptides. Alternatively, a single vector may be used which encodes, and is capable of expressing both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA.

Once an antibody molecule of the invention has been produced by recombinant expression, it may be purified by any method known in the art for purification of an immunoglobulin molecule, or more generally, for purification of a protein, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art to facilitate purification.

Antibody Characterization

Antibodies of the present invention (including scFvs and other molecules comprising, or alternatively consisting of, antibody fragments or variants thereof) may be characterized in a variety of ways. In particular, antibodies and related molecules of the invention may be assayed for the ability to immunospecifically bind to APRIL or a fragment of APRIL (e.g., to a soluble or membrane-bound form of APRIL) using techniques described herein or routinely modified techniques known in the art. APRIL or APRIL fragments that may be immunospecifically bound by the compositions of the invention include, but are not-limited to, human APRIL (SEQ ID NOs:36 and/or 37) or APRIL expressed on human monocytes or fragments thereof. Preferably compositions of the invention bind human APRIL (SEQ ID NOs:36 and/or 37) or fragments thereof. Antibodies of the present invention may be assayed for the ability to bind APRIL polypeptides where said polypeptides consist of monomers or multimers (i.e., dimers, trimers, tetramers and higher multimers). Antibodies of the invention may be assayed for the ability to bind multimeric APRIL polypeptides where said polypeptides consist of homotrimers (i.e., containing only APRIL polypeptides including APRIL fragments, variants, and fusion proteins, as described herein) or heterotrimers (i.e., containing heterologous polypeptides in addition to APRIL polypeptides having identical or different amino acid sequences, as contained in SEQ ID NO:36 and SEQ ID NO:37). Specifically, antibodies of the invention may be assayed for the ability to bind an APRIL heterotrimer where said heterotrimer consists of one APRIL polypeptide and two BLyS polypeptides, or alternatively, two APRIL polypeptides and one BLyS polypeptide. Antibodies of the invention may be assayed for the ability to bind APRIL heterotrimers, where said heterotrimers consist of one APRIL polypeptide and two heterologous polypeptides, or alternatively, two APRIL polypeptides and one heterologous polypeptide.

Assays for the ability of the antibodies of the invention to immunospecifically bind APRIL or a fragment of APRIL may be performed in solution (e.g., Houghten, Bio/Techniques 13:412–421(1992)), on beads (e.g., Lam, Nature 354:82–84 (1991)), on chips (e.g., Fodor, Nature 364:555–556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., Proc. Natl. Acad. Sci. USA 89:1865–1869 (1992)) or on phage (e.g., Scott and Smith, Science 249:386–390 (1990); Devlin, Science 249:404–406 (1990); Cwirla et al., Proc. Natl. Acad. Sci. USA 87:6378–6382 (1990); and Felici, J. Mol. Biol. 222:301–310 (1991)) (each of these references is incorporated herein in its entirety by reference). Antibodies that have been identified to immunospecifically bind to APRIL or a fragment of APRIL can then be assayed for their specificity and affinity for APRIL or a fragment of APRIL using or routinely modifying techniques described herein or otherwise known in the art.

The antibodies of the invention may be assayed for immunospecific binding to APRIL and cross-reactivity with other antigens by any method known in the art. In particular, the ability of an antibody to immunospecifically bind to the soluble form or membrane-bound form of APRIL and the specificity of the antibody, fragment, or variant for APRIL polypeptide from a particular species (e.g., murine, monkey or human, preferably human) may be determined using or routinely modifying techniques described herein or otherwise known in the art.

Immunoassays which can be used to analyze immunospecific binding and cross-reactivity include, but are not limited to, competitive and non-competitive assay systems using techniques such as western blots, radioimmunoassays, such as ELISA (enzyme linked immunosorbent assay; e.g., see Example 2), "sandwich" immunoassays, BIAcore analysis, fluorescence activated cell sorter (FACS) or flow cytometry analysis, immunofluorescence, immunocytochemistry, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trayslol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40 degrees C., adding protein A and/or protein G sepharose beads to the cell lysate, incubating for about an hour or more at 40 degrees C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96-well microtiter plate with the antigen, washing away antigen that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the antigen coating the well. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, the detectable molecule could be the antigen conjugated to a detectable compound such as an enzymatic substrate (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody (including an scFv or other molecule comprising, or alternatively consisting of, antibody fragments or variants thereof) to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of the present invention for APRIL and the binding off-rates can be determined from the data by Scatchard plot analysis. Competition with a second antibody can also be determined using radioimmunoassays. In this case, APRIL is incubated with an antibody of the present invention conjugated to a labeled compound (e.g., $^{3}H$ or $^{125}I$) in the presence of increasing amounts of an unlabeled second anti-APRIL antibody.

In a preferred embodiment, BIAcore kinetic analysis is used to determine the binding on and off rates of antibodies (including an scFv or other molecule comprising, or alternatively consisting of, antibody fragments or variants thereof) to APRIL, or fragments of APRIL. BIAcore kinetic analysis comprises analyzing the binding and dissociation of APRIL from chips with immobilized antibodies on their surface.

The antibodies of the invention (including scFvs and other molecules comprising, or alternatively consisting of, antibody fragments or variants thereof) can also be assayed for their ability to inhibit, increase, or not significantly alter, the binding of APRIL to an APRIL receptor (e.g., TACI and BCMA) using techniques known to those of skill in the art. For example, cells expressing a receptor for APRIL (e.g., Raji Burkitt's lymphoma cells, and A20 B cell lymphoma cells as well as K562 erythroid leukemia cells (Yu et al., 2000 supra)) can be contacted with APRIL in the presence or absence of an antibody, and the ability of the antibody to inhibit, increase, or not significantly alter, APRIL binding to the cells can be measured. APRIL binding to cells can be measured by, for example, flow cytometry or a scintillation assay. APRIL or the antibody can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between APRIL and an APRIL receptor and/or APRIL and an antibody of the invention. Alternatively, the ability of antibodies of the invention to inhibit, increase, or not significantly alter, APRIL binding to an APRIL receptor can be determined in cell-free assays. For example, native or recombinant APRIL (e.g., that having the amino acid sequence of amino acids 88–233 of SEQ ID NO:36) or a fragment thereof can be contacted with an antibody and the ability of the antibody to inhibit, increase, or not significantly alter, APRIL from binding to an APRIL receptor can be determined. Preferably, the antibody is immobilized on a solid support and APRIL or an APRIL fragment is labeled with a detectable compound. Alternatively, APRIL or an APRIL fragment is immobilized on a solid support and the antibody is labeled with a detectable compound. APRIL may be partially or completely purified (e.g., partially or completely free of other polypeptides) or part of a cell lysate. Further, the APRIL polypeptide may be a fusion protein comprising APRIL or a biologically active portion thereof and a domain such as an Immunoglobulin Fc or glutathionine-S-transferase. For example, amino acid residues 1–154 of TACI (GenBank accession number AAC51790), or 1–48 of BCMA (GenBank accession number NP_001183) may be fused to the Fc region of an IgG molecule and used in a cell free assay to determine the ability of antibodies of the invention to inhibit, increase, or not significantly alter, APRIL binding to an APRIL receptor. Alternatively, APRIL can be biotinylated using techniques well known to those of skill in the art (e.g., biotinylation kit, Pierce Chemicals; Rockford, Ill.).

The antibodies of the invention (including scFvs or other molecules comprising, or alternatively consisting of, antibody fragments or variants thereof) can also be assayed for their ability to inhibit, stimulate, or not significantly alter, APRIL-induced B-cell proliferation using techniques known to those of skill in the art. For example, B-cell proliferation can be assayed by $^{3}H$-thymidine incorporation assays and trypan blue cell counts (see, e.g., Moore et al., Science 285: 260–263 (1999)). Further, the antibodies of the invention, or fragments or variants thereof, can be assayed for their ability to block, stimulate, or not significantly alter, APRIL-induced activation of cellular signaling molecules and transcription factors such as calcium-modulator and cyclophilin ligand ("CAML"), calcineurin, nuclear factor of activated T cells transcription factor ("NF-AT"), nuclear factor-kappa B ("NF-kappa B"), and AP-1 using techniques known to those of skill in the art (see, e.g., von Bulow and Bram, Science 278:138–141(1997)). For example, NF-AT activity can be determined by electromobility gel shift assays, by detecting the expression of a protein known to be regulated by NF-AT (e.g., IL-2 expression), by detecting the induction of a reporter gene (e.g., an NF-AT regulatory element operably linked to a nucleic acid encoding a detectable marker such as luciferase, beta-galactosidase or chloramphenicol acetyltransferase (CAT)), or by detecting a cellular response (e.g., cellular differentiation, or cell proliferation).

The antibodies of the invention, or fragments or variants thereof can also be assayed for their ability to neutralize, enhance, or not significantly alter, APRIL activity. For example, antibodies or fragments or variants thereof, may be routinely tested for their ability to inhibit APRIL from binding to cells expressing the receptor for APRIL (see Example 3, infra).

Characterization of Antibodies that Immunospecifically Bind to APRIL

Antibodies of the invention (including scFvs and other molecules comprising, or alternatively consisting of, antibody fragments or variants thereof) may be screened in a variety of assays to identify those antibodies that immunospecifically bind to a soluble form of APRIL. In one particular assay, antibodies that bind to a biotinylated soluble form of APRIL in solution are captured on streptavidin coated magnetic beads. This assay may be readily applied to identify antibodies of the invention that neutralize and/or bind to APRIL. Additionally, antibodies may be assayed in neutralization assays described herein or otherwise known in the art (see Example 3, infra).

For example, antibodies may be tested for their ability to inhibit soluble APRIL (e.g., biotinylated APRIL) from binding to cells bearing an APRIL receptor. In this assay, labeled soluble APRIL (e.g., biotinylated APRIL) is incubated with candidate anti-APRIL antibodies to allow for the formation of APRIL—anti-APRIL antibody complexes. Following incubation, an aliquot of the APRIL—anti-APRIL antibody sample is added to IM9 cells. The binding of soluble APRIL may be determined using techniques known in the art. For example, the binding of biotinylated APRIL to cells bearing an APRIL receptor cells may be detected using a fluorimeter following the addition of streptavidin-delfia. Biotinylated APRIL, if it is not bound by antibodies that neutralize APRIL, binds to the cells and is detected. Thus, an antibody that decreases the amount of bio-APRIL that binds to cells bearing an APRIL receptor (relative to a control sample in which the APRIL had been preincubated with an irrelevant antibody or no antibody at all) is identified as one that binds to and neutralizes the soluble form of APRIL.

In another assay, antibodies are screened using ELISAs for those antibodies that bind to biotinylated soluble APRIL, but do not bind membrane-bound APRIL, such as, for example, APRIL on membranes from APRIL-expressing cells. In these assays, soluble APRIL and membrane-bound APRIL are incubated in separate samples with the same antibodies and those antibodies that bind to the soluble APRIL, but not membrane-bound APRIL, are captured and identified.

Antibodies of the invention (including scFvs and other molecules comprising, or alternatively consisting of, antibody fragments or variants thereof) may be tested to identify those antibodies that do not cross-react with BLyS (SEQ ID NO:38), endokine-alpha (SEQ ID NO:39), VEGI (SEQ ID NO:40), TRAIL (SEQ ID NO:41), TNF-alpha (SEQ ID NO:42), TNF-beta (SEQ ID NO:43), Fas-L (SEQ ID NO:44), LIGHT(SEQ ID NO:45), TACI (SEQ ID NO:46), BCMA (SEQ ID NO:47), BSA and PBS (e.g., see Example 2). Antibodies may also be tested for their affinity for APRIL using, for example, BIAcore analysis. Antibodies may also be tested for their ability to stimulate, inhibit, or not alter, APRIL-induced immunoglobulin production and/or B-cell proliferation, differentiation and/or survival using techniques known to those of skill in the art. For example, human B-cells, APRIL and antibodies may be incubated together in 96 well plates and $^3$H-thymidine incorporation may be measured using a scintillation counter.

Antibody Conjugates

The present invention encompasses antibodies (including scFvs and other molecules comprising, or alternatively consisting of, antibody fragments or variants thereof), recombinantly fused or chemically conjugated (including both covalent and non-covalent conjugations) to a heterologous polypeptide ,(or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies of the invention may be used to target heterologous polypeptides to particular cell types (e.g., cells of monocytic lineage and B-cells), either in vitro or in vivo, by fusing or conjugating the heterologous polypeptides to antibodies of the invention that are specific for particular cell surface antigens (e.g., membrane-bound APRIL on cells of monocytic lineage) or which bind antigens that bind particular cell surface receptors (e.g., TACI and/or BCMA located on B cells). Antibodies fused or conjugated to heterologous polypeptides may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452 (1991), which are incorporated by reference in their entireties.

In one embodiment, a fusion protein comprises a polypeptide having an amino acid sequence of any one of the VH domains referred to in Table 1, and a heterologous polypeptide. In another embodiment, a fusion protein comprises a polypeptide having the amino acid sequence of any one of the VH CDR1s referred to in Table 1, and a heterologous polypeptide. In another embodiment, a fusion protein comprises a polypeptide having the amino acid sequence of any one of the VH CDR2s referred to in Table 1, and a heterologous polypeptide. In a preferred embodiment, a fusion protein comprises a polypeptide having the amino acid sequence of any one of the VH CDR3s referred to in Table 1 (i.e., SEQ ID NOs:25–34), and a heterologous polypeptide.

In another embodiment, a fusion protein comprises a polypeptide having the amino acid sequence of any one of the VL domains referred to in Table 1, and a heterologous polypeptide. In another embodiment, a fusion protein comprises a polypeptide having the amino acid sequence of any one of the VL CDR1s referred to in Table 1, and a heterologous polypeptide. In yet another embodiment, a fusion protein comprises a polypeptide having the amino acid sequence of any one of the VL CDR2s referred to in Table 1, and a heterologous polypeptide. In a preferred embodiment, a fusion protein comprises a polypeptide having the amino acid sequence of any one of the VL CDR3s referred to in Table 1, and a heterologous polypeptide.

In another embodiment, a fusion protein comprises a polypeptide having the amino acid sequence of any one of the VH domains referred to in Table 1, and one or more VL domains referred to in Table 1, and a heterologous polypeptide. In another embodiment, a fusion protein of the present invention comprises a polypeptide having the amino acid sequence of any one of the VH CDRs referred to in Table 1, and any one of the VL CDRs referred to in Table 1, and a heterologous polypeptide.

The present invention further includes compositions comprising, or alternatively consisting of, heterologous polypeptides fused or conjugated to antibody fragments. For example, the heterologous polypeptides may be fused or conjugated to a Fab fragment, Fd fragment, Fv fragment, F(ab)$_2$ fragment, or a portion thereof. Methods for fusing or conjugating polypeptides to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88: 10535–10539 (1991); Zheng et al., J. Immunol. 154:5590–5600 (1995); and Vil et al., Proc. Natl. Acad. Sci. USA 89:11337–11341 (1992) (said references incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including scFvs and other molecules comprising, or alternatively consisting of, antibody fragments or variants thereof), such methods can be used to generate antibodies with altered activity (e.g., antibodies with higher affinities and lower dissociation rates). See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, polynucleotides encoding antibodies of the invention may be altered by being subjected to random mutagenesis by error-prone PCR, random nucleotide insertion or other methods prior to recombination. In another embodiment, one or more portions of a polynucleotide encoding an antibody which portions immunospecifically bind to APRIL may be recombined with one or more components, motifs, sections, parts, domains, fragments, etc. of one or more heterologous molecules.

Moreover, the antibodies of the present invention (including scFvs and other molecules comprising, or alternatively consisting of, antibody fragments or variants thereof) can be fused to marker sequences, such as a polypeptides to facilitate purification. In preferred embodiments, the marker amino acid sequence is a hexa-histidine polypeptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., Cell 37:767 (1984)) and the "flag" tag (DYKDDDDK, (SEQ ID NO:48) Stratagene, La Jolla, Calif.).

The present invention further encompasses antibodies (including scFvs and other molecules comprising, or alternatively consisting of, antibody fragments or variants thereof), conjugated to a diagnostic or therapeutic agent. The antibodies can be used diagnostically to, for example, monitor or prognose the development or progression of a tumor as part of a clinical testing procedure to, e.g., determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include, but are not limited to, horseradish peroxidase, alkaline phosphatase, beta-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin; and examples of suitable radioactive material include, but are not limited to, iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin.

Furthermore, an antibody of the invention (including scFvs and other molecules comprising, or alternatively consisting of, antibody fragments or variants thereof) may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi, or other radioisotopes such as, for example, $^{211}$At, $^{103}$Pd, $^{133}$Xe, $^{131}$I, $^{125}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody of the invention (including scFvs and other molecules comprising, or alternatively consisting of, antibody fragments or variants thereof) is attached to macrocyclic chelators useful for conjugating radiometal ions, including but not limited to, $^{177}$Lu, $^{90}$Y, $^{166}$Ho, $^{111}$In, and $^{153}$Sm, to polypeptides. In a preferred embodiment, the radiometal ion associated with an antibody of the invention is $^{111}$In. In another preferred embodiment, the radiometal ion associated with the macrocyclic chelator attached to an antibody of the invention is $^{90}$Y. In specific embodiments, the macrocyclic chelator is 1,4,7,10-tetraazacyclododecane-N,N',N",N'''-tetraacetic acid (DOTA). In other specific embodiments, the DOTA is attached to an antibody of the invention or fragment thereof via a linker molecule. Examples of linker molecules useful for conjugating DOTA to a polypeptide are commonly known in the art—see, for example, DeNardo et al., Clin Cancer Res. 4(10):2483–90 (1998); Peterson et al., Bioconjug. Chem. 10(4):553–7 (1999); and Zimmerman et al, Nucl. Med. Biol. 26(8):943–50 (1999) which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

A cytotoxin or cytotoxic agent includes any agent that is detrimental to cells and includes such molecules as small molecule toxins and enzymatically active toxins of bacterial, fungal, plant, or animal origin, or fragments thereof. Examples include paclitaxol, cytochalasin B, gramicidin D, ethidium bromide, emetine, mitomycin, etoposide (VP-16), tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) (cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), anti-mitotic agents (e.g., vincristine and vinblastine), improsulfan, piposulfan, benzodopa, carboquone, meturedopa, uredopa, altretamine, triethylenemelamine, trietylenephosphoramide, triethylenethiophosphaoramide trimethylolomelamine, chlornaphazine, cholophosphamide, estramustine, ifosfamide, novembichin, phenesterine, prednimustine, trofosfamide, uracil mustard, chlorozotocin, fotemustine, nimustine, ranimustine, aclacinomysins, azaserine, cactinomycin, calichearnicin, carabicin, carminomycin, carzinophilin, chromomycins, detorubicin, 6-diazo-5-oxo-L-norleucine, epirubicin, esorubicin, idarubicin, marcellomycin, mycophenolic acid, nogalamycin, olivomycins, peplomycin, potfiromycin, quelamycin, rodorubicin, streptonigrin, tubercidin, ubenimex, zinostatin, zorubicin, denopterin, pteropterin, trimetrexate, fludarabine, thiamiprine, ancitabine, azacitidine, 6-azauridine, carmofur, dideoxyuridine, doxifluridine, enocitabine, floxuridine, 5-FU, calusterone, dromostanolone propionate, epitiostanol, mepitiostane, testolactone, aminoglutethimide, mitotane, trilostane, frolinic acid, aceglatone, aldophosphamide glycoside, aminolevulinic acid, amsacrine, bestrabucil, bisantrene, edatraxate, defofamine, dernecolcine, diaziquone, elformithine, elliptinium acetate, etoglucid, gallium nitrate, hydroxyurea, lentinan, lonidamine, mitoguazone, mopidamol, nitracrine, pentostatin, phenamet, pirarubicin, podophyllinic acid, 2-ethylhydrazide, procarbazine, PSKO, razoxane, sizofiran, spirogermanium, tenuazonic acid, triaziquone, 2,2',2"-trichlorotriethylamine, urethan, vindesine, dacarbazine, mannomustine, mitobronitol, mitolactol, pipobroman, gacytosine, arabinoside ("Ara-C"), taxoids, e.g. paclitaxel (TAXOL", Bristol-Myers Squibb Oncology, Princeton, N.J.) doxetaxel (TAXOTERE", Rh6ne-Poulenc Rorer, Antony, France), gemcitabine, ifosfamide, vinorelbine, navelbine, novantrone, teniposide, aminopterin, xeloda, ibandronate, CPT-I 1, topoisomerase inhibitor RFS 2000, difluoromethylornithine (DMFO), retinoic acid, esperamicins, capecitabine, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4 hydroxytamoxifen, trioxifene, keoxifene, LY 117018, onapristone, toremifene (Fareston), and anti-androgens such as flutamide, nilutamide, bicalutamide, leuprolide, and goserelin, and pharmaceutically acceptable salts, acids or derivatives of any of the above.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The antibodies of the invention which are conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, but are not limited to, for example, a toxin such as abrin, ricin A, alpha toxin, pseudomonas exotoxin, or diphtheria toxin, saporin, momordin, gelonin, pokeweed antiviral protein, alpha-sarcin and cholera toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/33899), AIM II (see, International Publication No. WO 97/34911), Fas Ligand (Takahashi et al., Int. Immunol., 6:1567–1574 (1994)), VEGI (see, International Publication No. WO 99/23105), a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Antibodies of the invention (including scFvs and other molecules comprising, or alternatively consisting of, antibody fragments or variants thereof), may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating a therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody of the invention can be conjugated to a second antibody to form an antibody heteroconjugate as described by Segal in U.S. Pat. No. 4,676,980, which is incorporated herein by reference in its entirety.

An antibody of the invention (including an scFv or and other molecule comprising, or alternatively consisting of, an antibody fragment or variant thereof), with or without a therapeutic moiety conjugated to it, administered alone or in combination with cytotoxic factor(s) and/or cytokine(s) can be used as a therapeutic.

Use of Antibodies for Epitope Mapping

The present invention provides antibodies (including scFvs and other molecules comprising, or alternatively consisting of, antibody fragments or variants thereof) that can be used to identify epitopes of APRIL. In particular, the antibodies of the present invention can be used to identify epitopes of human APRIL (SEQ ID NOs:36 and/or 37) or APRIL expressed on human monocytes using techniques described herein or otherwise known in the art. Antibodies of the invention may be used to identify exposed epitopes of APRIL polypeptides in functional heterotrimeric APRIL complexes. Fragments which function as epitopes may be produced by any conventional means. (See, e.g., Houghten, Proc. Natl. Acad. Sci. USA 82:5131–5135 (1985), further described in U.S. Pat. No. 4,631,211.)

Diagnostic Uses of Antibodies

Labeled antibodies of the invention (including molecules comprising, or alternatively consisting of, antibody fragments or variants thereof), which specifically bind to APRIL, can be used for diagnostic purposes to detect, diagnose, prognose, or monitor diseases and/or disorders associated with the aberrant expression and/or activity of APRIL or APRIL receptor. The invention provides for the detection of aberrant expression of APRIL comprising: (a) assaying the expression of APRIL in a biological sample from an individual using one or more antibodies of the invention that immunospecifically binds to APRIL; and (b) comparing the level of APRIL with a standard level of APRIL, e.g., in normal biological samples, whereby an increase or decrease in the assayed level of APRIL compared to the standard level of APRIL is indicative of aberrant expression.

By "biological sample" is intended any fluids and/or cells obtained from an individual, body fluid, body tissue, body cell, cell line, tissue culture, or other source which may contain APRIL protein or mRNA. Body fluids include, but are not limited to, sera, plasma, urine, synovial fluid, spinal fluid, saliva, and mucous. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

The invention also provides a method for the detection of aberrant expression of APRIL receptor comprising (a) assaying the expression of APRIL receptor in a biological sample from an individual using one or more antibodies or fragments or variants thereof that immunospecifically binds only to soluble APRIL, but does not inhibit APRIL/APRIL receptor binding (such an antibody, by way of an example that is not to be construed as limiting, would be one that is able to capture a biotinylated APRIL from solution but that would not prevent APRIL from binding to APRIL receptor expressing cells) and (b) comparing the level of APRIL receptor with a standard level of APRIL receptor, e.g., in normal tissue or cell samples, whereby an increase or decrease in the assayed level of APRIL receptor compared to the standard level of APRIL receptor is indicative of aberrant expression.

Antibodies of the invention (including molecules comprising, or alternatively consisting of, antibody fragments or variants thereof), which specifically bind to APRIL, can be used for diagnostic purposes to detect, diagnose, prognose, or monitor autoimmune disorders and/or immunodeficiencies, and/or proliferative disorders, and/or diseases or conditions associated therewith. The invention provides for the detection of aberrant expression of APRIL comprising: (a) assaying the expression of APRIL in a biological sample from an individual using one or more antibodies of the invention that immunospecifically binds to APRIL; and (b) comparing the level of APRIL with a standard level of APRIL, e.g., in normal biological samples, whereby an increase or decrease in the assayed level of APRIL compared to the standard level of APRIL is indicative of an autoimmune disorder or disease, and/or an immunodeficiency, and/or a proliferative disorder or disease. In specific embodiments, an increase in the assayed level of APRIL is indicative of an autoimmune disorder or disease. In other specific embodiments, a decrease in the assayed level of APRIL is indicative of an immunodeficiency. In other specific embodiments, an increase or a decrease in the assayed level of APRIL is indicative of a proliferative disorder.

Antibodies of the invention (including molecules comprising, or alternatively consisting of, antibody fragments or variants thereof) which specifically bind to APRIL but, do not inhibit APRIL/APRIL receptor binding can be used for diagnostic purposes to detect, diagnose, prognose, or monitor autoimmune disorders and/or immunodeficiencies and/or proliferative disorders, and/or diseases or conditions associated therewith. The invention provides for the detection of aberrant expression of APRIL receptor comprising: (a) assaying the expression of APRIL receptor in a biological sample from an individual using one or more antibodies of the invention that immunospecifically binds to APRIL; and (b) comparing the level of APRIL receptor with a standard level of APRIL receptor, e.g., in normal biological samples, whereby an increase or decrease in the assayed level of APRIL receptor compared to the standard level of APRIL receptor is indicative of an autoimmune disorder or disease and/or an immunodeficiency and/or a proliferative disorder. In specific embodiments, an increase in the assayed level of APRIL receptor is indicative of an autoimmune disorder or disease. In other specific embodiments, a decrease in the assayed level of APRIL receptor is indicative of an immunodeficiency. In other specific embodiments, an increase or a decrease in the assayed level of APRIL is indicative of a proliferative disorder.

Autoimmune and inflammatory disorders, diseases, or conditions that may be detected, diagnosed, prognosed, or monitored using the antibodies of the invention include, but are not limited to, autoimmune hemolytic anemia (including, but not limited to cryoglobinemia or Coombs positive anemia), autoimmune neonatal thrombocytopenia, idiopathic thrombocytopenic purpura, autoimmune thrombocytopenic purpura, autoimmune neutropenia, autoimmunocytopenia, hemolytic anemia, antiphospholipid syndrome, dermatitis (e.g. atopic dermatitis), gluten-sensitive enteropathy, allergic encephalomyelitis, myocarditis, relapsing polychondritis, rheumatic heart disease, glomerulonephritis (e.g., primary glomerulonephritis and IgA nephropathy), Multiple Sclerosis, Neuritis, Uveitis Ophthalmia, Polyendocrinopathies, Purpura (e.g., Henloch-Schoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, diabetes mellitus (e.g. Type I diabetes mellitus or insulin dependent diabetes mellitus), juvenile onset diabetes, autoimmune inflammatory eye, autoimmune thyroiditis, hypothyroidism (i.e., Hashimoto's thyroiditis), systemic lupus erythematosus, discoid lupus, Goodpasture's syndrome, Pemphigus, Receptor autoimmunities such as, for example, (a) Graves' Disease , (b) Myasthenia Gravis, and (c) insulin resistance, rheumatoid arthritis, scleroderma with anti-collagen antibodies, mixed connective tissue disease, polymyositis/dermatomyositis, pernicious anemia (Addison's disease), idiopathic Addison's disease, infertility, bullous pemphigoid, Sjögren's syndrome, adrenergic drug resistance (including adrenergic drug resistance with asthma or cystic fibrosis), chronic active hepatitis, primary biliary cirrhosis, other endocrine gland failure, vitiligo, vasculitis, post-MI cardiotomy syndrome, urticaria, asthma, inflammatory myopathies, and other inflammatory, granulomatous, degenerative, and atrophic disorders, and other disorders such as inflammatory skin diseases including psoriasis and sclerosis, responses associated with inflammatory bowel disease (such as Crohn's disease and ulcerative colitis), respiratory distress syndrome (including adult respiratory distress syndrome, ARDS), meningitis, encephalitis, colitis, allergic conditions such as eczema and other conditions involving infiltration of T cells and chronic inflammatory responses, atherosclerosis, leukocyte adhesion-deficiency, Reynaud's syndrome, and immune responses associated with acute and delayed hypersensitivity mediated by cytokines and T-lymphocytes typically found in tuberculosis, sarcoidosis, granulomatosis and diseases involving leukocyte diapedesis, central nervous system (CNS) inflammatory disorder, multiple organ injury syndrome, antigen-antibody complex mediated diseases, anti-glomerular basement membrane disease, Lambert-Eaton myasthenic syndrome, Bechet's disease, giant cell arteritis, immune complex nephritis, IgM polyneuropathies or autoimmune thrombocytopenia etc.

In additional embodiments, antibodies of the invention which specifically bind to APRIL can be used for diagnostic purposes to detect, diagnose, prognose, or monitor an immune-based rheumatologic disease, (e.g., SLE, rheumatoid arthritis, CREST syndrome (a variant of scleroderma characterized by calcinosis, Raynaud's phenomenon, esophageal motility disorders, sclerodactyly, and telangiectasia.), Seronegative spondyloarthropathy (SpA), Polymyositis/dermatomyositis, Microscopic polyangiitis, Hepatitis C-associated arthritis, Takayasu's arteritis, and undifferentiated connective tissue disorder). The invention provides for the detection of aberrant expression of APRIL comprising: (a) assaying the expression of APRIL in a biological sample (e.g., serum and synovial fluid) of an individual using one or more antibodies of the invention that immunospecifically binds to APRIL; and (b) comparing the level of APRIL with a standard level of APRIL, e.g., in normal biological samples, whereby an increase in the assayed level of APRIL compared to the standard level of APRIL is indicative of monitor an immune-based rheumatologic disease.

In further specific embodiments, serum levels of APRIL (determined using one or more antibodies of the present invention) in individuals diagnosed with an immune based rheumatologic disease (e.g., SLE, rheumatoid arthritis, CREST syndrome (a variant of scleroderma characterized by calcinosis, Raynaud's phenomenon, esophageal motility disorders, sclerodactyly, and telangiectasia.), seronegative spondyloarthropathy (SpA), polymyositis/dermatomyositis, microscopic polyangiitis, hepatitis C-associated arthritis, Takayasu's arteritis, and undifferentiated connective tissue disorder) may be used to determine, diagnose, prognose, or monitor the severity of certain aspects or symptoms of the disease, such as nephrotic-range proteinuria.

In specific embodiments, antibodies of the invention which specifically bind to APRIL can be used for diagnostic purposes to detect, diagnose, prognose, or monitor Systemic Lupus Erythematosus or conditions associated therewith. The invention provides for the detection of aberrant expression of APRIL comprising: (a) assaying the expression of APRIL in a biological sample of an individual using one or more antibodies of the invention that immunospecifically binds to APRIL; and (b) comparing the level of APRIL with a standard level of APRIL, e.g., in normal biological samples, whereby an increase in the assayed level of APRIL compared to the standard level of APRIL is indicative of SLE.

In additional embodiments, antibodies of the invention which specifically bind to APRIL can be used for diagnostic purposes to detect, diagnose, prognose, or monitor Rheumatoid Arthritis. The invention provides for the detection of aberrant expression of APRIL comprising: (a) assaying the expression of APRIL in a biological sample (e.g., serum and synovial fluid) of an individual using one or more antibodies of the invention that immunospecifically binds to APRIL; and (b) comparing the level of APRIL with a standard level of APRIL, e.g., in normal biological samples, whereby an increase in the assayed level of APRIL compared to the standard level of APRIL is indicative of Rheumatoid arthritis.

In specific embodiments, the invention provides a diagnostic assay for diagnosing or prognosing Idiopathic Thrombocytopenic Purpura, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without Idiopathic Thrombocytopenic Purpura, whereby an increase in the assayed APRIL level compared to the standard level of APRIL is indicative of Idiopathic Thrombocytopenic Purpura.

In specific embodiments, the invention provides a diagnostic assay for diagnosing or prognosing Sjögren's syndrome, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without Sjögren's syndrome, whereby an increase in the assayed APRIL level compared to the standard level of APRIL is indicative of Sjögren's syndrome.

In specific embodiments, the invention provides a diagnostic assay for diagnosing or prognosing Myasthenia gravis, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without Myasthenia gravis, whereby an increase in the assayed APRIL level compared to the standard level of APRIL is indicative of Myasthenia gravis.

In specific embodiments, the invention provides a diagnostic assay for diagnosing or prognosing IgA nephropathy, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without IgA nephropathy, whereby an increase in the assayed APRIL level compared to the standard level of APRIL is indicative of IgA nephropathy.

In specific embodiments, the invention provides a diagnostic assay for diagnosing or prognosing hemolytic anemia, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without hemolytic anemia, whereby an increase in the assayed APRIL level compared to the standard level of APRIL is indicative of hemolytic anemia.

In specific embodiments, the invention provides a diagnostic assay for diagnosing or prognosing thyroiditis, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without thyroiditis, whereby an increase or decrease in the assayed APRIL level compared to the standard level of APRIL is indicative of thyroiditis.

In specific embodiments, the invention provides a diagnostic assay for diagnosing or prognosing Goodpasture's syndrome, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without Goodpasture's syndrome, whereby an increase or decrease in the assayed APRIL level compared to the standard level of APRIL is indicative of Goodpasture's syndrome.

In specific embodiments, the invention provides a diagnostic assay for diagnosing or prognosing Multiple sclerosis, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without Multiple sclerosis, whereby an increase or decrease in the assayed APRIL level compared to the standard level of APRIL is indicative of Multiple sclerosis.

Immunodeficiencies that may be detected, diagnosed, prognosed, or monitored using the antibodies of the invention include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

In specific embodiments, the present invention encompasses methods and compositions for detecting, diagnosing, prognosing and/or monitoring diseases or disorders associated with hypergammaglobulinemia (e.g., AIDS, autoimmune diseases, and some immunodeficiencies). In other specific embodiments, the present invention encompasses methods and compositions for detecting, diagnosing and/or prognosing diseases or disorders associated with hypogammaglobulinemia (e.g., an immunodeficiency).

In specific embodiments, the invention provides a diagnostic assay for diagnosing or prognosing Common Variable Immunodeficiency (CVID), comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without CVID, whereby a decrease in the assayed APRIL level compared to the standard level of APRIL is indicative of CVID.

In specific embodiments, the invention provides a diagnostic assay for diagnosing or prognosing Selective IgA deficiency, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without Selective IgA deficiency, whereby a decrease in the assayed APRIL level compared to the standard level of APRIL is indicative of Selective IgA deficiency.

Proliferative disorders, diseases, or conditions that may be detected, diagnosed, prognosed, or monitored using the antibodies of the invention include, but are not limited to, Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia and Wilms' Tumor. Premalignant disorders which may progress to malignancy, that may be detected, diagnosed, prognosed, or monitored using the antibodies of the invention include, but are not limited to, hyperplasia (a form of controlled cell proliferation, involving an increase in cell number in a tissue or organ, without significant alteration in structure or function, including, but not limited to, angiofollicular mediastinal lymph node hyperplasia, angiolymphoid hyperplasia with eosinophilia, a typical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia), metaplasia (a form of controlled cell growth in which one type of adult or fully differentiated cell substitutes for another type of adult cell, including, but not limited to, agnogenic myeloid metaplasia, apocrine metaplasia, a typical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia), and dysplasia (which is frequently a forerunner of cancer and is found mainly in the epithelia, is the most disorderly form of non-neoplastic cell growth, involving a loss in individual cell uniformity and in the architectural orientation of cells which often have abnormally large, deeply stained nuclei, and exhibit pleomorphism, including, but not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia).

The invention provides a diagnostic assay for diagnosing or prognosing a disease or disorder, comprising: (a) assaying for the level of APRIL receptor in cells or a tissue sample of an individual using one or more antibodies of the invention that immunospecifically binds only to soluble APRIL, but does not neutralize APRIL/APRIL receptor binding; and (b) comparing the level of APRIL receptor with a standard APRIL receptor level, e.g., in a tissue sample from a patient without the disease or disorder, whereby an increase or decrease in the assayed APRIL receptor level compared to the standard level of APRIL receptor is indicative of a particular disease or disorder. With respect to cancer, the presence of a relatively high amount of APRIL receptor in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

The invention provides a diagnostic assay for diagnosing or prognosing a disease or disorder, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without the disease or disorder, whereby an increase or decrease in the assayed APRIL level compared to the standard level of APRIL is indicative of a particular disease or disorder. With respect to cancer, the presence of a relatively high amount of APRIL in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

In specific embodiments, the presence of a relatively high amount of membrane-bound APRIL in a biological sample is indicative of monocytic cell related leukemias or lymphomas, such as, for example acute myelogenous leukemia and/or the severity thereof.

In specific embodiments, the invention provides a diagnostic assay for diagnosing or prognosing Acute Myelogenous Leukemia, comprising: (a) assaying for the level of APRIL in a biological sample of an individual using one or more antibodies of the invention that immunospecifically bind to APRIL; and (b) comparing the level of APRIL with a standard APRIL level, e.g., in a biological sample from a patient without Acute Myelogenous Leukemia, whereby an increase in the assayed APRIL level compared to the standard level of APRIL is indicative of Acute Myelogenous leukemia.

In other specific embodiments, the presence of a relatively high amount of APRIL receptor in a biological sample (as determined using antibodies of the invention that bind to soluble APRIL, but do not inhibit APRIL/APRIL receptor binding) is indicative of B cell related leukemias or lymphomas (e.g., chronic lymphocytic leukemia, multiple myeloma, non-Hodgkin's lymphoma, and Hodgkin's disease), and/or the severity thereof.

In specific embodiments, the invention provides a diagnostic assay for diagnosing or prognosing Chronic Lymphocytic Leukemia, comprising: (a) assaying for the level of APRIL receptor in a biological sample of an individual using one or more antibodies of the invention that immunospecifically bind to APRIL; and (b) comparing the level of APRIL receptor with a standard APRIL receptor level, e.g., in a biological sample from a patient without Chronic Lymphocytic Leukemia, whereby an increase or decrease in the assayed APRIL receptor level compared to the standard level of APRIL receptor is indicative of Chronic Lymphocytic Leukemia.

In specific embodiments, the invention provides a diagnostic assay for diagnosing or prognosing Multiple Myeloma, comprising: (a) assaying for the level of APRIL receptor in a biological sample of an individual using one or more antibodies of the invention that immunospecifically bind to APRIL; and (b) comparing the level of APRIL receptor with a standard APRIL receptor level, e.g., in a biological sample from a patient without Multiple Myeloma, whereby an increase or decrease in the assayed APRIL receptor level compared to the standard level of APRIL receptor is indicative of Multiple Myeloma.

In specific embodiments, the invention provides a diagnostic assay for diagnosing or prognosing Non-Hodgkin's Lymphoma, comprising: (a) assaying for the level of APRIL receptor in a biological sample of an individual using one or more antibodies of the invention that immunospecifically bind to APRIL; and (b) comparing the level of APRIL receptor with a standard APRIL receptor level, e.g., in a biological sample from a patient without Non-Hodgkin's Lymphoma, whereby an increase or decrease in the assayed APRIL receptor level compared to the standard level of APRIL receptor is indicative of Non-Hodgkin's Lymphoma.

In specific embodiments, the invention provides a diagnostic assay for diagnosing or prognosing Hodgkin's disease, comprising: (a) assaying for the level of APRIL receptor in a biological sample of an individual using one or more antibodies of the invention that immunospecifically bind to APRIL; and (b) comparing the level of APRIL receptor with a standard APRIL receptor level, e.g., in a biological sample from a patient without Hodgkin's disease, whereby an increase or decrease in the assayed APRIL receptor level compared to the standard level of APRIL receptor is indicative of Hodgkin's disease.

In other specific embodiments, the presence of a relatively high amount of APRIL receptor in a biological sample (as determined using antibodies of the invention that bind to soluble APRIL, but do not inhibit APRIL/APRIL receptor binding) is indicative of T cell related leukemias or lymphomas, and/or the severity thereof.

In specific embodiments, the invention provides a diagnostic assay for diagnosing or prognosing T cell lymphoma/mycosis fungoides, comprising: (a) assaying for the level of APRIL receptor in a biological sample of an individual using one or more antibodies of the invention that immunospecifically bind to APRIL; and (b) comparing the level of APRIL receptor with a standard APRIL receptor level, e.g., in a biological sample from a patient without T cell lymphoma/mycosis fungoides, whereby an increase or decrease in the assayed APRIL receptor level compared to the standard level of APRIL receptor is indicative of T cell lymphoma/mycosis fungoides.

Antibodies of the invention (including molecules comprising, or alternatively consisting of, antibody fragments or variants thereof) can be used to assay protein levels in a biological sample using classical immunohistological methods as described herein or as known to those of skill in the art (e.g., see Jalkanen, et al., J. Cell. Biol. 101:976–985 (1985); Jalkanen, et al., J. Cell Biol. 105:3087–3096 (1987)). Other antibody-based methods useful for detecting protein gene expression include immunoassays, such as the enzyme linked immunosorbent assay (ELISA) and the radio-immunoassay (RIA). Suitable antibody assay labels are known in the art and include enzyme labels, such as, glucose oxidase, alkaline phosphatase, and horseradish peroxidase; radioisotopes, such as iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru; luminescent labels, such as luminol; and fluorescent labels, such as fluorescein and rhodamine, and biotin.

One aspect of the invention is the detection and diagnosis of a disease or disorder associated with aberrant expression of APRIL or APRIL receptor in an animal, preferably a mammal and most preferably a human. In one embodiment, diagnosis comprises: a) administering (for example, parenterally, subcutaneously, or intraperitoneally) to a subject an effective amount of a labeled antibody of the invention (including molecules comprising, or alternatively consisting of, antibody fragments or variants thereof) that immunospecifically binds to APRIL; b) waiting for a time interval following the administering for permitting the labeled antibody to preferentially concentrate at sites in the subject where APRIL is expressed (and for unbound labeled molecule to be cleared to background level); c) determining background level; and d) detecting the labeled antibody in the subject, such that detection of labeled antibody or fragment thereof above the background level and above or below the level observed in a person without the disease or disorder indicates that the subject has a particular disease or disorder associated with aberrant expression of APRIL or APRIL receptor. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disorder, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Immunophenotyping

The antibodies of the invention (including molecules comprising, or alternatively consisting of, antibody fragments or variants thereof) may be utilized for immunophenotyping of cell lines and biological samples by their APRIL expression or APRIL receptor expression. Various techniques can be utilized using antibodies, fragments, or variants of the invention to screen for cellular populations (i.e., immune cells, particularly monocytic cells or B-cells) expressing APRIL or APRIL receptor, and include magnetic separation using antibody-coated magnetic beads, "panning" with antibody attached to a solid matrix (i.e., plate), and flow cytometry (see, e.g., U.S. Pat. No. 5,985,660; and Morrison et al., Cell, 96:737–49 (1999)).

These techniques allow for the screening of particular populations of cells, such as might be found with hematological malignancies (i.e., minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

In one embodiment, antibodies of the invention (including molecules comprising, or alternatively consisting of, antibody fragments or variants thereof) are used to identify cells of monocytic or B cell origin.

Therapeutic Uses of Antibodies

The present invention is further directed to antibody-based therapies which involve administering antibodies of the invention (including molecules comprising, or alternatively consisting of, antibody fragments or variants thereof) to an animal, preferably a mammal, and most preferably a human, patient for treating one or more of the disclosed diseases, disorders, or conditions. Therapeutic compounds of the invention include, but are not limited to, antibodies of the invention and nucleic acids encoding antibodies (and anti-idiotypic antibodies) of the invention as described herein. The antibodies of the invention can be used to treat, prevent or ameliorate diseases, disorders or conditions associated with aberrant expression and/or activity of APRIL or APRIL receptor, including, but not limited to, any one or more of the diseases, disorders, or conditions described herein. The treatment and/or prevention of diseases, disorders, or conditions associated with aberrant APRIL expression and/or activity or aberrant APRIL receptor expression and/or activity includes, but is not limited to, alleviating symptoms associated with those diseases, disorders or conditions. Antibodies of the invention may be provided in pharmaceutically acceptable compositions as known in the art or as described herein.

Antibodies of the present invention (including molecules comprising, or alternatively consisting of, antibody fragments or variants thereof) that function as agonists or antagonists of APRIL, preferably of APRIL-induced signal transduction, can be administered to an animal to treat, prevent or ameliorate a disease or disorder associated with aberrant APRIL expression, lack of APRIL function, aberrant APRIL receptor expression, or lack of APRIL receptor function. For example, antibodies of the invention which disrupt the interaction between APRIL and its receptor may be administered to an animal to treat, prevent or ameliorate a disease or disorder associated with aberrant APRIL expression or function and/or aberrant APRIL receptor expression or function. Antibodies of the invention which do not prevent APRIL from binding its receptor but inhibit or down-regulate APRIL-induced signal transduction can be administered to an animal to treat, prevent or ameliorate a disease or disorder associated with aberrant APRIL expression or function and/or aberrant APRIL receptor expression or function. In particular, antibodies of the present invention which prevent APRIL-induced signal transduction by specifically recognizing the unbound APRIL, receptor-bound APRIL or both unbound and receptor-bound APRIL can be administered to an animal to treat, prevent or ameliorate a disease or disorder associated with aberrant APRIL expression or function and/or aberrant APRIL receptor expression or function. Antibodies of the invention which do not prevent APRIL from binding its receptor and do not inhibit or down-regulate APRIL-induced signal transduction can be conjugated to a cytotoxic agent and administered to an animal to treat, prevent or ameliorate a disease or disorder associated with aberrant proliferation of cells expressing APRIL receptors. The ability of an antibody of the invention to inhibit or down-regulate APRIL-induced signal transduction may be determined by techniques described herein or otherwise known in the art. For example, APRIL-induced receptor activation and the activation of signaling molecules can be determined by detecting the phosphorylation (e.g., tyrosine or serine/threonine) of the receptor or a signaling molecule by immunoprecipitation followed by western blot analysis (for example, as described herein).

In a specific embodiment, an antibody of the present invention (including molecules comprising, or alternatively consisting of, antibody fragments or variants thereof) that inhibits or down-regulates APRIL activity by at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to APRIL activity in absence of the antibody is administered to an animal to treat, prevent or ameliorate a disease or disorder associated with aberrant APRIL expression or function and/or APRIL receptor expression or function. In another embodiment, a combination of antibodies, a combination of antibody fragments, a combination of antibody variants, or a combination of antibodies, antibody fragments, and/or variants that inhibit or down-regulate APRIL activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to APRIL activity in absence of said antibodies, antibody fragments, and/or antibody variants are administered to an animal to treat, prevent or ameliorate a disease or disorder associated with aberrant APRIL expression or function and/or aberrant APRIL receptor expression or function.

Further, antibodies of the present invention (including molecules comprising, or alternatively consisting of, antibody fragments or variants thereof) which activate APRIL-induced signal transduction can be administered to an animal to treat, prevent or ameliorate a disease or disorder associated with aberrant APRIL expression or function and/or aberrant APRIL receptor expression or function. These antibodies may potentiate or activate all or a subset of the biological activities of APRIL-mediated receptor activation, for example, by inducing multimerization of APRIL and/or multimerization of the receptor. The antibodies of the invention may be administered with or without being pre-complexed with APRIL. In a specific embodiment, an antibody of the present invention that increases APRIL activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% relative to APRIL activity in absence of the antibody is administered to an animal to treat, prevent or ameliorate a disease or disorder associated with aberrant APRIL expression or function and/or aberrant APRIL receptor expression or function. In another embodiment, a combination of antibodies, a combination of antibody fragments, a combination of antibody variants, or a combination of antibodies, antibody fragments and/or antibody variants that increase APRIL activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% relative to APRIL activity in absence of the said antibodies or antibody fragments and/or antibody variants is administered to an animal to treat, prevent or ameliorate a disease or disorder associated with aberrant APRIL expression or lack of APRIL function or aberrant APRIL receptor expression or lack of APRIL receptor function.

In a further specific embodiment, an antibody of the present invention (including molecules comprising, or alternatively consisting of, antibody fragments or variants thereof) that does not inhibit or down-regulate APRIL activity, relative to APRIL activity in the absence of the antibody, is administered to an animal to treat, prevent or ameliorate a disease or disorder associated with aberrant APRIL expression, excessive APRIL function, aberrant APRIL receptor expression, or excessive APRIL receptor function. In another embodiment, a combination of antibodies, a combination of antibody fragments, a combination of antibody variants, or a combination of antibodies, antibody fragments, and/or variants that do not inhibit or down-regulate APRIL, relative to APRIL activity in absence of said antibodies, antibody fragments, and/or antibody variants, are administered to an animal to treat, prevent or ameliorate a disease or disorder associated with aberrant APRIL expression, excessive APRIL function, aberrant APRIL receptor expression, or excessive APRIL receptor function.

Further, antibodies of the present invention (including molecules comprising, or alternatively consisting of, antibody fragments or variants thereof) which do not activate APRIL-induced signal transduction can be administered to an animal to treat, prevent or ameliorate a disease or disorder associated with aberrant APRIL expression, lack of APRIL function, aberrant APRIL receptor expression, or lack of APRIL receptor function. The antibodies of the invention may be administered with or without being pre-complexed with APRIL. In a specific embodiment, an antibody of the present invention that does not increase APRIL activity, relative to APRIL activity in absence of the antibody, is administered to an animal to treat, prevent or ameliorate a disease or disorder associated with aberrant APRIL expression, lack of APRIL function, aberrant APRIL receptor expression, or lack of APRIL receptor function. In another embodiment, a combination of antibodies, a combination of antibody fragments, a combination of antibody variants, or a combination of antibodies, antibody fragments and/or antibody variants that do not increase APRIL activity, relative to APRIL activity in absence of the said antibodies or antibody fragments and/or antibody variants, is administered to an animal to treat, prevent or ameliorate a disease or disorder associated with aberrant APRIL expression or lack of APRIL function or aberrant APRIL receptor expression or lack of APRIL receptor function.

One or more antibodies of the present invention (including molecules comprising, or alternatively consisting of, antibody fragments or variants thereof) that immunospecifically bind to APRIL may be used locally or systemically in the body as a therapeutic. The antibodies of this invention (including molecules comprising, or alternatively consisting of, antibody fragments or variants thereof) may also be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention (including molecules comprising, or alternatively consisting of, antibody fragments or variants thereof) may be administered alone or in combination with other types of treatments (e.g., radiation therapy, chemotherapy, hormonal therapy, immunotherapy, anti-tumor agents, anti-angiogenesis and anti-inflammatory agents). Generally, administration of products of a species origin or species reactivity (in the case of antibodies) that is the same species as that of the patient is preferred. Thus, in a preferred embodiment, human antibodies, fragments, or variants, (e.g., derivatives), or nucleic acids, are administered to a human patient for therapy or prophylaxis.

It is preferred to use high affinity and/or potent in vivo inhibiting and/or neutralizing antibodies of the invention (including molecules comprising, or alternatively consisting of, antibody fragments or variants thereof) that immunospecifically bind to APRIL, or polynucleotides encoding antibodies that immunospecifically bind to APRIL, for both immunoassays directed to and therapy of disorders related to APRIL polynucleotides or polypeptides, including fragments thereof. Such antibodies will preferably have an affinity for APRIL and/or APRIL fragments. Preferred binding affinities include those with a dissociation constant or Kd less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention bind APRIL polypeptides or fragments or variants thereof with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind APRIL polypeptides or fragments or variants thereof with a dissociation constant or $K_D$ less than or equal to $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, or $10^{-15}$M. The invention encompasses antibodies that bind APRIL polypeptides with a dissociation constant or $K_D$ that is within any one of the ranges that are between each of the individual recited values. In a preferred embodiment, antibodies of the invention neutralize APRIL activity. In another preferred embodiment, antibodies of the invention do not neutralize APRIL activity. In another preferred embodiment, antibodies of the invention inhibit B cell proliferation. In another preferred embodiment, antibodies of the invention do not inhibit B cell proliferation.

In a preferred embodiment, antibodies of the invention (including molecules comprising, or alternatively-consisting of, antibody fragments or variants thereof) inhibit or reduce binding of the soluble form of APRIL to an APRIL receptor. In another preferred embodiment, antibodies of the invention (including molecules comprising, or alternatively consisting of, antibody fragments or variants thereof) do not inhibit or reduce binding of the soluble form of APRIL to an APRIL receptor. In another preferred embodiment antibodies of the invention inhibit or reduce B cell proliferation induced by the soluble form of APRIL. In another preferred embodiment antibodies of the invention do not inhibit or reduce B cell proliferation induced by the soluble form of APRIL. In another preferred embodiment antibodies of the invention inhibit or reduce immunoglobulin production induced by the soluble form of APRIL. In another preferred embodiment antibodies of the invention do not inhibit or reduce immunoglobulin production induced by the soluble form of APRIL.

In a preferred embodiment, antibodies of the invention (including molecules comprising, or alternatively consisting of, antibody fragments or variants thereof) inhibit or reduce binding of membrane-bound APRIL to an APRIL receptor. In a preferred embodiment, antibodies of the invention (including molecules comprising, or alternatively consisting of, antibody fragments or variants thereof) do not inhibit or reduce binding of membrane-bound APRIL to an APRIL receptor. In another preferred embodiment, antibodies of the invention inhibit or reduce B cell proliferation induced by the membrane-bound form of APRIL. In another preferred embodiment, antibodies of the invention do not inhibit or reduce B cell proliferation induced by the membrane-bound form of APRIL. In another preferred embodiment, antibodies of the invention inhibit or reduce immunoglobulin production induced by the membrane bound form of APRIL. In another preferred embodiment, antibodies of the invention do not inhibit or reduce immunoglobulin production induced by the membrane bound form of APRIL.

In a preferred embodiment, antibodies of the invention (including molecules comprising, or alternatively consisting of, antibody fragments or variants thereof) inhibit or reduce binding of both the soluble and membrane-bound forms of APRIL to an APRIL receptor. In a preferred embodiment, antibodies of the invention (including molecules comprising, or alternatively consisting of, antibody fragments or variants thereof) do not inhibit or reduce binding of both the soluble and membrane-bound forms of APRIL to an APRIL receptor. In another preferred embodiment, antibodies of the invention inhibit or reduce B cell proliferation induced by either or both forms of APRIL. In another preferred embodiment, antibodies of the invention do not inhibit or reduce B cell proliferation induced by either or both forms of APRIL. In another preferred embodiment, antibodies of the invention inhibit or reduce immunoglobulin production induced by either or both forms of APRIL. In another preferred embodiment, antibodies of the invention do not inhibit or reduce immunoglobulin production induced by either or both forms of APRIL.

In one embodiment, the invention provides a method of delivering antibody conjugates of the invention to targeted cells, such as, for example, monocytic cells expressing the membrane-bound form of APRIL, or B cells expressing an APRIL receptor.

In one embodiment, the invention provides a method for the specific delivery of antibodies and antibody conjugates of the invention to cells by administering molecules of the invention that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering antibodies or antibody conjugates of the invention (e.g., antibodies conjugated with radioisotopes, toxins, or cytotoxic prodrugs). In a specific embodiment, the invention provides a method for the specific destruction of cells of monocytic lineage (e.g., monocytic cell related leukemias or lymphomas, such as, for example acute myelogenous leukemia) by administering antibodies or antibody conjugates of the invention (e.g., antibodies conjugated with radioisotopes, toxins, or cytotoxic prodrugs) that immunospecifically bind the membrane-bound form of APRIL. In another specific embodiment, the invention provides a method for the specific destruction of cells of B cell lineage (e.g., B cell related leukemias or lymphomas (e.g., chronic lymphocytic leukemia, multiple myeloma, non-Hodgkin's lymphoma, and Hodgkin's disease) by administering antibodies or antibody conjugates of the invention (e.g., antibodies conjugated with radioisotopes, toxins, or cytotoxic prodrugs) that bind soluble APRIL, but do not inhibit APRIL binding to an APRIL receptor on B cells. In another specific embodiment, the invention provides a method for the specific destruction of cells of T cell lineage (e.g., T cell lymphoma or mycosis fungoides) by administering antibodies or antibody conjugates of the invention (e.g., antibodies conjugated with radioisotopes, toxins, or cytotoxic prodrugs) that bind soluble APRIL, but do not inhibit APRIL binding to an APRIL receptor on T cells.

Preferred Therapeutic Uses of Anti-APRIL Antibodies to Treat Autoimmune Diseases and Hyperproliferative Disorders In another embodiment, therapeutic or pharmaceutical compositions of the invention are administered to an animal to treat, prevent or ameliorate immune disorders. Immune disorders include, but are not limited to, autoimmune disorders (e.g., arthritis, graft rejection, Hashimoto's thyroiditis, insulin-dependent diabetes, lupus erythematosus, idiopathic thrombocytopenic purpura and multiple sclerosis), and immunodeficiencies (e.g., selective IgA deficiency, ataxia-telangiectasia, common variable immunodeficiency (CVID), X-linked agammaglobulinemia, severe combined immunodeficiency (SCID), Wiskott-Aldrich syndrome, idiopathic hyper-eosinophilic syndrome, monocytic leukemoid reaction, monocytic leukocytosis, monocytic leukopenia, monocytopenia, monocytosis, and graft or transplant rejection).

As discussed herein, antibodies and antibody compositions of the invention, may be used to treat, prevent, ameliorate, diagnose or prognose various immune system-related disorders and/or conditions associated with these disorders, in mammals, preferably humans. Many autoimmune disorders result from inappropriate recognition of self as foreign material by immune cells. This inappropriate recognition results in an immune response leading to the destruction of the host tissue. Therefore, the administration of antibody and antibody compositions of the invention that can inhibit an immune response, particularly the proliferation of B cells and/or the production of immunoglobulins, may be an effective therapy in treating and/or preventing autoimmune disorders. Thus, in preferred embodiments, antibodies and antibody compositions of the invention are used to treat, prevent, ameliorate, diagnose and/or prognose an autoimmune disorder, or condition(s) associated with such disorder.

Autoimmune and inflammatory disorders, diseases, or conditions that may be treated, prevented, or ameliorated using the antibodies of the invention include, but are not limited to, autoimmune hemolytic anemia (including, but not limited to cryoglobinemia or Coombs positive anemia), autoimmune neonatal thrombocytopenia, idiopathic thrombocytopenic purpura, autoimmune thrombocytopenic purpura, autoimmune neutropenia, autoimmunocytopenia, hemolytic anemia, antiphospholipid syndrome, dermatitis (e.g. atopic dermatitis), gluten-sensitive enteropathy, allergic encephalomyelitis, myocarditis, relapsing polychondritis, rheumatic heart disease, glomerulonephritis (e.g., primary glomerulonephritis and IgA nephropathy), Multiple Sclerosis, Neuritis, Uveitis Ophthalmia, Polyendocrinopathies, Purpura (e.g., Henloch-Schoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, diabetes mellitus (e.g. Type I diabetes mellitus or insulin dependent diabetes mellitis), juvenile onset diabetes, autoimmune inflammatory eye, autoimmune thyroiditis, hypothyroidism (i.e., Hashimoto's thyroiditis), systemic lupus erythematosus, discoid lupus, Goodpasture's syndrome, Pemphigus, Receptor autoimmunities such as, for example, (a) Graves' Disease, (b) Myasthenia Gravis, and (c) insulin resistance, rheumatoid arthritis, scleroderma with anti-collagen antibodies, mixed connective tissue disease, polymyositis/dermatomyositis, pernicious anemia (Addison's disease), idiopathic Addison's disease, infertility, bullous pemphigoid, Sjögren's syndrome, adrenergic drug resistance (including adrenergic drug resistance with asthma or cystic fibrosis), chronic active hepatitis, primary biliary cirrhosis, other endocrine gland failure, vitiligo, vasculitis, post-MI cardiotomy syndrome, urticaria, asthma, inflammatory myopathies, and other inflammatory, granulomatous, degenerative, and atrophic disorders, and other disorders such as inflammatory skin diseases including psoriasis and sclerosis, responses associated with inflammatory bowel disease (such as Crohn's disease and ulcerative colitis), respiratory distress syndrome (including adult respiratory distress syndrome, ARDS), meningitis, encephalitis, colitis, allergic conditions such as eczema and other conditions involving infiltration of T cells and chronic inflammatory responses, atherosclerosis, leukocyte adhesion deficiency, Reynaud's syndrome, and immune responses associated with acute and delayed hypersensitivity mediated by cytokines and T-lymphocytes typically found in tuberculosis, sarcoidosis, granulomatosis and diseases involving leukocyte diapedesis, central nervous system (CNS) inflammatory disorder, multiple organ injury syndrome, antigen-antibody complex mediated diseases, anti-glomerular basement membrane disease, Lambert-Eaton myasthenic syndrome, Bechet's disease, giant cell arteritis, immune complex nephritis, IgM polyneuropathies or autoimmune thrombocytopenia etc.

In a preferred embodiment, therapeutic and pharmaceutical compositions of the invention, are used to treat, prevent, ameliorate, diagnose or prognose, a member of the group: autoimmune hemolytic anemia, primary glomerulonephritis, IgA glomerulonephritis, Goodpasture's syndrome, idiopathic thrombocytopenic purpura, CVID with autoimmune disease, Multiple Sclerosis, Myasthenia Gravis, Pemphigus, polymyositis/dermatomyositis, relapsing polychondritis, rheumatoid arthritis, Sjögren's syndrome, systemic lupus erythematosus, Uveitis, thyroiditis, vasculitis, and primary biliary cirrhosis.

In another preferred embodiment, therapeutic and pharmaceutical compositions of the invention, are used to treat, prevent, or ameliorate an immune based-rheumatologic disease, such as, for example, SLE, rheumatoid arthritis, CREST syndrome (a variant of scleroderma characterized by calcinosis, Raynaud's phenomenon, esophageal motility disorders, sclerodactyly, and telangiectasia.), Seronegative spondyloarthropathy (SpA), polymyositis/dermatomyositis, microscopic polyangiitis, hepatitis C-associated arthritis, Takayasu's arteritis, and undifferentiated connective tissue disorder.

In a specific preferred embodiment, therapeutic and pharmaceutical compositions of the invention, are used to treat, prevent, or ameliorate rheumatoid arthritis and/or medical conditions associated therewith. For example, an antibody, or antibodies, of the present invention are used to treat patients with clinical diagnosis of rheumatoid arthritis (RA). The patient treated preferably does not have a B cell malignancy. Moreover, the patient is optionally further treated with any one or more agents employed for treating RA such as salicylate; nonsteroidal anti-inflammatory drugs such as indomethacin, phenylbutazone, phenylacetic acid derivatives (e.g. ibuprofen and fenoprofen), naphthalene acetic acids (naproxen), pyrrolealkanoic acid (tometin), indoleacetic acids (sulindac), halogenated anthranilic acid (meclofenamate sodium), piroxicam, zomepirac and diflunisal; antimalarials such as chloroquine; gold salts; penicillamine; or immunosuppressive agents such as methotrexate or corticosteroids in dosages known for such drugs or reduced dosages. Antibodies of the present invention are adrministered to the RA patient according to a dosing schedule as described infra, which may be readily determined by one of ordinary skill in the art. The primary response may be determined, for example, by the Paulus index (Paulus et al. Athritis Rheum. 33:477–484 (1990)), i.e. improvement in morning stiffness, number of painful and inflamed joints, erythrocyte sedimentation (ESR), and at least a 2-point improvement on a 5-point scale of disease severity assessed by patient and by physician. Administration of an antibody, or antibodies, of the present invention will alleviate one or more of the symptoms of RA in the patient treated as described above.

In a specific preferred embodiment, therapeutic and pharmaceutical compositions of the invention, are used to treat, prevent, or ameliorate advanced rheumatoid arthritis and/or medical conditions associated therewith. For example, an antibody, or antibodies, of the present invention are used to treat patients with clinical diagnosis of advanced rheumatoid arthritis. The patient treated preferably does not have a B cell malignancy. Moreover, the patient is optionally further treated with any one or more agents employed for treating RA such as salicylate; nonsteroidal anti-inflammatory drugs such as indomethacin, phenylbutazone, phenylacetic acid derivatives (e.g. ibuprofen and fenoprofen), naphthalene acetic acids (naproxen), pyrrolealkanoic acid (tometin), indoleacetic acids (sulindac), halogenated anthranilic acid (meclofenamate sodium), piroxicam, zomepirac and diflunisal; antimalarials such as chloroquine; gold salts; penicillamine; or immunosuppressive agents such as methotrexate or corticosteroids in dosages known for such drugs or reduced dosages. Antibodies of the present invention are administered to the RA patient according to a dosing schedule as described infra, which may be readily determined by one of ordinary skill in the art. Administration of an antibody, or antibodies, of the present invention will alleviate one or more of the symptoms of advanced RA in the patient treated as described above.

In a specific preferred embodiment, therapeutic and pharmaceutical compositions of the invention are used to treat, prevent, or ameliorate systemic lupus erythematosus and/or medical conditions associated therewith. Lupus-associated conditions that may be treated, prevented, ameliorated, prognosed and/or diagnosed with the antibodies and antibody compositions of the invention include, but are not limited to, hematologic disorders (e.g., hemolytic anemia, leukopenia, lymphopenia, and thrombocytopenia), immunologic disorders (e.g., anti-DNA antibodies, and anti-Sm antibodies), rashes, photosensitivity, oral ulcers, arthritis, fever, fatigue, weight loss, serositis (e.g., pleuritus (pleurisy)), renal disorders (e.g., nephritis), neurological disorders (e.g., seizures, peripheral neuropathy, CNS related disorders), gastroinstestinal disorders, Raynaud phenomenon, and pericarditis. In a preferred embodiment, therapeutic and pharmaceutical compositions of the invention are used to treat, prevent, or ameliorate renal disorders associated with systemic lupus erythematosus. In a most preferred embodiment, therapeutic and pharmaceutical compositions of the invention are used to treat, prevent, or ameliorate nephritis associated with systemic lupus erythematosus. In another most preferred embodiment, therapeutic or pharmaceutical compositions of the invention are administered to an animal to treat, prevent or ameliorate lupus or glomerular nephritis.

In another specific embodiment, antibodies of the invention are used to treat, prevent, or ameliorate adult immune thrombocytopenic purpura. Adult immune thrombocytopenic purpura (ITP) is a relatively rare hematologic disorder that constitutes the most common of the immune-mediated cytopenias. The disease typically presents with severe thrombocytopenia that may be associated with acute hemorrhage in the presence of normal to increased megakaryocytes in the bone marrow. Most patients with ITP have an IgG antibody directed against target antigens on the outer surface of the platelet membrane, resulting in platelet sequestration in the spleen and accelerated reticuloendothelial destruction of platelets (Bussell, J. B. Hematol. Oncol. Clin. North Am. (4):179 (1990)). A number of therapeutic interventions have been shown to be effective in the treatment of ITP. Steroids are generally considered first-line therapy, after which most patients are candidates for intravenous immunoglobulin (IVIG), splenectomy, or other medical therapies including vincristine or immunosuppressive/cytotoxic agents. Up to 80% of patients with ITP initially respond to a course of steroids, but far fewer have complete and lasting remissions. Splenectomy has been recommended as standard second-line therapy for steroid failures, and leads to prolonged remission in nearly 60% of cases yet may result in reduced immunity to infection. Splenectomy is a major surgical procedure that may be associated with substantial morbidity (15%) and mortality (2%). IVIG has also been used as second line medical therapy, although only a small proportion of adult patients with ITP achieve remission. Therapeutic options that would interfere with the production of autoantibodies by activated B cells without the associated morbidities that occur with corticosteroids and/or splenectomy would provide an important treatment approach for a proportion of patients with ITP. Patients with clinical diagnosis of ITP are treated with an antibody, or antibodies of the present invention, optionally in combination with steroid therapy. The patient treated preferably does not have a B cell malignancy. Antibodies of the present invention are administered to the RA patient according to a dosing schedule as described infra, which may be readily determined by one of ordinary skill in the art. Overall patient response rate may be determined, for example, based upon a platelet count determined on two consecutive occasions two weeks apart following treatments as described above. See, George et al. "Idiopathic Thrombocytopenic Purpura: A Practice Guideline Developed by Explicit Methods for The American Society of Hematology", Blood 88:3–40 (1996), which is herein incorporated herein by reference in its entirety.

In a specific embodiment, antibodies of the invention are used to treat, prevent, or ameliorate hemolytic anemia. For example, patients diagnosed with autoimmune hemolytic anemia (AIHA), e.g., cryoglobinemia or Coombs positive anemia, are treated with an antibody, or antibodies, of the present invention. AIHA is an acquired hemolytic anemia due to auto-antibodies that react with the patient's red blood cells. The patient treated preferably does not have a B cell malignancy. The polypeptides of the invention may be administered in combination with adjunct therapies (such as glucocorticoids, prednisone, azathioprine, cyclophosphamide, vinca-laden platelets or Danazol). Antibodies of the present invention are administered to the hemolytic anemia patient according to a dosing schedule as described infra, which may be readily determined by one of ordinary skill in the art. Overall response rate may be determined, for example, based upon an improvement in blood counts, decreased requirement for transfusions, improved hemoglobin levels and/or a decrease in the evidence of hemolysis as determined by standard chemical parameters. Administration of an antibody, or antibodies of the present invention may improve any one or more of the symptoms of hemolytic anemia in the patient treated as described above. For example, the patient treated as described above may show an increase in hemoglobin and an improvement in chemical parameters of hemolysis or return to normal as measured by, for example, serum lactic dehydrogenase and/or bilirubin.

In another specific embodiment, therapeutic or pharmaceutical compositions of the invention are administered to an animal to treat, prevent or ameliorate Sjögren's syndrome and disorders associated with Sjögren's syndrome. Examples of Sjögren's syndrome associated disorders include, but are not limited to, rheumatoid arthritis, nephritis, vasculitis and thyroiditis.

In another embodiment, therapeutic or pharmaceutical compositions of the invention are administered to an animal to treat, prevent or ameliorate Myasthenia gravis.

In another embodiment, therapeutic or pharmaceutical compositions of the invention are administered to an animal to treat, prevent or ameliorate IgA nephropathy.

In another embodiment, therapeutic or pharmaceutical compositions of the invention are administered to an animal to treat, prevent or ameliorate Thyroiditis.

In another embodiment, therapeutic or pharmaceutical compositions of the invention are administered to an animal to treat, prevent or ameliorate Goodpasture's syndrome.

In another embodiment, therapeutic or pharmaceutical compositions of the invention are administered to an animal to treat, prevent or ameliorate Multiple sclerosis.

In another embodiment, therapeutic or pharmaceutical compositions of the invention are administered to an animal to treat, prevent or ameliorate common variable immunodeficiency (CVID) with autoimmune diseases.

In another embodiment, therapeutic or pharmaceutical compositions of the invention are administered to an animal to treat, prevent or ameliorate an IgE-mediated allergic reaction or histamine-mediated allergic reaction. Examples of allergic reactions include, but are not limited to, asthma, rhinitis, eczema, chronic urticaria, and atopic dermatitis. In another embodiment, therapeutic or pharmaceutical compositions of the invention are administered to an animal to treat, prevent, or ameliorate anaphylaxis, hypersensitivity to an antigenic molecule, or blood group incompatibility. In another embodiment, therapeutic or pharmaceutical compositions of the invention are administered to an animal to treat, prevent or ameliorate or modulate inflammation or an inflammatory disorder. Examples of chronic and acute inflammatory disorders that may be treated prevented or ameliorated with the therapeutic and pharmaceutical compositions of the invention include, but are not limited to, chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, Crohn's disease, inflammatory bowel disease, chronic and acute inflammatory pulmonary diseases, bacterial infection, psoriasis, septicemia, cerebral malaria, arthritis, gastroenteritis, and glomerular nephritis.

In another embodiment, therapeutic or pharmaceutical compositions of the invention are administered to an animal to treat, prevent or ameliorate ischemia and arteriosclerosis. Examples of such disorders include, but are not limited to, reperfusion damage (e.g., in the heart and/or brain) and cardiac hypertrophy.

Therapeutic or pharmaceutical compositions of the invention may also be administered to modulate blood clotting and to treat or prevent blood-clotting disorders, such as, for example, antibody-mediated thrombosis (i.e., antiphospholipid antibody syndrome (APS)). For example, therapeutic or pharmaceutical compositions of the invention may inhibit the proliferation and differentiation of cells involved in producing anticardiolipin antibodies. These compositions of the invention can be used to treat, prevent, and/or ameliorate thrombotic related events including, but not limited to, stroke (and recurrent stroke), heart attack, deep vein thrombosis, pulmonary embolism, myocardial infarction, coronary artery disease (e.g., antibody-mediated coronary artery disease), thrombosis, graft reocclusion following cardiovascular surgery (e.g., coronary arterial bypass grafts, recurrent fetal loss, and recurrent cardiovascular thromboembolic events.

Therapeutic or pharmaceutical compositions of the invention may also be administered to treat, prevent, or ameliorate organ rejection or graft-versus-host disease (GVHD) and/or conditions associated therewith. Organ rejection occurs by host immune cell destruction of the transplanted tissue through an immune response. Similarly, an immune response is also involved in GVHD, but, in this case, the foreign transplanted immune cells destroy the host tissues. The administration of antibodies of the invention, that inhibit an immune response, may be an effective therapy in preventing organ rejection or GVHD.

In another embodiment, therapeutic or pharmaceutical compositions of the invention are administered to an animal to treat, prevent or ameliorate a disease or diseases associated with increased apoptosis including, but not limited to, AIDS, neurodegenerative disorders (such as Alzheimer's disease, Parkinson's disease, Amyotrophic lateral sclerosis, Retinitis pigmentosa, Cerebellar degeneration), myelodysplastic-syndromes (such as aplastic anemia), ischemic injury (such as that caused by myocardial infarction, stroke and reperfusion injury), toxin-induced liver disease (such as that caused by alcohol), septic shock, cachexia and anorexia. In another embodiment, therapeutic or pharmaceutical compositions of the invention are administered to an animal to treat, prevent or ameliorate bone marrow failure, for example, aplastic anemia and myelodysplastic syndrome.

In another embodiment, therapeutic or pharmaceutical compositions of the invention are administered to an animal to treat, prevent or ameliorate growth, progression, and/or metastases of malignancies and proliferative disorders associated with increased cell survival, or the inhibition of apoptosis. Examples of such disorders, include, but are not limited to, leukemia (e.g., acute leukemia such as acute lymphocytic leukemia and acute myelocytic leukemia), neoplasms, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma), heavy chain disease, metastases, or any disease or disorder characterized by uncontrolled cell growth.

In a specific embodiment, therapeutic or pharmaceutical compositions of the invention are used to treat, prevent or ameliorate a disorder characterized by abnormal Monocyte proliferation.

In a specific embodiment, therapeutic or pharmaceutical compositions of the invention are used to treat, prevent or ameliorate acute myelogenous leukemia.

In a specific embodiment, therapeutic or pharmaceutical compositions of the invention are used to treat, prevent or ameliorate a disorder characterized by abnormal B cell proliferation.

In a specific embodiment, therapeutic or pharmaceutical compositions of the invention are used to treat, prevent or ameliorate chronic lymphocytic leukemia.

In a specific embodiment, therapeutic or pharmaceutical compositions of the invention are used to treat, prevent or ameliorate multiple myeloma.

In a specific embodiment, therapeutic or pharmaceutical compositions of the invention are used to treat, prevent or ameliorate Non-Hodgkin's lymphoma.

In a specific embodiment, therapeutic or pharmaceutical compositions of the invention are used to treat, prevent or ameliorate Hodgkin's disease.

In a specific embodiment, therapeutic or pharmaceutical compositions of the invention are used to treat, prevent or ameliorate lymphocytic tumors.

In a specific embodiment, therapeutic or pharmaceutical compositions of the invention are used to treat, prevent or ameliorate a disorder characterized by abnormal T cell proliferation.

In a specific embodiment, therapeutic or pharmaceutical compositions of the invention are used to treat, prevent or ameliorate mycosis fungoides.

In a specific embodiment, therapeutic or pharmaceutical compositions of the invention are used to treat, prevent or ameliorate a disorder characterized by hypergammaglobulinemia (e.g., AIDS, autoimmune diseases, and some immunodeficiencies).

Additional Therapeutic Uses

In a specific embodiment, therapeutic or pharmaceutical compositions of the invention are used to treat or prevent a disorder characterized by deficient serum immunoglobulin production, recurrent infections, and/or immune system dysfunction. Moreover, therapeutic or pharmaceutical compositions of the invention may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pneumocystis carnii.

Therapeutic or pharmaceutical compositions of the invention of the invention thereof, may be used to diagnose, prognose, treat or prevent one or more of the following diseases or disorders, or conditions associated therewith: primary immunodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

Additionally, therapeutic or pharmaceutical compositions of the invention may be used to diagnose, prognose, treat or prevent one or more of the following diseases, disorders, or conditions associated therewith, Guillain-Barre syndrome, anemia (e.g., anemia associated with parvovirus B19, patients with stable mutliple myeloma who are at high risk for infection (e.g., recurrent infection), autoimmune hemolytic anemia (e.g., warm-type autoimmune hemolytic anemia), thrombocytopenia (e.g., neonatal thrombocytopenia), and immune-mediated neutropenia), transplantation (e.g., cytomegalovirus (CMV)-negative recipients of CMV-positive organs), hypogammaglobulinemia (e.g., hypogammaglobulinemic neonates with risk factor for infection or morbidity), epilepsy (e.g., intractable epilepsy), systemic vasculitic syndromes, myasthenia gravis (e.g., decompensation in myasthenia gravis), dermatomyositis, and polymyositis.

Additional preferred embodiments of the invention include, but are not limited to, the use of therapeutic or pharmaceutical compositions of the invention in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response. In a specific nonexclusive embodiment, therapeutic or pharmaceutical compositions of the invention are administered to boost the immune system to produce increased quantities of IgG. In another specific nonexclusive embodiment, antibodies of the invention are administered to boost the immune system to produce increased quantities of IgA. In another specific nonexclusive embodiment antibodies of the invention are administered to boost the immune system to produce increased quantities of IgM.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741).

A vaccine adjuvant that enhances immune responsiveness to specific antigen. In a specific embodiment, the vaccine is an antibody described herein. In another specific embodiment, the vaccine adjuvant is a polynucleotide described herein (e.g., an antibody polynucleotide genetic vaccine adjuvant). As discussed herein, therapeutic or pharmaceutical compositions of the invention may be administered using techniques known in the art, including but not limited to, liposomal delivery, recombinant vector delivery, injection of naked DNA, and gene gun delivery.

A vaccine adjuvant that enhances immune responsiveness to specific antigen in patients infected with HIV.

A vaccine adjuvant that enhances immune responsiveness to specific antigen in premature infants.

An adjuvant to enhance tumor-specific immune responses.

An adjuvant to enhance anti-viral immune responses. Anti-viral immune responses that may be enhanced using the compositions of the invention as an adjuvant, include, but are not limited to, virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions of the invention are used as an adjuvant to enhance an immune response to the HIV gp120 antigen.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Neisseria meningitidis, Streptococcus pneumoniae*, Group B streptococcus, *Shigella* spp., Enterotoxigenic *Escherichia coli*, Enterohemorrhagic *E. coli*, *Borrelia burgdorferi*, and *Plasmodium* (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria).

As a stimulator of B cell responsiveness to pathogens.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation,-compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among B cell immunodeficient individuals, such as, for example, an individual who has undergone a partial or complete splenectomy. B cell immunodeficiencies that may be ameliorated or treated by administering the antibodies and/or compositions of the invention include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

In a specific embodiment, antibodies and/or compositions of the invention are administered to treat or ameliorate selective IgA deficiency.

In another specific embodiment, antibodies and/or compositions of the invention are administered to treat or ameliorate ataxia-telangiectasia.

In another specific embodiment, antibodies and/or compositions of the invention are administered to treat or ameliorate common variable immunodeficiency (CVID).

In another specific embodiment, antibodies and/or compositions of the invention are administered to treat or ameliorate X-linked agammaglobulinemia.

In another specific embodiment, antibodies and/or compositions of the invention are administered to treat or ameliorate severe combined immunodeficiency (SCID).

In another specific embodiment, antibodies and/or compositions of the invention are administered to treat or ameliorate Wiskott-Aldrich syndrome.

In another specific embodiment, antibodies and/or compositions of the invention are administered to treat or ameliorate X-linked Ig deficiency with hyper IgM.

As an agent to boost immunoresponsiveness among individuals having an acquired loss of B cell function. Conditions resulting in an acquired loss of B cell function that may be ameliorated or treated by administering antibodies and/or compositions of the invention include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering antibodies and/or compositions of the invention include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, T cells and/or B-cells. In one embodiment, antibody polypeptides or polynucleotides enhance antigen presentation or antagonize antigen presentation in vitro or in vivo. Moreover, in related embodiments, this enhancement or antagonism of antigen presentation may be useful in anti-tumor treatment or to modulate the immune system.

As a mediator of mucosal immune responses. The expression of APRIL on monocytes, the expression of APRIL receptor on B cells, and the responsiveness of B cells to APRIL suggest that it may be involved in exchange of signals between B cells and monocytes or their differentiated progeny. This activity is in many ways analogous to the CD40–CD154 signalling between B cells and T cells. Anti-APRIL antibodies and compositions of the invention may therefore be good regulators of T cell independent immune responses to environmental pathogens. In particular, the unconventional B cell populations (CD5+) that are associated with mucosal sites and responsible for much of the innate immunity in humans may respond to antibodies or compositions of the invention thereby enhancing or inhibiting individual's immune status.

As an agent to direct an individual's immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly, their susceptibility profile would likely change.

As a monocyte cell specific binding protein to which specific activators or inhibitors of cell growth may be attached. The result would be to focus the activity of such activators or inhibitors onto normal, diseased, or neoplastic B cell populations.

As a B cell specific binding protein to which specific activators or inhibitors of cell growth may be attached. The result would be to focus the activity of such activators or inhibitors onto normal, diseased, or neoplastic B cell populations.

As a T cell specific binding protein to which specific activators or inhibitors of cell growth may be attached. The result would be to focus the activity of such activators or inhibitors onto normal, diseased, or neoplastic T cell populations.

As a means of detecting monocytic cells by virtue of its specificity. This application may require labeling the antibody with biotin or other agents (e.g., as described herein) to afford a means of detection.

As a means of detecting B-lineage cells by virtue of its specificity. This application may require labeling the protein with biotin or other agents (e.g., as described herein) to afford a means of detection.

As a means of detecting T-lineage cells by virtue of its specificity. This application may require labeling the protein with biotin or other agents (e.g., as described herein) to afford a means of detection.

As a stimulator of B cell production in pathologies such as AIDS, chronic lymphocyte disorder and/or Common Variable Immunodeficiency.

As part of a monocyte selection device the function of which is to isolate monocytes from a heterogeneous mixture of cell types. Antibodies of the invention could be coupled to a solid support to which monocytes would then specifically bind. Unbound cells would be washed out and the bound cells subsequently eluted. A nonlimiting use of this selection would be to allow purging of tumor cells from, for example, bone marrow or peripheral blood prior to transplant.

As part of a B cell selection device the function of which is to isolate B cells from a heterogeneous mixture of cell types. Antibodies of the invention (that do not inhibit APRIL/APRIL Receptor interaction) binding soluble APRIL could be coupled to a solid support to which B cells would then specifically bind. Unbound cells would be washed out and the bound cells subsequently eluted. A nonlimiting use of this selection would be to allow purging of tumor cells from, for example, bone marrow or peripheral blood prior to transplant.

As part of a T cell selection device the function of which is to isolate T cells from a heterogeneous mixture of cell types. Antibodies of the invention (that do not inhibit APRIL/APRIL Receptor interaction) binding soluble APRIL could be coupled to a solid support to which T cells would then specifically bind. Unbound cells would be washed out and the bound cells subsequently eluted. A nonlimiting use of this selection would be to allow purging of tumor cells from, for example, peripheral blood prior to transplant.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance APRIL mediated responses.

As a means of activating monocytes/macrophages to defend against parasitic diseases that effect monocytes such as *Leishmania*.

As pretreatment of bone marrow samples prior to transplant. Such treatment would increase B cell representation and thus accelerate recovery.

As a means of regulating secreted cytokines that are elicited by APRIL and/or APRIL receptor.

Antibody polypeptides or polynucleotides of the invention may be used to modulate IgE concentrations in vitro or in vivo.

Additionally, antibody polypeptides or polynucleotides of the invention may be used to treat, prevent, and/or diagnose IgE-mediated allergic reactions. Such allergic reactions include, but are not limited to, asthma, rhinitis, and eczema.

In a specific embodiment, antibody polypeptides or polynucleotides of the invention, are administered to treat, prevent, diagnose, and/or ameliorate selective IgA deficiency.

In another specific embodiment antibody polypeptides or polynucleotides of the invention are administered to treat, prevent, diagnose, and/or ameliorate ataxia-telangiectasia.

In another specific embodiment, antibody polypeptides or polynucleotides of the invention are administered to treat, prevent, diagnose, and/or ameliorate common variable immunodeficiency.

In another specific embodiment, antibody polypeptides or polynucleotides of the invention are administered to treat, prevent, diagnose, and/or ameliorate X-linked agammaglobulinemia.

In another specific embodiment, antibody polypeptides or polynucleotides of the invention are administered to treat, prevent, diagnose, and/or ameliorate severe combined immunodeficiency (SCID).

In another specific embodiment, antibody polypeptides or polynucleotides of the invention are administered to treat, prevent, diagnose, and/or ameliorate Wiskott-Aldrich syndrome.

In another specific embodiment, antibody polypeptides or polynucleotides of the invention are administered to treat, prevent, diagnose, and/or ameliorate X-linked Ig deficiency with hyper IgM. In a specific embodiment antibody polypeptides or polynucleotides of the invention are administered to treat, prevent, diagnose, and/or ameliorate X-linked Ig deficiency with hyper IgM.

In another specific embodiment, antibody polypeptides or polynucleotides of the invention are administered to treat, prevent, and/or diagnose chronic myclogenous leukemia, acute myelogenous leukemia, leukemia, hystiocytic leukemia, monocytic leukemia (e.g., acute monocytic leukemia), leukemic reticulosis, Shilling Type monocytic leukemia, and/or other leukemias derived from monocytes and/or monocytic cells and/or tissues.

In another specific embodiment, antibody polypeptides or polynucleotides of the invention are administered to treat, prevent, diagnose, and/or ameliorate monocytic leukemoid reaction, as seen, for example, with tuberculosis.

In another specific embodiment, antibody polypeptides or polynucleotides of the invention are administered to treat, prevent, diagnose, and/or ameliorate monocytic leukocytosis, monocytic leukopenia, monocytopenia, and/or monocytosis.

In a specific embodiment, antibody polypeptides or polynucleotides of the invention are used to treat, prevent, detect, and/or diagnose monocyte disorders and/or diseases, and/or conditions associated therewith.

In a specific embodiment, antibody polypeptides or polynucleotides of the invention are used to treat, prevent, detect, and/or diagnose primary B lymphocyte disorders and/or diseases, and/or conditions associated therewith. In one embodiment, such primary B lymphocyte disorders, diseases, and/or conditions are characterized by a complete or partial loss of humoral immunity. Primary B lymphocyte disorders, diseases, and/or conditions associated therewith that are characterized by a complete or partial loss of humoral immunity and that may be prevented, treated, detected and/or diagnosed with compositions of the invention include, but are not limited to, X-Linked Agammaglobulinemia (XLA), severe combined immunodeficiency disease (SCID), and selective IgA deficiency.

In a preferred embodiment antibody polypeptides or polynucleotides of the invention are used to treat, prevent, and/or diagnose diseases or disorders affecting or conditions associated with any one or more of the various mucous membranes of the body. Such diseases or disorders include, but are not limited to, for example, mucositis, mucoclasis, mucocolitis, mucocutaneous leishmaniasis (such as, for example, American leishmaniasis, leishmaniasis americana, nasopharyngeal leishmaniasis, and New World leishmaniasis), mucocutaneous lymph node syndrome (for example, Kawasaki disease), mucoenteritis, mucoepidermoid carcinoma, mucoepidermoid tumor, mucoepithelial dysplasia, mucoid adenocarcinoma, mucoid degeneration, myxoid degeneration; myxomatous degeneration; myxomatosis, mucoid medial degeneration (for example, cystic medial necrosis), mucolipidosis (including, for example, mucolipidosis I, mucolipidosis II, mucolipidosis III, and mucolipidosis IV), mucolysis disorders, mucomembranous enteritis, mucoenteritis, mucopolysaccharidosis (such as, for example, type I mucopolysaccharidosis (i.e., Hurler's syndrome), type IS mucopolysaccharidosis (i.e., Scheie's syndrome or type V mucopolysaccharidosis), type II mucopolysaccharidosis (i.e., Hunter's syndrome), type III mucopolysaccharidosis (i.e., Sanfilippo's syndrome), type IV mucopolysaccharidosis (i.e., Morquio's syndrome), type VI mucopolysaccharidosis (i.e., Maroteaux-Lamy syndrome), type VII mucopolysaccharidosis (i.e, mucopolysaccharidosis due to beta-glucuronidase deficiency), and mucosulfatidosis), mucopolysacchariduria, mucopurulent conjunctivitis, mucopus, mucormycosis (i.e., zygomycosis), mucosal disease (i.e., bovine virus diarrhea), mucous colitis (such as, for example, mucocolitis and myxomembranous colitis), and mucoviscidosis (such as, for example, cystic fibrosis, cystic fibrosis of the pancreas, Clarke-Hadfield syndrome, fibrocystic disease of the pancreas, mucoviscidosis, and viscidosis). In a highly preferred embodiment, antibody polypeptides or polynucleotides of the invention are used to treat, prevent, and/or diagnose mucositis, especially as associated with chemotherapy.

In a preferred embodiment, antibody polypeptides or polynucleotides of the invention are used to treat, prevent, and/or diagnose diseases or disorders affecting or conditions associated with sinusitis.

An additional condition, disease or symptom that can be treated, prevented, and/or diagnosed by antibody polypeptides or polynucleotides of the invention is osteomyelitis.

An additional condition, disease or symptom that can be treated, prevented, and/or diagnosed by antibody polypeptides or polynucleotides of the invention is endocarditis.

All of the above described applications as they may apply to veterinary medicine.

Antibody polypeptides or polynucleotides of the invention may be used to treat, prevent, and/or diagnose diseases and disorders of the pulmonary system (e.g., bronchi such as, for example, sinopulmonary and bronchial infections and conditions associated with such diseases and disorders and other respiratory diseases and disorders. In specific embodiments, such diseases and disorders include, but are not limited to, bronchial adenoma, bronchial asthma, pneumonia (such as, e.g., bronchial pneumonia, bronchopneumonia, and tuberculous bronchopneumonia), chronic obstructive pulmonary disease (COPD), bronchial polyps, bronchiectasia (such as, e.g., bronchiectasia sicca, cylindrical bronchiectasis, and saccular bronchiectasis), bronchiolar adenocarcinoma, bronchiolar carcinoma, bronchiolitis (such as, e.g., exudative bronchiolitis, bronchiolitis fibrosa obliterans, and proliferative bronchiolitis), bronchiolo-alveolar carcinoma, bronchitic asthma, bronchitis (such as, e.g., asthmatic bronchitis, Castellani's bronchitis, chronic bronchitis, croupous bronchitis, fibrinous bronchitis, hemorrhagic bronchitis, infectious avian bronchitis, obliterative bronchitis, plastic bronchitis, pseudomembranous bronchitis, putrid bronchitis, and verminous bronchitis), bronchocentric granulomatosis, bronchoedema, bronchoesophageal fistula, bronchogenic carcinoma, bronchogenic cyst, broncholithiasis, bronchomalacia, bronchomycosis (such as, e.g., bronchopulmonary aspergillosis), bronchopulmonary spirochetosis, hemorrhagic bronchitis, bronchorrhea, bronchospasm, bronchostaxis, bronchostenosis, Biot's respiration, bronchial respiration, Kussmaul respiration, Kussmaul-Kien respiration, respiratory acidosis, respiratory alkalosis, respiratory distress syndrome of the newborn, respiratory insufficiency, respiratory scleroma, respiratory syncytial virus, and the like.

In a specific embodiment, antibody polypeptides or polynucleotides of the invention are used to treat, prevent, and/or diagnose chronic obstructive pulmonary disease (COPD).

In another embodiment, antibody polypeptides or polynucleotides of the invention are used to treat, prevent, and/or diagnose fibroses and conditions associated with fibroses, including, but not limited to, cystic fibrosis (including such fibroses as cystic fibrosis of the pancreas, Clarke-Hadfield syndrome, fibrocystic disease of the pancreas, mucoviscidosis, and viscidosis), endomyocardial fibrosis, idiopathic retroperitoneal fibrosis, leptomeningeal fibrosis, mediastinal fibrosis, nodular subepidermal fibrosis, pericentral fibrosis, perimuscular fibrosis, pipestem fibrosis, replacement fibrosis, subadventitial fibrosis, and Symmers' clay pipestem fibrosis.

In another embodiment, therapeutic or pharmaceutical compositions of the invention are administered to an animal to treat, prevent or ameliorate infectious diseases. Infectious diseases include diseases associated with yeast, fungal, viral and bacterial infections. Viruses causing viral infections which can be treated or prevented in accordance with this invention include, but are not limited to, retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus, HHV6–HHV8, and cytomegalovirus), arenavirues (e.g., lassa fever virus), paramyxoviruses (e.g., morbillivirus virus, human respiratory syncytial virus, mumps, and pneumovirus), adenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C), papovaviruses (e.g., papillomavirues), picornaviruses (e.g., rhinoviruses, enteroviruses and hepatitis A viruses), poxviruses, reoviruses (e.g., rotavirues), togaviruses (e.g., rubella virus), rhabdoviruses (e.g., rabies virus). Microbial pathogens causing bacterial infections include, but are not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter* (*Vibrio*) *fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp., and *Helicobacter pylori*.

In another embodiment, therapeutic or pharmaceutical compositions of the invention are administered to an animal to treat, prevent or ameliorate infectious diseases associated with chronic lymphocytic leukemia.

In another embodiment, therapeutic or pharmaceutical compositions of the invention are administered to an animal to treat, prevent or ameliorate infectious diseases associated with multiple myeloma.

In another embodiment, therapeutic or pharmaceutical compositions of the invention are administered to an animal to treat, prevent or ameliorate infectious diseases associated with burns.

In another embodiment, therapeutic or pharmaceutical compositions of the invention are administered to an animal to treat, prevent or ameliorate infectious diseases associated with hypogammaglobulinemia.

In another embodiment, therapeutic or pharmaceutical compositions of the invention are administered to an animal to treat, prevent or ameliorate secondary infections associated with HIV infection.

In another embodiment, therapeutic or pharmaceutical compositions of the invention are administered to an animal to treat, prevent or ameliorate secondary infections associated with AIDS.

Gene Therapy

In a specific embodiment, nucleic acids comprising sequences encoding antibodies, or functional derivatives thereof, are administered to treat, inhibit or prevent a disease or disorder associated with aberrant expression and/or activity of APRIL and/or its receptor, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 1 1(5): 155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises, or alternatively consists of, nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342: 435–438 (1989). In specific embodiments, the expressed antibody molecule is an scFv; alternatively, the nucleic acid sequences include sequences encoding both the heavy and light chains, or fragments or variants thereof, of an antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contain nucleic acid sequences encoding an antibody of the invention or fragments or variants thereof are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequence encoding the antibody to be used in gene therapy is cloned into one or more vectors, which facilitates delivery of the gene into a patient. More detail about retroviral vectors can be found in Boesen et al., Biotherapy 6:291–302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., J. Clin. Invest. 93:644–651(1994); Klein et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993), present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Clin. Pharma. Ther. 29:69–92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 7 1:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Utility of a Composition

The compounds of the invention are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a patient tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a patient's disorder, to determine if an antibody or composition of the present invention has a desired effect upon such cell types. Preferably, the antibodies or compositions of the invention are also tested in in vitro assays and animal model systems prior to administration to humans.

Antibodies or compositions of the present invention for use in therapy can be tested for their toxicity in suitable animal model systems, including but not limited to rats, mice, chicken, cows, monkeys, and rabbits. For in vivo testing of an antibody's or a composition's toxicity, any animal model system known in the art may be used.

Efficacy in treating or preventing viral infection may be demonstrated by detecting the ability of an antibody or composition of the invention to inhibit the replication of the virus, to inhibit transmission or prevent the virus from establishing itself in its host, or to prevent, ameliorate or alleviate the symptoms of disease a progression. The treatment is considered therapeutic if there is, for example, a reduction in viral load, amelioration of one or more symptoms, or a decrease in mortality and/or morbidity following administration of an antibody or composition of the invention.

Antibodies or compositions of the invention can be tested for the ability to induce the expression of cytokines such as IFN-γ, by contacting cells, preferably human cells, with an antibody or composition of the invention or a control antibody or control composition and determining the ability of the antibody or composition of the invention to induce one or more cytokines. Techniques known to those of skill in the art can be used to measure the level of expression of cytokines. For example, the level of expression of cytokines can be measured by analyzing the level of RNA of cytokines by, for example, RT-PCR and Northern blot analysis, and by analyzing the level of cytokines by, for example, immunoprecipitation followed by western blot analysis and ELISA. In a preferred embodiment, a compound of the invention is tested for its ability to induce the expression of IFN-γ.

Antibodies or compositions of the invention can be tested for their ability to modulate the biological activity of immune cells by contacting immune cells, preferably human immune cells (e.g., T-cells, B-cells, and Natural Killer cells), with an antibody or composition of the invention or a control compound and determining the ability of the antibody or composition of the invention to modulate (i.e, increase or decrease) the biological activity of immune cells. The ability of an antibody or composition of the invention to modulate the biological activity of immune cells can be assessed by detecting the expression of antigens, detecting the proliferation of immune cells (i.e., B-cell proliferation), detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs). In a preferred embodiment, the ability of an antibody or composition of the invention to induce B-cell proliferation is measured. In another preferred embodiment, the ability of an antibody or composition of the invention to modulate immunoglobulin expression is measured.

Antibodies or compositions of the invention can be tested for their ability to reduce tumor formation in in vitro, ex vivo and in vivo assays. Antibodies or compositions of the invention can also be tested for their ability to inhibit viral replication or reduce viral load in in vitro and in vivo assays. Antibodies or compositions of the invention can also be tested for their ability to reduce bacterial numbers in in vitro and in vivo assays known to those of skill in the art. Antibodies or compositions of the invention can also be tested for their ability to alleviate of one or more symptoms associated with cancer, an immune disorder (e.g., an inflammatory disease), a neurological disorder or an infectious disease. Antibodies or compositions of the invention can also be tested for their ability to decrease the time course of the infectious disease. Further, antibodies or compositions of the invention can be tested for their ability to increase the survival period of animals suffering from disease or disorder, including cancer, an immune disorder or an infectious disease. Techniques known to those of skill in the art can be used to analyze the function of the antibodies or compositions of the invention in vivo.

Therapeutic/Prophylactic Compositions and Administration

The invention provides methods of treatment, inhibition and prophylaxis by administration to a subject of an effective amount of antibody (or fragment or variant thereof) or pharmaceutical composition of the invention, preferably an antibody of the invention. In a preferred aspect, an antibody or fragment or variant thereof is substantially purified (i.e., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer antibody or fragment or variant thereof of the invention, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429–4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.).

In yet another embodiment, the composition can be delivered in a controlled release system. In one embodiment, a pump may be used (see Langer, supra; Sefton, CRC Crit. Ref. Biomed. Eng. 14:20 1 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the composition of the invention is a nucleic acid encoding a protein, the nucleic acid can be administered in vivo to promote expression of its encoded protein, by constructing it as part of an appropriate nucleic acid expression vector and-administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

The antibodies and antibody compositions of the invention may be administered alone or in combination with other adjuvants. Adjuvants that may be administered with the antibody and antibody compositions of the invention include, but are not limited to, alum, alum plus deoxycholate (ImmunoAg), MTP-PE (Biocine Corp.), QS21 (Genentech, Inc.), BCG, and MPL. In a specific embodiment, antibody and antibody compositions of the invention are administered in combination with alum. In another specific embodiment, antibody and antibody compositions of the invention are administered in combination with QS-21. Further adjuvants that may be administered with the antibody and antibody compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the antibody and antibody compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In another specific embodiment, antibody and antibody compositions of the invention are used in -combination with PNEUMOVAX-23™ to treat, prevent, and/or diagnose infection and/or any disease, disorder, and/or condition associated therewith. In one embodiment, antibody and antibody compositions of the invention are used in combination with PNEUMOVAX-23™ to treat, prevent, and/or diagnose any Gram-positive bacterial infection and/or any disease, disorder, and/or condition associated therewith. In another embodiment, antibody and antibody compositions of the invention are used in combination with PNEUMOVAX-23™ to treat, prevent, and/or diagnose infection and/or any disease, disorder, and/or condition associated with one or more members of the genus *Enterococcus* and/or the genus *Streptococcus*. In another embodiment, antibody and antibody compositions of the invention are used in any combination with PNEUMOVAX-23™ to treat, prevent, and/or diagnose infection and/or any disease, disorder, and/or condition associated with one or more members of the Group B streptococci. In another embodiment, antibody and antibody compositions of the invention are used in combination with PNEUMOVAX-23™ to treat, prevent, and/or diagnose infection and/or any disease, disorder, and/or condition associated with *Streptococcus pneumoniae*.

The antibody and antibody compositions of the invention may be administered alone or in combination with other therapeutic agents, including but not limited to, chemotherapeutic agents, antibiotics, antivirals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the antibody and antibody compositions of the invention are administered in combination with other members of the TNF family. TNF, TNF-related or TNF-like molecules that may be administered with the antibody and antibody compositions of the invention include, but are not limited to, antibodies which immunospecifically bind BLyS, soluble forms of BCMA, TACI, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (J. Exp. Med. 188 (6):1185–1190 (1998)), endokine-alpha (International Publication No. WO 98/07880), Neutrokine-alpha (BLyS; International Application Publication No. WO 98/18921), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), 312C2 (International Publication No. WO 98/06842), and TR12, and soluble forms CD154, CD70, and CD153.

In a preferred embodiment, the antibody and antibody compositions of the invention are administered in combination with CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the antibody and antibody compositions of the invention are administered alone or in combination with an anti-angiogenic agent(s). Anti-angiogenic agents that may be administered with the antibody and antibody compositions of the invention include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; (Takeuchi et al., Agents Actions 36:312–316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. Brem and J. Folkman J Pediatr. Surg. 28:445–51 (1993)); an integrin alpha v beta 3 antagonist (C. Storgard et al., J Clin. Invest. 103:47–54 (1999)); carboxynaminolmidazole; Carboxyamidotriazole (CAI) (National Cancer Institute, Bethesda, Md.); Conbretastatin A-4 (CA4P) (OXiGENE, Boston, Mass.); Squalamine (Magainin Pharmaceuticals, Plymouth Meeting, Pa.); TNP-470, (Tap Pharmaceuticals, Deerfield, Ill.); ZD-0101 AstraZeneca (London, UK); APRA (CT2584); Benefin, Byrostatin-1 (SC339555); CGP-41251 (PKC 412); CM101; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3340) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the compounds of the invention may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the antibody and antibody compositions of the invention include, but are not limited to, AG-3340 (Agouron, La Jolla, Calif.), BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aetema, St-Foy, Quebec). Examples of anti-angiogenic inhibitors that act by blocking the function of endothelial cell-extracellular matrix adhesion molecules and which may be administered in combination with the antibody and antibody compositions of the invention include, but are not limited to, EMD-121974 (Merck KcgaA Darmstadt, Germany) and Vitaxin (Ixsys, La Jolla, Calif./Medimmune, Gaithersburg, Md.). Examples of anti-angiogenic agents that act by directly antagonizing or inhibiting angiogenesis inducers and which may be administered in combination with the antibody and antibody compositions of the invention include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis, which may be administered in combination with the antibody and antibody compositions of the invention, include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In particular embodiments, the use of antibody and antibody compositions of the invention in combination with anti-angiogenic agents is contemplated for the treatment, prevention, and/or amelioration of an autoimmune disease, such as for example, an autoimmune disease described herein.

In a particular embodiment, the use of antibody and antibody compositions of the invention in combination with anti-angiogenic agents is contemplated for the treatment, prevention, and/or amelioration of arthritis. In a more particular embodiment, the use of antibody and antibody compositions of the invention in combination with anti-angiogenic agents is contemplated for the treatment, prevention, and/or amelioration of rheumatoid arthritis.

In another embodiment, antibody and antibody compositions of the invention are administered in combination with an anticoagulant. Anticoagulants that may be administered with the antibody and antibody compositions of the invention include, but are not limited to, heparin, warfarin, and aspirin. In a specific embodiment, antibody and antibody compositions of the invention are administered in combination with heparin and/or warfarin. In another specific embodiment, antibody and antibody compositions of the invention are administered in combination with warfarin. In another specific embodiment, antibody and antibody compositions of the invention are administered in combination with warfarin and aspirin. In another specific embodiment, antibody and antibody compositions of the invention are administered in combination with heparin. In another specific embodiment, antibody and antibody compositions of the invention are administered in combination with heparin and aspirin.

In another embodiment, antibody and antibody compositions of the invention are administered in combination with an agent that suppresses the production of anticardiolipin antibodies. In specific embodiments, the polynucleotides of the invention are administered in combination with an agent that blocks and/or reduces the ability of anticardiolipin antibodies to bind phospholipid-binding plasma protein beta 2-glycoprotein I (b2GPI).

In certain embodiments, antibody and antibody compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the antibody and antibody compositions of the invention, include, but are not limited to, RETROVIR™ (zidovudine/AZT), VUDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the antibody and antibody compositions of the invention, include, but are not limited to, VIRAMUNE™ (nevirapine), RESCRPTOR™ (delavirdine), and SUSTIVA™ (efavirenz). Protease inhibitors that may be administered in combination with the antibody and antibody compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with antibody and antibody compositions of the invention to treat, prevent, and/or diagnose AIDS and/or to treat, prevent, and/or diagnose HIV infection.

In other embodiments, antibody and antibody compositions of the invention may be administered in combination with anti-opportunistic infection agents. Anti-opportunistic agents that may be administered in combination with the antibody and antibody compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, antibody and antibody compositions of the invention are used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic *Pneumocystis carinii* pneumonia infection. In another specific embodiment, antibody and antibody compositions of the invention are used in any combination with ISONIAZID™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, antibody and antibody compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, antibody and antibody compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, antibody and antibody compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, antibody and antibody compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, antibody and antibody compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, antibody and antibody compositions of the invention are used in any combination with LEUCOVORIN™ and/or NEUPOGEN™ to prophylactically treat, prevent, and/or diagnose an opportunistic bacterial infection.

In a further embodiment, the antibody and antibody compositions of the invention are administered in combination with an antiviral agent. Antiviral agents that may be administered with the antibody and antibody compositions of the invention include, but are not limited to, acyclovir, ribavirin, amantadine, and remantidine.

In a further embodiment, the antibody and antibody compositions of the invention are administered in combination with an antibiotic agent. Antibiotic agents that may be administered with the antibody and antibody compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the antibody and antibody compositions of the invention include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells.

In specific embodiments, antibody and antibody compositions of the invention are administered in combination with immunosuppressants. Immunosuppressants preparations that may be administered with the antibody and antibody compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the antibody and antibody compositions of the invention are administered in combination with steroid therapy. Steroids that may be administered in combination with the antibody and antibody compositions of the invention, include, but are not limited to, oral corticosteroids, prednisone, and methylprednisolone (e.g., IV methylprednisolone). In a specific embodiment, antibody and antibody compositions of the invention are administered in combination with prednisone. In a further specific embodiment, the antibody and antibody compositions of the invention are administered in combination with prednisone and an immunosuppressive agent. Immunosuppressive agents that may be administered with the antibody and antibody compositions of the invention and prednisone are those described herein, and include, but are not limited to, azathioprine, cylophosphamide, and cyclophosphamide IV. In another specific embodiment, antibody and antibody compositions of the invention are administered in combination with methylprednisolone. In a further specific embodiment, the antibody and antibody compositions of the invention are administered in combination with methylprednisolone and an immunosuppressive agent. Immunosuppressive agents that may be administered with the antibody and antibody compositions of the invention and methylprednisolone are those described herein, and include, but are not limited to, azathioprine, cylophosphamide, and cyclophosphamide IV.

In a preferred embodiment, the antibody and antibody compositions of the invention are administered in combination with an antimalarial. Antimalarials that may be administered with the antibody and antibody compositions of the invention include, but are not limited to, hydroxychloroquine, chloroquine, and/or quinacrine.

In a preferred embodiment, the antibody and antibody compositions of the invention are administered in combination with an NSAID.

In a nonexclusive embodiment, the antibody and antibody compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In a preferred embodiment, the antibody and antibody compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, LJP 394 (La Jolla Pharmaceutical Company, San Diego, Calif.) and prednisolone.

In a more preferred embodiment, the antibody and antibody compositions of the invention are administered in combination with an antimalarial, methotrexate, anti-TNF antibody, ENBREL™ and/or suflasalazine. In one embodiment, the antibody and antibody compositions of the invention are administered in combination with methotrexate. In another embodiment, the antibody and antibody compositions of the invention are administered in combination with anti-TNF antibody. In another embodiment, the antibody and antibody compositions of the invention are administered in combination with methotrexate and anti-TNF antibody. In another embodiment, the antibody and antibody compositions of the invention are administered in combination with suflasalazine. In another specific embodiment, the antibody and antibody compositions of the invention are administered in combination with methotrexate, anti-TNF antibody, and suflasalazine. In another embodiment, the antibody and antibody compositions of the invention are administered in combination ENBREL™. In another embodiment, the antibody and antibody compositions of the invention are administered in combination with ENBREL™ and methotrexate. In another embodiment, the antibody and antibody compositions of the invention are administered in combination with ENBREL™, methotrexate and suflasalazine. In another embodiment, the antibody and antibody compositions of the invention are administered in combination with ENBREL™, methotrexate and suflasalazine. In other embodiments, one or more antimalarials is combined with one of the above-recited combinations. In a specific embodiment, the antibody and antibody compositions of the invention are administered in combination with an antimalarial (e.g., hydroxychloroquine), ENBREL™, methotrexate and suflasalazine. In another specific embodiment, the antibody and antibody compositions of the invention are administered in combination with an antimalarial (e.g., hydroxychloroquine), sulfasalazine, anti-TNF antibody, and methotrexate.

In an additional embodiment, antibody and antibody compositions of the invention are administered alone or in combination with one or more intravenous immune globulin preparations. Intravenous immune globulin preparations that may be administered with the antibody and antibody compositions of the invention include, but not limited to, GAMMAR™, IVEEGAM™, SANDOGLOBULIN™, GAMMAGARD S/D™, and GAMIMUNE™. In a specific embodiment, antibody and antibody compositions of the invention are administered in combination with intravenous immune globulin preparations in transplantation therapy (e.g., bone marrow transplant).

CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the antibody and antibody compositions of the invention are administered alone or in combination with an anti-inflammatory agent. Anti-inflammatory agents that may be administered with the antibody and antibody compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the antibody and antibody compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, antibody and antibody compositions of the invention are administered in combination with CHOP (cyclophosphamide, doxorubicin, vincristine, and prednisone) or any combination of the components of CHOP. In another embodiment, antibody and antibody compositions of the invention are administered in combination with Rituximab. In a further embodiment, antibody and antibody compositions of the invention are administered with Rituximab and CHOP, or Rituximab and any combination of the components of CHOP.

In an additional embodiment, the antibody and antibody compositions of the invention are administered in combination with cytokines. Cytokines that may be administered with the antibody and antibody compositions of the invention include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In preferred embodiments, antibody and antibody compositions of the invention are administered with APRIL (e.g., amino acids 134–285 of SEQ ID NO:3228). In another embodiment, antibody and antibody compositions of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, the antibody and antibody compositions of the invention are administered in combination with IL4 and IL10.

In one embodiment, the antibody and antibody compositions of the invention are administered in combination with one or more chemokines. In specific embodiments, the antibody and antibody compositions of the invention are administered in combination with an α(CxC) chemokine selected from the group consisting of gamma-interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B cell stimulatory factor (PBSF)); and/or a β(CC) chemokine selected from the group consisting of: RANTES (regulated on activation, normal T expressed and secreted), macrophage inflammatory protein-1 alpha (MIP-1α), macrophage inflammatory protein-1 beta (MIP-1β), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1γ), macrophage inflammatory protein-3 alpha (MIP-3α), macrophage inflammatory protein-3 beta (MIP-3β), macrophage inflammatory protein-4 (MIP-4/DC-CK-1/PARC), eotaxin, Exodus, and I-309; and/or the γ(C) chemokine, lymphotactin.

In another embodiment, the antibody and antibody compositions of the invention are administered with chemokine beta-8, chemokine beta-1, and/or macrophage inflammatory protein-4. In a preferred embodiment, the antibody and antibody compositions of the invention are administered with chemokine beta-8.

In an additional embodiment, the antibody and antibody compositions of the invention are administered in combination with an IL-4 antagonist. IL-4 antagonists that may be administered with the antibody and antibody compositions of the invention include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

The invention also encompasses combining the polynucleotides and/or polypeptides of the invention (and/or agonists or antagonists thereof) with other proposed or conventional hematopoietic therapies. Thus, for example, the polynucleotides and/or polypeptides of the invention (and/or agonists or antagonists thereof) can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations of the antibody and antibody compositions of the invention with compounds generally used to treat aplastic anemia, such as, for example, methenolene, stanozolol, and nandrolone; to treat iron-deficiency anemia, such as, for example, iron preparations; to treat malignant anemia, such as, for example, vitamin $B_{12}$ and/or folic acid, and to treat hemolytic anemia, such as, for example, adrenocortical steroids, e.g., corticoids. See e.g., Resegotti et al., Panminerva Medica, 23:243–248 (1981);

Kurtz, FEBS Letters, 14a:105–108 (1982); McGonigle et al., Kidney Int., 25:437–444 (1984); and Pavlovic-Kantera, Expt. Hematol., 8(supp. 8) 283–291 (1980), the contents of each of which are hereby incorporated by reference in their entireties.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins, See for e.g., Dunn, "Current Concepts in Erythropoiesis", John Wiley and Sons (Chichester, England, 1983); Kalmani, Kidney Int., 22:383–391 (1982); Shahidi, New Eng. J. Med., 289:72–80 (1973); Urabe et al., J. Exp. Med., 149:1314–1325 (1979); Billat et al., Expt. Hematol., 10:133–140 (1982); Naughton et al., Acta Haemat, 69:171–179 (1983); Cognote et al. in abstract 364, Proceedings 7th Intl. Cong. of Endocrinology (Quebec City, Quebec, Jul. 1–7, 1984); and Rothman et al., 1982, J. Surg. Oncol., 20:105–108 (1982). Methods for stimulating hematopoiesis comprise administering a hematopoietically effective amount (i.e., an amount which effects the formation of blood cells) of a pharmaceutical composition containing polynucleotides and/or polypeptides of the invention (and/or agonists or antagonists thereof) to a patient. The polynucleotides and/or polypeptides of the invention and/or agonists or antagonists thereof is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin $B_{12}$, folic acid and/or adrenocortical steroids.

In an additional embodiment, the antibody and antibody compositions of the invention are administered in combination with hematopoietic growth factors. Hematopoietic growth factors that may be administered with the antibody and antibody compositions of the invention include, but are not limited to, LEUKINE™ (SARGRAMOSTIM™) and NEUPOGEN™ (FILGRASTIM™).

In an additional embodiment, the antibody and antibody compositions of the invention are administered in combination with fibroblast growth factors. Fibroblast growth factors that may be administered with the antibody and antibody compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Additionally, the antibody and antibody compositions of the invention may be administered alone or in combination with other therapeutic regimens, including but not limited to, radiation therapy. Such combinatorial therapy may be administered sequentially and/or concomitantly.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody of the invention, preferably a purified antibody, in one or more containers. In an alterative embodiment, a kit comprises an antibody fragment that immunospecifically binds to APRIL. In a specific embodiment, the kits of the present invention contain a substantially isolated APRIL polypeptide as a control. Preferably, the kits of the present invention further comprise a control antibody, which does not react with APRIL. In another specific embodiment, the kits of the present invention contain a means for detecting the binding of an antibody to APRIL (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized APRIL. The APRIL provided in the kit may also be attached to a solid support. In a more specific embodiment the detecting means of the above-described kit includes a solid support to which APRIL is attached. Such a kit may also include a non-attached reporter-labeled anti-human antibody. In this embodiment, binding of the antibody to APRIL can be detected by binding of the said reporter-labeled antibody.

In an additional embodiment, the invention includes a diagnostic kit for use in screening serum to identify the presence of antigens of the polypeptide of the invention. The diagnostic kit includes a substantially isolated antibody specifically immunoreactive with APRIL, and means for detecting the binding of APRIL to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound APRIL obtained by the methods of the present invention. After APRIL binds to a specific antibody, the unbound serum components are removed by washing, reporter-labeled anti-human antibody is added, unbound anti-human antibody is removed by washing, and a reagent is reacted with reporter-labeled anti-human antibody to bind reporter to the reagent in proportion to the amount of bound anti-APRIL antibody on the solid support. Typically the reporter is an enzyme, which is detected by incubating the solid phase in the presence of a suitable fluorometric, luminescent or colorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant APRIL, and a reporter-labeled anti-human antibody for detecting surface-bound anti-APRIL antibody.

EXAMPLES

Example 1

Selection of APRIL Binding scFvs

Rescue of Large Libraries

An scFv library of up to $1\times10^{11}$ clones, which is an expanded version of the $1.38\times10^{10}$ library described (Vaughan et. al. *Nature Biotechnology* 14:309–314 (1996)), was used to select antibodies specific for FLAG-tagged APRIL. Phage were rescued by taking $3\times10^{10}$ cells from a glycerol stock culture and growing in 2YTAG (2YT media supplemented with 100 µg/ml ampicillin and 2% (w/v) glucose) at 37° C. for 2 h with shaking. M13K07 helper phage (Stratagene) was added to the culture at a multiplicity of infection (moi) of approximately 10. The culture was incubated stationary at 37° C. for 15 min followed by 45 min with light aeration (200 rpm) at the same temperature. The culture was centrifuged and the cells were resuspended in 500 ml 2YTAK (2YT media supplemented with 100 µg/ml kanamycin), and the culture incubated overnight at 30° C. with good aeration (300 rpm). Phage particles were purified and concentrated by three cycles of polyethylene glycol (PEG) precipitation (20% PEG 6000, 2.5M NaCl) on ice, then resuspended in phosphate buffered saline (PBS) at $10^{12}$ transducing units (tu)/ml, titrated as ampicillin resistant clones.

Selection Method 1: Panning

Purified phagemids were first blocked by incubation in 3% MPBS (3% 'Marvel' skimmed milk powder in PBS) for 1 h at room temperature (RT). The phagemid particles were then transferred to an immunoplate (Nunc; Maxisorp) which had been coated with soluble purified APRIL (10 µg/ml in PBS) overnight at 4° C. and blocked for 1 h at 37° C. with 3% MPBS. The plate was incubated stationary at 37° C. for 1 hour and then washed 10 times with PBS-Tween (PBS with 0.1% Tween '20') and 10 times with PBS. Bound phagemid particles were eluted by incubation in 500 µl elution buffer (2.5 mg trypsin, 1 mM $CaCl_2$, 50 mM Tris HCl pH 8.0) for 30 min at 37° C. The eluted phage were used to infect 10 ml exponentially growing *E. coli* TG1. Infected cells were grown in 2YT broth for 1 h at 37° C. with light aeration, then streaked onto 2YTAG agar plates (243 mm×243 mm; Nunc) and incubated overnight at 30° C. Colonies were scraped off the plates into 10 ml of 2YT broth and 15% (v/v) glycerol added for storage −70° C.

Glycerol stock cultures from the first round of panning on APRIL were then superinfected with helper phage and rescued to give phagemid particles for the second round of panning. Twenty-five microliters of glycerol stock was inoculated into 25 ml 2YTAG broth, and incubated at 37° C. with good aeration until the $OD_{600\ nm}$ reached 0.7. M13K07 helper phage (moi=10) was added to the culture which was then incubated stationary for 15 min at 37° C. then with shaking for 45 min at the same temperature. The culture was centrifuged, the cells were resuspended in 50 ml prewarmed 2YTAK and rescue was performed overnight at 30° C. as before. Phagemid particles were purified and concentrated as before and resuspended in PBS to $10^{13}$ tu/ml. Repertoires harvested at subsequent rounds of selection were superinfected and rescued in the same way.

Selection Method 2: Panning on Captured FLAG-tagged APRIL

The method for panning on captured FLAG-tagged APRIL was the same as selection method 1 except for the APRIL capture and phagemid deselection steps. Ten micrograms/ml M2 anti-FLAG (Sigma) monoclonal antibody (mAb) in PBS was coated onto wells of an immunoplate (Nunc; Maxisorp) overnight at 4° C. After washing the antibody-coated wells 2 times with PBS, the FLAG-tagged APRIL was added at 5 µg/ml in PBS and incubated at RT for 2 h. Wells containing captured FLAG-tagged APRIL were washed 2 times with PBS and then blocked with 3% MPBS as described in selection method 1. Phagemid particles, blocked by incubation in MPBS for 1 h at RT, were incubated for 1.5 h at RT on anti-FLAG mAb-coated wells to deselect before transferring to the FLAG-tagged APRIL-coated wells.

Selection Method 3: Soluble Selection on FLAG-tagged APRIL

Soluble selections with FLAG-tagged APRIL were performed using phagemid particles prepared as described in selection method 1. The soluble selection was performed as follows. $10^{12}$ tu/ml phagemid particles were blocked by incubating in 3% MPBS for 1 h at RT before adding 100 µl M2 anti-FLAG agarose (Sigma) to deselect for 1 h at RT with rotation. The agarose was pelleted by centrifugation at 13K rpm for 1 min and the supernatant transferred to a new eppendorf. FLAG-tagged APRIL was added to the blocked phagemid particles at a concentration of 250 nM and the tube rotated at RT for 2 h. At the same time, 100 µl M2 anti-FLAG agarose was blocked by incubating in 3% MPBS for 1 h with rotation. Following the 2 h incubation of phagemid particles with FLAG-tagged APRIL, the blocked agarose was pelleted by centrifugation and the 3% MPBS was removed and replaced by the phagemid and FLAG-tagged APRIL mixture. The tube was rotated for a further 30 min at RT before pelleting the FLAG-agarose, removing the supernatant and replacing with PBS-Tween. This wash step was repeated twice more with PBS-Tween and then three times with PBS before eluting as described in selection method 1.

Selection Method 4: Selection on Biotinylated APRIL

Selections with biotinylated APRIL were performed using phagemid particles prepared as described in selection method 1. 10 µg/ml biotinylated APRIL (made as described in the assay section) in PBS was captured on streptavidin-coated plates (Pierce) by incubation for 2 hours at RT. The remainder of the selection was performed as described in selection method 1.

Selection Method 5: Panning with Deselection on APRIL/BCMA Complex

This selection is identical to the panning method (selection method 1) except that a deselection step was performed using pre-complexed APRIL/BCMA. BCMA was coated onto immunoplates overnight at 4° C. before being blocked with 3% MPBS for 1 hour at 37° C. APRIL was then added at 10 µg/ml in MPBS for 1 h at RT to form APRIL/BCMA complexes. Phagemid particles in MPBS were deselected on APRIL/BCMA wells for 1.5 h at 37° C. before performing selection on APRIL-coated immunoplate wells as described in selection method 1.

3 rounds of each selection method were performed and individual colonies screened by phage ELISA for binding to APRIL.

Phage ELISA

To determine the specificity of each of the antibodies, a phage ELISA was performed for each antibody against APRIL and either BSA or an uncoated well.

Individual *E. coli* colonies containing phagemid were inoculated into 96 well plates containing 100 μl 2TYAG medium per well. Plates were incubated at 37° C. for 4 hours, with shaking. M13K07 helper phage was added to each well to an moi of 10 and the plates were incubated for a further 1 hour at 37° C. The plates were centrifuged in a benchtop centrifuge at 2000 rpm for 10 minutes. The supernatant was removed and cell pellets were resuspended in 100 μl 2TYAK and incubated at 30° C. overnight, shaking. The next day, plates were centrifuged at 2000 rpm for 10 min and 100 μl phage-containing supernatant from each well carefully transferred into a fresh 96-well plate. 20 μl of 6×MPBS was added to each well, and incubated at room temperature for 1 hour to block the phage prior to ELISA.

Flexible 96-well plates (Falcon) were coated overnight at 4° C. with human APRIL (1 μg/ml in PBS), BSA (1 μg/ml in PBS) or PBS alone. After coating, the solutions were removed from the wells, and the plates were blocked for 1 hour at room temperature in MPBS. The plates were washed 3 times with PBS and then 50 μl of preblocked phage was added to each well. The plates were incubated at room temperature for 1 hour and then washed with 3 changes of PBST followed by 3 changes of PBS.

To each well, 50 μl of an anti-M13-HRP conjugate (Pharmacia) at a 1 in 5000 dilution in MPBS was added and the plates incubated at room temperature for 1 hour. Each plate was washed three times with PBST followed by three times with PBS.

Fifty μl of TMB substrate was then added to each well, and incubated at room temperature for 30 minutes or until color development. The reaction was stopped by the addition of 25 μl of 0.5 M $H_2SO_4$. The signal generated was measured by reading the absorbance at 450 nm ($A_{450}$) using a microtitre plate reader (Bio-Rad 3550).

1483 antibodies were identified which bound APRIL but not to BSA or an uncoated well. 504, 259, 207, 271, and 242 positive phage were obtained from each of selection methods 1–5 described above, respectively.

Example 2

Specificity Phage ELISA

To determine the specificity of the scFvs, a phage ELISA was performed against APRIL, and a panel of related and unrelated antigens: BLyS, BCMA, TACI, LIGHT, TNF-α, BSA and an uncoated well.

Individual *E. coli* colonies containing phagemid were inoculated into 5 ml 2YTAG and incubated at 37° C. for 4 hours, shaking. M13K07 helper phage (Pharmacia) was added to each tube to an MOI of 10 and incubated for 30 min at 37° C. for 1 hour, the first 30 minutes static and the final 30 minutes with gentle shaking. Cells were pelleted by centrifugation at 3,500 rpm for 10 minutes. The phage containing supernatant (5 ml) was carefully transferred to a fresh tube, 1 ml of 6 MPBS added and then incubated at room temperature for 1 hour to pre-block the phage prior to ELISA.

Flexible 96-well plates (Falcon) were coated overnight at 4° C. with each antigen (1 μg/ml). All antigens were coated in PBS. After coating, the solutions were removed from the wells, and the plates were blocked for 1 hour at room temperature in MPBS. The plates were washed 3 times with PBS and then 50 μl of pre-blocked phage was added to each well. The plates were incubated at room temperature for 1 hour and then washed with 3 changes of PBST followed by 3 changes of PBS.

To each well, 50 μl of an anti-M13-HRP conjugate (Pharmacia) at a 1 in 5000 dilution in MPBS was added and the plates incubated at room temperature for 1 hour. Each plate was washed three times with PBST followed by three times with PBS.

Fifty μl of TMB substrate was then added to each well, and incubated at room temperature for 30 minutes or until color development. The reaction was stopped by the addition of 25 μl of 0.5 M $H_2SO_4$. The signal generated was measured by reading the absorbance at 450 nm ($A_{450}$) using a microtitre plate reader (Bio-Rad 3550).

The results for 2 typical clones, A004G02 and A019C11 are shown in FIG. 1. Both antibodies recognize APRIL but not BLyS, BCMA, TACI, LIGHT, TNF-α, BSA or the uncoated well. The control anti-BLyS antibody recognizes BLyS but shows no binding to APRIL. This indicates that the 2 antibodies, A004G02 and A019C11, specifically recognize APRIL.

Example 3

Binding Inhibition Assays

The potency of the antibodies in scFv form was assessed in 2 biochemical receptor binding inhibition assays. The ability of an scFv to inhibit the binding of biotinylated-APRIL to immobilized receptor can be quantitated. APRIL was biotinylated using NHS-biotin (Pierce) at a molar ratio of 20:1 biotin:APRIL. The biological activity of the biotinylated APRIL was confirmed using the receptor inhibition assay.

BCMA:Biotinylated-APRIL Inhibition Assay

APRIL binds to BCMA with higher affinity than its binds to TACI so, inhibition of biotinylated APRIL (bio-APRIL) binding to BCMA can be used to screen selection outputs as periplasmic extracts for neutralizers and then assess potency of the positives as purified scFvs. To perform this assay, each well of a black 96 well flat-bottomed plate (Costar) was coated with 1.25 ng BCMA fusion protein overnight at 4° C. The wells were blocked with 3% milk in PBS for an hour at room temperature. ScFv were then added in the presence of 5 ng/ml biotinylated APRIL for 90 minutes at room temperature. Binding of biotinylated APRIL was detected via streptavidin Delfia (Wallac) added at a 1:1000 dilution in Delfia assay buffer (Wallac). After an hour at room temperature this was read on a Wallac 1420 workstation at 620 nm. Unlabelled APRIL was titrated in each potency determination assay to ensure consistency and it had an average $IC_{50}$ of 48 pM. FIG. 2 shows the results for 3 typical clones A019C11, A034G03 and A010D09 alongside APRIL inhibiting binding to BCMA.

TACI:bio-APRIL Inhibition Assay

An assay similar to that described above can also be used to test if anti-APRIL antibodies of the invention are able to inhibit binding of bio-APRIL to TACI. In this case, the plate was coated with 2.5 ng TACI fusion protein per well and scFv were added in the presence of 50 ng/ml biotinylated APRIL instead of 5 ng/ml. Otherwise, the method was identical to that for the BCMA:bio-APRIL assay. When APRIL was titrated in this assay it had an average $IC_{50}$ of 1.3 nM, but gave partial inhibition to the binding of the bio-APRIL. It was also found that many of the clones inhibited the binding of bio-APRIL to TACI (and in some cases to BCMA as well) only partially. FIG. 3 shows the results for the same clones as above inhibiting binding to TACI.

Clone Tables

The results for 12 anti-APRIL antibodies were placed into 3 clone tables based on whether they inhibited both BCMA and TACI fully, BCMA fully and TACI partially or both receptors only partially. The tables are shown below with the antibodies listed in order of potency.

| Ranking | Clone | VH-CDR3 | $IC_{50}$ vs BCMA | $IC_{50}$ vs TACI |
|---|---|---|---|---|
| Full Inhibitors | | | | |
| 1 | A019C11 | GGRLAGSTVFTPAFEY | 4.3 nM | 10 nM |
| 2 | A013B07 | GGRLAGSTVFTPAFEY | 7.7 nM | 10 nM |
| 3 | A020F03 | GGRLAGSTVFTPAFEY | 12 nM | 3.5 nM |
| 4 | A004G02 | SNPQYDAFDI | 19 nM | 800 nM |
| Full BCMA, partial TACI inhibitors | | | | |
| 1 | A027A11 | GSQAFEI | 2.7 nM | 5.6 nM |
| 2 | A034G03 | GNTGPRPFDP | 6 nM | 36 nM |
| 3 | A034H05 | SGGDGYRDYGMDL | 10 nM | 13 nM |
| 4 | A053H04 | GNTGPRPFDP | 25 nM | 139 nM |
| 5 | A030D09 | SWYYDILTGYWDYYYMDV | 55 nM | 150 nM |
| Partial Inhibitors on BCMA and TACi | | | | |
| 1 | A010D09 | DLSRLGMDV | 2.3 nM | 12 nM |
| 2 | A027B01 | GISAGMDV | 3.1 nM | 94 nM |
| 3 | A024G01 | VSRTSYYDVLTDNNRYSYYMDV | 19 nM (3) | 4 nM (1) |

Example 4

Conversion of scFvs to IgG1 Format

The VH domain and the VL domains of scFvs that we wish to convert into IgG molecules are cloned into vectors containing the nucleotide sequences of the appropriate heavy (human IgG1) or light chain (human kappa or human lambda) constant regions such that a complete heavy or light chain molecule could be expressed from these vectors when transfected into an appropriate host cell. Further, when cloned heavy and light chains are both expressed in one cell line (from either one or two vectors), they can assemble into a complete functional antibody molecule that is secreted into the cell culture medium. Methods for converting scFvs into conventional antibody molecules are well known within the art.

Generation of NS0 Cell Lines Expressing Anti-APRIL Antibodies (IgG1)

Plasmids containing the heavy and light chains are separately linearized using the Pvu I restriction enzyme. The linearized DNAs are purified by phenol-chloroform extraction followed by ethanol precipitation and then resuspended in $H_2O$. NS0 cells ($10^7$) from a growing culture are electroporated (0.25 kV and 975 µF) in PBS with 12.5 µg linearized heavy chain plasmid DNA and 37.5 µg linearized light chain DNA. The cells are washed in 20 ml non-selective medium (10% FCS in DMEM supplemented with 6 mM glutamine, amino acids and penicillin/streptomycin) and then transferred in 12.5 ml medium into a T75 $cm^2$ flask and incubated overnight at 37° C., 5% $CO_2$/air. The day after transfection the cells are resuspended in selective medium containing 1 mg/ml geneticin and dispensed into 5×96-well plates at 200 µl/well. After 18 days at 37° C. (5% $CO_2$/air) colony supernatants are screened by ELISA that detects assembled human IgG in order to identify colonies expressing IgG. Positive colonies are expanded and adapted to growth in serum-free, selective medium. Duplicate T25 $cm^2$ flasks are set up. Cells from one flask are frozen down as a stock and cells in the second flask were grown to saturation. The productivity of the saturated cultures is assessed by ELISA. The highest producing cell lines are then selected for large-scale antibody production.

Large-scale IgG Production

The highest-producing cell lines are revived from frozen stocks and expanded to 400 ml in selective, serum-free medium in 2 liter roller bottles. The cells are grown at 37° C. and rolled at 4 rpm with the headspace being re-equilibrated with 5% $CO_2$/air every 2–3 days. Finally the culture is expanded to a 4 liter volume by addition of serum-free medium without selection (400 ml per 2 liter roller bottle). The cultures are then grown to saturation.

IgG Purification

The purification of the IgG from the fermentation broth is performed using a combination of conventional techniques commonly used for antibody production. Typically the culture harvest is clarified to remove cells and cellular debris prior to starting the purification scheme. This would normally be achieved using either centrifugation or filtration of the harvest. Following clarification, the antibody would typically be captured and significantly purified using affinity chromatography on Protein A Sepharose. The antibody is bound to Protein A Sepharose at basic pH and, following washing of the matrix, is eluted by a reduction of the pH. Further purification of the antibody is then achieved by gel filtration. As well as removing components with different molecular weights from the antibody this step can also be used to buffer exchange into the desired final formulation buffer.

Example 5

Antibody Neutralization of Murine Splenocyte Proliferation as Measured by 3HdT Incorporation To determine if an antibody inhibits APRIL mediated B cell proliferation, a splenocyte proliferation assay is performed Briefly, murine splenocytes are isolated by flushing spleen with complete medium using a 25G needle and 10 ml complete medium (RPMI 1640 with 10% FBS containing 100 U/ml penicillin, 100 µg/ml streptomycin, 4 mM glutamine, $5 \times 10^{-5}$ M β-mercaptoethanol). The cells are passed through a 100 micron nylon filter to remove cell clumps. The cell suspension is then ficolled at 400×g for 25 minutes at room temperature (one 15 ml conical tube/spleen; 3 ml ficol, 10 ml cell suspension/spleen; Ficol 1083 from Sigma). The recovered cells are washed 3 times in complete medium and counted. Recovered cells are then diluted to a concentration of $3 \times 10^6$/ml in complete medium containing a 3× concentration of SAC (3×=1:33,333 dilution of stock) (Staph. aureus Cowan strain; Calbiochem).

For each antibody, 50 µl of antibody dilutions at 30 µg/ml, 3.0 µg/ml, and 0.3 µg/ml concentrations are aliquotted into individual wells of a 96 well plate in triplicate. Suitable positive controls, such as, for example monoclonal antibody 15C10, are also used. Medium containing no antibody (and human isotype controls (purchased commercially) when necessary) are used as negative controls.

APRIL protein is diluted in complete medium to concentrations of 300 ng/ml, 90 ng/ml and 30 ng/ml. 50 µl of each of the APRIL dilutions are then added to the antibody dilution series in the plates. The plate containing the antibody and APRIL dilutions is then incubated for 30 minutes at 37° C., 5% $CO_2$, after which 50 µl of the splenocyte cell suspension containing SAC is added to all wells. The plates are then incubated for 72 hours (37° C., 5% $CO_2$).

After 72 hours, each well is supplemented with 50 µl complete medium containing 0.5 µCi $^3$H-thymidine (6.7 Ci/mM; Amersham) and cells are incubated for an additional 20–24 hours at (37° C., 5% $CO_2$). Following incubation cells are harvested using a Tomtec Cell Harvester and filters counted in a TopCount Scintillation counter (Packard).

The ability of an antibody of the present invention to inhibit splenocyte proliferation induced by APRIL/BLyS heterotrimers can also be assessed using the assay described above, wherein in APRIL/BLyS heterotrimeric protein is substituted for APRIL protein.

Example 6

Human B Cell Proliferation Assay for In Vitro Screening of APRIL Antagonist Molecules This bioassay for assessing the effects of putative APRIL antagonists is performed in triplicate in 96 well format by mixing equal volumes of APRIL, responder cells, and putative antagonist each of which is prepared as a 3× stock reagent.

B-lymphocytes are purified from human tonsil by MACS (anti-CD3 depletion), washed, and resuspended in complete medium (CM) (RPMI 1640 with 10% FBS containing 100 U/ml penicillin, 100 µg/ml streptomycin, 4 mM glutamine, $5 \times 10^{-5}$ M β-mercaptoethanol) at a concentration of $3 \times 10^6$ cells/ml. Staphylococcus aureus, Cowan I (SAC, CalBiochem) is added to cells at 3× concentration (3×=1:33,333 dilution of stock)

Meanwhile, eight serial dilutions (3-fold) of potential antagonist are prepared in CM such that the diluted antagonists are at 3× the final concentrations to be tested in the assay. Antibodies are routinely tested starting at a final concentration of 10 µg/ml and going down to about 1.5 ng/ml.

Human rAPRIL is prepared in CM to 3× concentration (3×=300 ng/ml, 30 ng/ml, and 3 ng/ml) in CM. Potential inhibitors are routinely tested at several concentrations of APRIL to avoid false negatives due to unexpectedly low affinity or antagonist concentration.

50 µl of diluted antagonist and 50 µl of diluted APRIL are added to the putative antagonist dilution series.

Cells are then incubated for 72 hours (37° C., 5% $CO_2$) in a fully humidified chamber. After 72 hours, the cells are supplemented with 0.5 µCi/well $^3$H-thymidine (6.7 Ci/mmol) and incubated for an additional 24 hours. Plates are harvested using a Tomtec Cell Harvester and filters counted in a TopCount Scintillation counter (Packard).

The ability of an antibody of the present invention to inhibit splenocyte proliferation induced by APRIL/BLyS heterotrimers can also be assessed using the assay described above, wherein in APRIL/BLyS heterotrimeric protein is substituted for APRIL protein.

Example 7

Antibody Production and Purification

The following example describes a large scale antibody production and purification methods that may be used to make antibodies of the present invention. One of skill in the art will be aware of routine modifications to the protocol described below, for example, as regards column choice, column, loading, wash, and elution buffers, and pH.

Cell Culture Scale-up and Antibody Production

A serum-free and animal source-free growth medium (HGS-NS0SF) is used from thawing cells through scale-up to the production bioreactor. The HGS-NS0SF growth medium is prepared by adding 20 mL/L GS supplement and 1 mL/L cholesterol (synthetic) lipid concentrate into 1 L CD hybridoma media without 1-glutamine (Invitrogen/Life technologies). The media are stored at 2–8° C. until use.

Thawing Cells from MCB Vial(s)

Approximately $16 \times 10^6$ cells are thawed at 37° C. in a water bath. The cells are transferred into T-225 culture flask(s) to yield approximately 50 mL working volume with an inoculation density of approximately $3.0 \times 10^5$ cells/mL. The culture flask(s) is then placed in a humidified $CO_2$ incubator at 37° C. with 5% $CO_2$ for 4 days.

First Expansion(s) of Culture in Spinner Flask

The culture is aseptically expanded into a 500 mL spinner flask to give approximately 300 mL working volume, at an inoculation cell density of approximately $2.2 \times 10^5$ cells/mL. The spinner flask is then placed on magnetic stirrers in a humidified $CO_2$ incubator at 37° C. with 5% $CO_2$ for 4 days. The agitation rate for the spinner flask is 80 rpm.

The culture is again expanded aseptically into one 3000 mL spinner flask to give approximately 1500 mL working volume, at an inoculation cell density of approximately $2.2 \times 10^5$ cells/mL. The spinner flask is then placed on magnetic stirrers in a humidified $CO_2$ incubator at 37° C. with 5% $CO_2$ for 4 days. The agitation rate for the spinner flasks is 80 rpm. If a sufficient amount of cell culture is accumulated to inoculate the seed bioreactor, proceed to Step 4. If not, the culture is expanded aseptically into multiple 3000 mL spinner flasks for a total of 3 to 4 expansions, until a sufficient amount of cell culture is accumulated to inoculate the seed bioreactor.

Seed Culture

The seed bioreactor is equipped with 2 impellers for mixing, a dissolved oxygen probe, a temperature probe, a pH probe, aseptic sampling and additional systems. The first step of the cell cultivation process is the addition of HGS-NS0SF media into the bioreactor. After the HGS-NS0SF media temperature reaches 37±0.5° C., the dissolved oxygen (DO) and pH levels are stabilized by addition of $N_2$ and $CO_2$ to decrease dissolved oxygen concentration to 30±5% air saturation, and obtain a pH of 7.20±0.10. The agitation rate is 80 rpm. The pooled cell culture is transferred aseptically to a 15 L seed bioreactor containing sterile HGS-NS0SF growth media to yield a culture with an inoculation cell density of approximately $2.2 \times 10^5$ cells/mL. During the cultivation process the temperature is maintained via a heat blanket and a cooling finger, the oxygen concentration is maintained via sparger and surface aeration, and pH is controlled by addition of $CO_2$ gas to lower the pH. The cultivation period is 5–6 days. The bioreactor air vents are protected by hydrophobic 0.2 μm vent filters.

Production Culture

The production bioreactor is equipped with 2 impellers for mixing, 2 dissolved oxygen probes, a temperature probe, 2 pH probes, aseptic sampling and additional systems. 80 L of HGS-NS0SF growth media is aseptically transferred into the 100 L production bioreactor. After the HGS-NS0SF growth media temperature reaches 37±0.5° C., the DO and pH levels are stabilized by addition of $N_2$ and $CO_2$ to decrease dissolved oxygen concentration to 30±5% air saturation, and obtain a pH of 7.20±0.10. The agitation rate is 45 rpm. The 15 L seed culture is aseptically transferred into the production bioreactor to yield a culture with an inoculation cell density of approximately $2.2 \times 10^5$ cells/mL. During the cultivation process the temperature is maintained via a heat exchanger, the oxygen concentration is maintained via sparger and surface aeration, and pH is controlled by addition of $CO_2$ gas to lower the pH. On day 3 after inoculation when cell density reaches approximately $1.0 \times 10^6$ cells/mL, approximately 6 L of HGS-NS0SF fed-batch media was fed into the production bioreactor. The production culture containing the antibody was harvested on Day 5 after feeding.

Recovery and Purification

Harvest of Cell Supernatant

Cell supernatant, (e.g., culture supernatant from NS0 cells expressing antibodies of the invention) is harvested on day 5 or 6 post final feeding in the final production bioreactor using a fed-batch cell culture process. The harvest process is started when the antibody concentration of at least 400 mg/L is attained. Cell culture temperature in the production bioreactor is cooled down to 15° C. at the time of harvest and maintained at that temperature during the recovery. A depth filtration process is used for cell removal and antibody recovery. The filtration process train consists of 4.5 μm, 0.45 μm and 0.2 μm pore size filters connected in series. A constant flow rate of 1.00 L/min is maintained during the operation with a cross-filter-pressure control of up to 15 psi. The 0.2 μm filtered culture supernatant is collected in a process bag and transferred for purification.

The purification process is conducted at 22 to 26° C.

Chromatography on MEP HyperCEL HCIC Column

The culture supernatant is loaded onto a MEP HyperCEL™ column, a Hydrophobic charge interaction chromatography, HCIC, available from Ciphergen Biosystems, or equivalent column that is equilibrated in 50 mM Tris, 0.5 M sodium chloride, pH 7.5. The MEP column is washed with 25 mM sodium citrate, 0.15 M sodium chloride, pH 6.4 and eluted with 25 mM sodium citrate, 0.15 M sodium chloride, pH 4.4. The elution is monitored by ultraviolet (UV) absorbance at 280 nm. The peak fractions are collected, analyzed by $A_{280}$ and SDS-PAGE. Appropriate fractions are pooled.

Virus Inactivation

The eluate from the MEP column is adjusted with 1 M citric acid to pH 3.4±0.2 and allowed to stand for 45–60 minutes for viral inactivation. The solution is then re-adjusted to pH 5.0 with 1 M Tris base.

Chromatography on SP Sepharose FF Column

The inactivated eluate from the MEP column is diluted with water for injection (WFI) to a conductivity of 5 mS/cm, and loaded onto a SP Sepharose FF (cation exchange chromatography, Amersham-Pharmacia) column, or equivalent column equilibrated with 65 mM sodium acetate, pH 5.0. The antibody is eluted from the SP column with 20 mM sodium citrate, 0.15 M sodium chloride, 1.9% glycine, pH 7.1. The elution is monitored by ultraviolet (UV) absorbance at 280 nm. Peak fractions are collected and analyzed by $A_{280}$ and SDS-PAGE. Appropriate fractions are pooled.

Virus Removal Filtration, Diafiltration and Concentration

The eluate from the SP Sepharose FF column is filtered through a sequentially connected 0.2 μm filter and a Pall DV50 viral removal filter. The DV50 filtrate is placed into a 30 kD MW cut-off membrane device (Millipore Pellicon) to concentrate to a target concentration of 35–40 mg/mL, and diafiltered against 10 mM sodium citrate, 1.9% glycine, 0.5% sucrose, pH 6.5. The diafiltered material is monitored by $A_{280}$. The diafiltered bulk is 0.2 μm filtered and stored at 2–8° C. up to 24 hours.

Chromatography on Q Sepharose FF Column

The diafiltered TRM-1 solution is passed over a Q Sepharose FF column (anion exchange chromatography, Amersham-Pharmacia) or equivalent column equilibrated with 10 mM sodium citrate, 1.9% glycine, 0.5% sucrose, pH 6.5. The antibody is collected in the flow-through and monitored by $A_{280}$. Appropriate fractions are pooled and the final target concentration is 25 mg/mL.

Bulk Formulation, Filtration and Bulk Drug Substance Fill

Polysorbate 80 (2% stock solution) is pre-filtered through a 0.2 μm filter and added to the antibody solution from step 7 to a final concentration of 0.02%. The purified antibody is aseptically filtered under a laminar flow hood through a 0.2 μm filter and filled into polypropylene containers.

Storage of Bulk Drug Substance

The bulk drug substance is stored at 2–8° C. (short-term storage) or at or below −65° C. (long-term storage) prior to the release of the product. In-process testing of the unprocessed production bioreactor culture at harvest for each batch and in-process testing during the purification process are performed. The bioreactor is sampled aseptically and the culture is tested at various times throughout cultivation for cell density, viability and nutrient determination to ensure consistency of material being supplied for purification. The purification process is monitored at each step. Appearance is checked by visual inspection. The protein concentration is determined by Absorbance at 280 nm. The pH of the material is checked. Purity is checked, for example, by SDS-PAGE and size exclusion chromatography. An ELISA may be performed to check the ability of the antibody to bind its antigen. The biological activity of the antibody is also monitored. Residual DNA content, Endotoxin levels, and the bioburden (the number of viable organisms present in the antibody preparation) are all monitored and kept at or below standard acceptable levels. Additionally the oligosaccharide content may be analyzed; the peptide sequence of the antibody chains may also be analyzed using N-terminal sequencing and peptide mapping. Short and long-term studies of antibody stability may also be performed.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference.

Further, the Sequence Listing submitted herewith, in both computer and paper forms, is hereby incorporated by reference in its entirety.

The entire disclosure (including the specification, sequence listing, and drawings) of the following U.S. application is herein incorporated by reference in its entirety: Application No. 60/293,100 filed May 24, 2001.

What is claimed is:

1. An isolated antibody or fragment thereof comprising a VH domain and a VL domain whose amino acid sequences are each at least 95% identical to the amino sequences of the VH domain and the VL domain, respectively, of the scFv of any one of SEQ ID NOS:13–24 wherein said antibody or fragment thereof immunospecifically binds APRIL.

2. The antibody or fragment thereof of claim 1, wherein said antibody or fragment thereof inhibits APRIL binding to both BCMA and TACI.

3. The antibody or fragment thereof of claim 2 wherein the scFv is the scFv of any one of SEQ ID NOS:13–15.

4. The antibody or fragment thereof of claim 1, wherein said antibody or fragment thereof inhibits APRIL binding to BCMA and partially inhibits APRIL binding to TACI.

5. The antibody or fragment thereof of claim 4 wherein the scFv is the scFv of any one of SEQ ID NOS:16–20.

6. The antibody or fragment thereof of claim 1, wherein said antibody or fragment thereof partially inhibits APRIL binding to both BCMA and TACI.

7. The antibody or fragment thereof of claim 6 wherein the scFv is the scFv of any one of SEQ ID NOS:21–24.

8. The antibody or fragment thereof of claim 1, that binds APRIL purified from a cell culture wherein the cells in said cell culture comprise a polynucleotide encoding amino acids 1 to 250 of SEQ ID NO:37 operably associated with a regulatory sequence that controls gene expression.

9. The antibody or fragment thereof of claim 1 comprising the amino acid sequence of the VH domain and the amino acid sequence of the VL domain of the scFv of any one of SEQ ID NOS:13–24.

10. The antibody or fragment thereof of claim 9, wherein the scFv is the scFv of SEQ ID NO:13.

11. The antibody or fragment thereof of claim 9, wherein the scFv is the scFv of SEQ ID NO:14.

12. The antibody or fragment thereof of claim 9 wherein the scFv is the scFv of SEQ ID NO:15.

13. The antibody or fragment thereof of claim 9 wherein the scFv is the scFv of any one of SEQ ID NOS:16–20.

14. The antibody or fragment thereof of claim 9 wherein the scFv is the scFv of any one of SEQ ID NOS:21–24.

15. The antibody or fragment thereof of claim 9, that binds APRIL purified from a cell culture wherein the cells in said cell culture comprise a polynucleotide encoding amino acids 1 to 250 of SEQ ID NO:37 operably associated with a regulatory sequence that controls gene expression.

16. The antibody or fragment thereof of claim 1 wherein the antibody or fragment thereof is selected from the group consisting of:
    (a) a whole immunoglobulin molecule;
    (b) an scFv;
    (c) a monoclonal antibody;
    (d) a human antibody;
    (e) a chimeric antibody;
    (f) a Fab fragment;
    (g) an Fab' fragment;
    (h) an F(ab')2;
    (i) an Fv; and
    (j) a disulfide linked Fv.

17. The antibody or fragment thereof of claim 1 which comprises a heavy chain immunoglobulin constant domain selected from the group consisting of:
    (a) a human IgM constant domain;
    (b) a human IgG1 constant domain;
    (c) a human IgG2 constant domain;
    (d) a human IgG3 constant domain;
    (e) a human IgG4 constant domain; and
    (f) a human IgA constant domain.

18. The antibody or fragment thereof of claim 1 which comprises a light chain irnmunoglobulin constant domain selected from the group consisting of:
    (a) a human Ig kappa constant domain; and
    (b) a human Ig lambda constant domain.

19. The antibody or fragment thereof of claim 1 wherein the antibody or fragment thereof has a dissociation constant ($K_D$) selected from the group consisting of:
    (a) a dissociation constant ($K_D$) between $10^{-7}$ M (inclusive) and $10^{-8}$ M; and
    (b) a dissociation constant ($K_D$) between $10^{-8}$ M (inclusive) and $10^{-9}$ M.

20. The antibody or fragment thereof of claim 1 wherein the antibody or fragment thereof has a dissociation constant ($K_D$) of less than or equal to $10^{-9}$ M.

21. The antibody or fragment thereof of claim 20 wherein the antibody or fragment thereof has a $K_D$ between $10^{-9}$ M and 10–10 M.

22. The antibody or fragment thereof of claim 20 wherein the antibody or fragment thereof has a $K_D$ between $10^{-10}$ M (inclusive) and $10^{-11}$ M.

23. The antibody or fragment thereof of claim 20 wherein the antibody or fragment thereof has a $K_D$ between $10^{-11}$ M (inclusive) and $10^{-12}$ M.

24. The antibody or fragment thereof of claim 1 wherein the antibody or fragment thereof is conjugated to a detectable label.

25. The antibody or fragment thereof of claim 24, wherein the detectable label is a radiolabel.

26. The antibody or fragment thereof of claim 25, wherein the radiolabel is $^{125}$I, $^{131}$I, $^{111}$In, $^{90}$Y, $^{99}$Tc, $^{177}$Lu, $^{166}$Ho, or $^{153}$Sm.

27. The antibody or fragment thereof of claim 24, wherein the detectable label is an enzyme, a fluorescent label, a luminescent label, or a bioluminescent label.

28. The antibody or fragment thereof of claim 1 wherein the antibody or fragment thereof is biotinylated.

29. The antibody or fragment thereof of claim 1 wherein the antibody or fragment thereof is conjugated to a therapeutic or cytotoxic agent.

30. The antibody or fragment thereof of claim 29, wherein the therapeutic or cytotoxic agent is selected from the group consisting of:
   (a) an anti-metabolite;
   (b) an alkylating agent;
   (c) an antibiotic;
   (d) a growth factor;
   (e) a cytokine;
   (f) an anti-angiogenic agent;
   (g) an anti-mitotic agent;
   (h) an anthracycline;
   (i) toxin; and
   (j) an apoptotic agent.

31. The antibody or fragment thereof of claim 1 wherein the antibody or fragment thereof is attached to a solid support.

32. The antibody or fragment thereof of claim 1 wherein the antibody or fragment thereof immunospecifically binds APRIL in a Western blot.

33. The antibody or fragment thereof of claim 1 wherein the antibody or fragment thereof immunospecifically binds APRIL in an ELISA.

34. An isolated cell that produces the antibody or fragment thereof of claim 9.

35. The antibody or fragment thereof of claim 1 wherein the antibody or fragment thereof diminishes the ability of APRIL to stimulate immunoglobulin production.

36. The antibody or fragment thereof of claim 1 wherein the antibody or fragment thereof diminishes the ability of APRIL to stimulate B cell proliferation.

37. The antibody or fragment thereof of claim 1 wherein the antibody or fragment thereof diminishes the ability of APRIL to stimulate B cell differentiation.

38. The antibody or fragment thereof of claim 1 wherein the antibody or fragment thereof diminishes the ability of APRIL to stimulate B cell survival.

39. The antibody or fragment thereof of claim 1 in a pharmaceutically acceptable carrier.

40. A kit comprising the antibody or fragment thereof of claim 1.

41. The kit of claim 40 comprising a control antibody.

42. The kit of claim 40, wherein the antibody or fragment thereof is coupled or conjugated to a detectable label.

43. The antibody or fragment thereof of claim 9, wherein the scFv is the scFv of SEQ ID NO:16.

44. The antibody or fragment thereof of claim 9, wherein the scFv is the scFv of SEQ ID NO:17.

45. The antibody or fragment thereof of claim 9, wherein the scFv is the scFv of SEQ ID NO:18.

46. The antibody or fragment thereof of claim 9, wherein the scFv is the scFv of SEQ ID NO:19.

47. The antibody or fragment thereof of claim 9, wherein the scFv is the scFv of SEQ ID NO:20.

48. The antibody or fragment thereof of claim 9, wherein the scFv is the scFv of SEQ ID NO:21.

49. The antibody or fragment thereof of claim 9, wherein the scFv is the scFv of SEQ ID NO:22.

50. The antibody or fragment thereof of claim 9, wherein the scFv is the scFv of SEQ ID NO:23.

51. The antibody or fragment thereof of claim 9, wherein the scFv is the scFv of SEQ ID NO:24.

52. An isolated antibody or fragment thereof comprising the amino acid sequences of each of the VHCDR1, VHCDR2, VHCDR3, VLCDR1, VLCDR2 and VLCDR3 of a single scFv of any one of the scFvs of SEQ ID NOS:13–24, wherein said antibody or fragment thereof immunospecifically binds APRIL.

* * * * *

UNITED STATES PATENT AND TRADEMARK OFFICE
CERTIFICATE OF CORRECTION

PATENT NO. : 7,189,820 B2  Page 1 of 1
APPLICATION NO. : 10/151882
DATED : March 13, 2007
INVENTOR(S) : Steven M. Ruben It is certified that error appears in the above-identified patent and that said Letters Patent is hereby corrected as shown below:

On the Title page:
At INID (75) Inventor, "Steven M. Ruben, Olney, MD (US)" should read Steven M. Ruben, Brookeville, MD (US)--.

In the Specification:
At column 1, line 45, "(CDT0) by" should read --(CD70) by--.

In the Claims:
In Claim 21, "and 10-10 M." should read --and $10^{-10}$ M.--.
In Claim 31, "aftached" should read --attached--.

Signed and Sealed this

Eleventh Day of December, 2007

JON W. DUDAS
*Director of the United States Patent and Trademark Office*

SEQUENCE LISTING

<160> NUMBER OF SEQ ID NOS: 48

<210> SEQ ID NO 1
<211> LENGTH: 758
<212> TYPE: DNA
<213> ORGANISM: Artificial Sequence
<220> FEATURE:
<223> OTHER INFORMATION: DNA encoding A019C11 and A020F03 scFv

<400> SEQUENCE: 1

```
gaggtgcagc tggtgcagtc tggggctgag gtgaagaagc ctggggcctc agtaaaggtc      60
tcgtgcaaga cttctggata caccttcacc gacaactata tgcactgggt gcggcaggcc    120
cctggccaag ggcttgagtg gatgggatgg atcagtccta acagtagtac cacactctat    180
gcacagaagt ttcggggcag ggtcacgttg accaggggaca cgtccgtcag cacagcctac    240
atggagctga gcgggctgga ttctgacgac acggccctct atttctgtgc gagaggaggc    300
cgccttgcgg gttctacagt gtttactcct gcctttgaat actggggccg ggggacaatg    360
gtcaccgtct cgagtggagg cggcggttca ggcggaggtg gctctggcgg tggcggaagt    420
gcacaggctg tgctgactca gccgtcctcg gtgtctgaag cccccaggca gagggtcacc    480
atctcctgtt ctggaagcag ctccaacatc ggaaataatg ctgtaaagtg gtaccagcag    540
ctcccaggaa aggctcccaa actcctcatc tattatgatg atctgctgcc ctcagggtc      600 tctgaccgat tctctggctc taagtctggc acctcagcct ccctggccat cagtgggctc    660
cagtctgagg atgaggctga ttattactgt gcagcatggg atgacagcct gaatggttat    720
gtcttcggaa ctgggaccaa ggtcaccgtc ctaggtgc                            758
```

<210> SEQ ID NO 2
<211> LENGTH: 756
<212> TYPE: DNA
<213> ORGANISM: Artificial Sequence
<220> FEATURE:
<223> OTHER INFORMATION: DNA encoding A013B07 scFv

<400> SEQUENCE: 2

```
gaagtgcagc tggtgcagtc tggggctgaa gtgaagaagc ctggggcctc agtaaaggtc      60
tcgtgcaaga cttctggata caccttcacc gacaactata tgcactgggt gcggcaggcc    120
```

-continued

```
cctggccaag ggcttgagtg gatgggatgg atcagtccta acagtagtac cacactctat    180
gcacagaagt ttcggggcag ggtcacgttg accaggaca cgtccgtcag cacagcctac     240
atggagctga gcgggctgga ttctgacgac acggccctct atttctgtgc gagaggaggc    300
cgccttgcgg gttctacagt gtttactcct gcctttgaat actggggcca agggacaatg    360
gtcaccgtct cgagtggagg cggcggttca ggcggaggtg gctctggcgg tggcggaagt    420
gcacagtctg tgctgactca gccacccctcg gtgtctgaag cccccaggca gagggtcacc   480
atctcctgtt ctggaagcag ttccaacatc ggagccaatg ctgtaaactg gtaccagcag    540
ctcccaggaa aggctcccaa actcctcatc tattttgatg atctgttgcc ctcagggtc    600 tctgaccgat tctctggctc caagtctggc acctcagcct ccctggccat cagtgggctc    660
cagtctgagg atgaggctga ttattactgt gcagcatggg atgacagcct gaatggtgtg    720
gtattcggcg gagggaccaa gctgaccgtc ctaggt                              756
```

<210> SEQ ID NO 3
<211> LENGTH: 735
<212> TYPE: DNA
<213> ORGANISM: Artificial Sequence
<220> FEATURE:
<223> OTHER INFORMATION: DNA encoding A004G02 scFv

<400> SEQUENCE: 3

```
caggtgcagc tggtgcagtc tggggctgag gtgaagaagc ctgggtcctc ggtgaaggtc    60
tcctgcaagg cttctggagg caccttcagc agttatggta tcagtgggt gcgacaggcc    120 cctggacaag ggcttgagtg gatgggaggg atcatcccta tctttggtac agcaaactac    180
gcacagaagt tccagggcag agtcacgatt accgcggacg aatacacgag cacagcctat    240
atggagctga gcagcctgag atctgaggac acggccgtgt attactgtgc gaggtccaac    300 cccagtatg atgcttttga tatctgggc caggggacca cggtcaccgt ctcctcaggt    360
ggaggcggtt caggcggagg tggcagcggc ggtggcggat cgtcctatgt gctgactcag    420 ccccccctcag tgtctgggac ccccgggcag agagtcaccg tctcttgttc tggaggcaga    480
tccaacatcg gcagtaatac tgtaaagtgg tatcagcagc tcccaggaac ggccccaaa    540 ctcctcatct atggcaatga tcagcggccc tcaggggtcc ctgatcgctt ctctggctcc    600
aagtctggca acacggcctc cctgaccgtc tctgggctcc aggttgagga tgaggctgat    660
tattactgcc agtcctatga cagcagcctg aggggttcgg tgttcggcgg agggaccaag    720
ctgaccgtcc taggt                                                     735
```

<210> SEQ ID NO 4
<211> LENGTH: 726
<212> TYPE: DNA
<213> ORGANISM: Artificial Sequence
<220> FEATURE:
<223> OTHER INFORMATION: DNA encoding A027A11 scFv

<400> SEQUENCE: 4

```
caggtacagc tgcagcagtc aggggctgag gtgaagaagc ctgggtcctc ggtgaaggtc    60
tcctgcaagg cttctggagg caccttcagc acgtatgcta tcacctgggt gcgacaggcc    120
cctggacagg ggcttgagtg gatggagac atcatccctg tctttggtat accaaactac    180
gcacagatgt tccaggacag agtcacgatt accgcggacg aatccacgag cacagcctac    240
ctggagctga acagcctggg agccgaggac acggctgtgt attactgtgc gagaggttcc    300
caagcttttg agatctgggg gaaagggacc acggtcaccg tctcctcagg tggaggcggt    360
```

```
tcaggcggag gtggcagcgg cggtggcgga tcgcagtctg tgctgactca gcctgcctcc      420
gtgtctgggt ctcctggaca gtcgatcacc atctcctgca ctggaaccag cagtgacgtt      480
ggtggttata actatgtctc ctggtaccaa caacacccag gcaaagcccc caaactcatg      540
atttatgagg gcagtaagcg gccctcaggg gtttctaatc gcttctctgg ctccaagtct      600
ggcaacacgg cctccctgac aatctctggg ctccaggctg aggacgaggc tgattattac      660
tgcagctcat atacaaccag gagcactcga gttttcggcg agggaccaa gctgaccgtc       720 ctaggt                                                                 726

<210> SEQ ID NO 5
<211> LENGTH: 744
<212> TYPE: DNA
<213> ORGANISM: Artificial Sequence
<220> FEATURE:
<223> OTHER INFORMATION: DNA encoding A034G03 scFv

<400> SEQUENCE: 5
caggtacagc tgcagcagtc aggggctgag gtgaagaagc ctgggtcctc ggtgaaggtc       60
tcctgcaagg cttctggagg caccttcagc aactatgcta tcagctgggt gcgacaggcc      120
cctggacaag gcttgagtg gatgggaggg atcatccctc tctttgacac acctaactac       180
gcacagaagt tccagggcag agtcacgatt accgcggacg aatccacgag cacagcctac      240
atggagctga gcagcctgag atctgaggac acggccgtct attactgtgc gagaggaaat      300
actgccccga gacccttcga cccctggggc caaggcaccc tggtcaccgt ctcgagtgga      360
ggcggcggtt caggcggagg tggctctggc ggtggcggaa gtgcacaggc tgtgctgact      420
cagccgtcct cagtttctgg ggccccaggg cagagggtca ccatctcctg cagtgcgacc      480
agccccaaca tcgggcagg agatgaaata cactggtacc aagtgtctcc aggaaaagcc       540
cccaaactcc tcatctatgg tgacatcaag cggccctcag ggtttctga ccgattctct       600 ggctccaagt ctgggaccac agcctccctg gccatcactg gctccgacc agaggatgag       660 gctgattatt actgccagtc gtatgacagg accctgagtg ggagtgtggt attcggcgga      720
gggaccaagg tcaccgtcct aggt                                             744

<210> SEQ ID NO 6
<211> LENGTH: 747
<212> TYPE: DNA
<213> ORGANISM: Artificial Sequence
<220> FEATURE:
<223> OTHER INFORMATION: DNA encoding A034H05 scFv

<400> SEQUENCE: 6
gaggtgcagc tggtgcagtc tggggctgag gtgaagaagc ctgggtcctc agtgaaagtc       60
tcctgcaaag tttctggtgg cagtttcccc aactatgcta tcaactgggt gcgacaggcc      120
cctggacagg gccttgagtg gatgggaagc ctcgtccctg tctttcttac accaaactac      180
gcagagaggt tccaagacag agtcaccatt actgcggacg aatcaacgag tacagcctac      240
atggagctga ggagcctcag atctgacgac acggccgtct ctattgtgc gagatcgggc       300 ggagatggct acagagatta cggtatggac ctctggggcc ggggaaccct ggtcaccgtc      360
tcgagtggag gcggcggttc aggcggaggt ggctctggcg gtggcggaag tgcacagtct      420
gtgctgacgc agccgccctc agcgtctggg acccccgggc agagggtcac catctcttgt      480
tctggaagca gctccaacat cggaaggaat actgtaaact ggttccaaca actcccagga      540
```

```
acggccccca aactcctcat ctatagtagt aatcagcggc cctcagggt cctgaccga      600 ttcgctggct ccaagtctgg cacctcagcc tccctggcca tcagtgggct ccagtctgag     660
gatgaggctg attattactg tgcagcatgg gatgacagcc tgaatggtct tgtattcggc     720
ggagggacca agctgaccgt cctaggt                                         747
```

<210> SEQ ID NO 7
<211> LENGTH: 744
<212> TYPE: DNA
<213> ORGANISM: Artificial Sequence
<220> FEATURE:
<223> OTHER INFORMATION: DNA encoding A053H04 scFv

<400> SEQUENCE: 7

```
gaagtgcagc tggtgcagtc tggggctgag gtgaagaagc tggggtcctc ggtgaaggtc      60
tcctgcaagg cttctggagg caccttcagc aactatgcta tcagctgggt gcgacaggcc     120
cctggacaag gcttgagtg gatgggaggg atcatccctc tctttgacac acctaactac     180
gcacagaagt tccagggcag agtcacgatt accgcggacg aatccacgag cacagcctac     240
atggagctga gcagcctgag atctgaggac acggccgtct attactgtgc gagaggaaat     300
actggcccga gaccccttcga ccctggggg aagggaccca cggtcaccgt ctcgagtgga     360
ggcggcggtt caggcggagg tggctctggc ggtggcggaa gtgcacaggc tgtgctgact     420
cagccgtcct cagtgtctgg ggccccaggg cagagggtca ccgtctcctg cactgggagc     480
agctccaaca tcggggcagg ttatgagtta aactggtacc agcaacttcc aggaacagcc     540
cccaaactcc tcatctatgg tgacaccaat cggccctcag gggtccctga ccgattctct     600
ggctccaagt ctggcacctc agcctccctg gccatcactg gctccaggc tgaggatgag     660 gctaattatt actgccagtc ctatgacagc ggtcgggtg gtcctgtggt attcggcgga    720
gggaccaagc tgaccgtcct aggt                                            744
```

<210> SEQ ID NO 8
<211> LENGTH: 750
<212> TYPE: DNA
<213> ORGANISM: Artificial Sequence
<220> FEATURE:
<223> OTHER INFORMATION: DNA encoding A030D09 scFv

<400> SEQUENCE: 8

```
caggtacagc tgcagcagtc aggggctgag gtgaagaagc ctggggtcctc ggtgaaagtc     60 tcctgcaaga cttctggagg cgcgttcagt cattatgcta tccactgggt gcgactggcc    120
cctggacaag gcttgagtg gatgggagac atcatccctg tctatggttc aacaacctac    180
gcacagaaat tccaggacag agtcacaatt agcgcggacg aatccacgag cactgcctac    240
atggaactga gcagcctgag atctgaggac acggccgtgt attactgtgc gagaagctgg    300
tattacgata ttttgactgg ttattgggac tactactaca tggacgtctg ggcaaggga    360 acccctggtca ccgtctcgag tggtggaggc ggttcaggcg gaggtggcag cggcggtggc    420
ggatcgtctg agctgactca ggaccctgct gtgtctgtgg ccttgggaca gacagtcagg    480
atcacatgcc aaggagacag cctcagaagc tattatgcaa gctggtacca gcagaagcca    540
ggacaggccc ctgtacttgt catctatggt aaaaacaacc ggccctcagg gatcccagac    600
cgattctctg gctccagctc aggaaacaca gcttccttga ccatcactgg gctcaggcg    660 gaagatgagg ctgactatta ctgtaactcc cggacagca gtggtaacca tgtggtattc    720
ggcggaggga ccaagctgac cgtcctaggt                                     750
```

<210> SEQ ID NO 9
<211> LENGTH: 723
<212> TYPE: DNA
<213> ORGANISM: Artificial Sequence
<220> FEATURE:
<223> OTHER INFORMATION: DNA encoding A010D09 scFv

<400> SEQUENCE: 9

```
caggtgcagc tggtgcagtc tggggctgag gtgaagaagc ttgggtcctc ggtgaaggtc    60
tcctgcaagg cttctggagg cacc ttcagc agctatgcta tcagctgggt gcgacaggcc   120
cctggacaag ggcttgagtg gatgggaggg atcatccc ta tctttggtac agcaaactac   180
gcacagaagt tccagggcag agtcacgatt accgcggacg aatccacgag cacagcctac   240
atggagctga gcagcctgag atctgaggac acggccgtgt attactgtgc aagagatctg   300
agcaggctcg gtatggacgt ctggggccaa gggaccacgg tcaccgtctc ctcaggtgga   360
ggcggttcag gcggaggtgg cagcggcggt ggcggatcgg acatccagat gacccagtct   420
ccttccaccc tgtctgcatc tattggagac agagtcacca tcacctgccg ggccagtgag   480
ggtatttatc actggttggc ctggtatcag cagaagccag ggaaagcccc taaactcctg   540
atctataagg cctctagttt agccagtggg gccccatcaa ggttcagcgg cagtggatct   600
gggacagatt tcactctcac catcagcagc ctgcagcctg atgatttgc aacttattac   660
tgccaacaat atagtaatta tccgctcact ttcggcggag ggaccaagct ggagatcaaa   720
cgt                                                                 723
```

<210> SEQ ID NO 10
<211> LENGTH: 720
<212> TYPE: DNA
<213> ORGANISM: Artificial Sequence
<220> FEATURE:
<223> OTHER INFORMATION: DNA encoding A027B01 scFv

<400> SEQUENCE: 10

```
caggtgcagc tgttgcagtc tgcggctgag gtgaagaagc ctgggtcctc ggtaaaggtc    60
tcctgcaaga cttctggagg cacc ttcaga aatcatgcta tcagttgggt gcgacaggcc   120
cctggacaag ggcttgagtg gatgggaggg atcatccc ta tctttggtac agcaaactac   180
gcacagaagt tccagggcag agtcacgatt accgcggacg aatccacgag cacagcctac   240
atggagctga gcagcctgag atctgaggac acggccgtgt attactgtgc gaggggata    300
tcggctggta tggacgtctg gggccgagga accctggtca ccgtctcctc aggtggaggc   360
ggttcaggcg gaggtggcag cggcggtggc ggatcggaca tccagatgac ccagtctcca   420
tccttcctgt ctgcatctat tggagacaga gtcaccatca cctgccgggc cagtgagggt   480
atttatcact ggttggcctg gtatcagcag aagccaggga agcccctaa actcctgatc    540
tataaggcct ctagtttagc cagtggggcc ccatcaaggt tcagcggcag tggatctggg   600
acagatttca ctctcaccat cagcagcctg cagcctgatg attttgcaac ttattactgc   660
caacaatata gtaattatcc gctcactttc ggcggaggga ccaagctgga gatcaaacgt   720
```

<210> SEQ ID NO 11
<211> LENGTH: 717
<212> TYPE: DNA
<213> ORGANISM: Artificial Sequence
<220> FEATURE:
<223> OTHER INFORMATION: DNA encoding A027H08 scFv

<400> SEQUENCE: 11

```
caggtacagc tgcagcagtc aggggctgag gtgaagaagc ctgggtcctc ggtgaaggtc      60
tcctgcaagg cttctggagg caccttcagc agctatgcta tcagctgggt gcgacagacc     120
cctggacaag ggcttgagtg gatgggaggg atcatcccta tctttggtgc agcaaactac     180
gcacagaagt tccagggcag agtcacgatt accgcggacg aatccacgag cacagcccac     240
atggagctga gcagcctgag atctgaggac acggccgtgt attactgcgc gagagggata     300
tctggtggta tggacgtctg ggcaagggc accctggtca ccgtctcgag tggaggcggt     360
tcaggcggag gtggcagcgg cggtggcgga tcggacatcc agatgaccca gtctccttcc     420
accctgtctg catctattgg agacagagtc accatcacct gccgggccag tgagggtatt     480
tatcactggt tggcctggta tcagcagaag ccagggaaag cccctaaact cctgatctat     540
aaggcctcta gtttagccag tggggcccca tcaaggttca gcggcagtgg atctgggaca     600
gatttcactc tcaccatcag cagcctgcag cctgatgatt ttgcaactta ttactgccaa     660
caatatagta attatccgct cactttcggc ggagggacca agctggagat caaacgt       717
```

<210> SEQ ID NO 12
<211> LENGTH: 762
<212> TYPE: DNA
<213> ORGANISM: Artificial Sequence
<220> FEATURE:
<223> OTHER INFORMATION: DNA encoding A024G01 scFv

<400> SEQUENCE: 12

```
gaggtccagc tggtgcagtc tggggctgag gtgaagaaac ctgggtcctc ggtgaaggtc      60
tcctgcaagg cttctggagg caccctcagt agtgatagta tcacttgggt gcgacaggcc     120
ccaggacaag gacttgagtg ggtgggaggg ttaatccctg cccttggtac agcaaattat     180
gcacagaaat tccagggccg agtcacgatg accgcggaca gatccacggg cacagcctac     240
atggagctga ggagcctgaa atttgacgac acggccgtgt attactgtgc gagagtttcc     300
aggacctcat attacgatgt tttgaccgac aacaaccggt attcatatta catggatgtc     360
tggggcaagg gaaccctggt caccgtctcg agtggaggcg gcggttcagg cggaggtggc     420
tctggcggtg gcggaagtgc acacgttata ctgactcaac cgccctcagt gtccgtgtcc     480
ccaacacaga cagccaccat cacctgctct ggagaccact gggacggaaa atctctttcc     540
tggtatcaac agaagccagg ccagtcccct gtcctggtca tctatgaaga tttcaagcgg     600
ccctcaggga tccctgagcg attctctgcc tccaactctg gtacacagc cactctgacc     660
atcagcggga cccaggcaat ggatgaggct gattattact gtcaggcgtg gacaatcgc      720
gctgtggtat tcggcggagg gaccaagctg accgtcctag gt                        762
```

<210> SEQ ID NO 13
<211> LENGTH: 252
<212> TYPE: PRT
<213> ORGANISM: Artificial Sequence
<220> FEATURE:
<223> OTHER INFORMATION: A019C11 and A020F03 scFv

<400> SEQUENCE: 13

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asp Asn
            20                  25                  30

Tyr Met His Trp Val Arg Gln Ala Pro Gly Gln Gly Leu Glu Trp Met
```

-continued

```
                35                  40                  45
Gly Trp Ile Ser Pro Asn Ser Ser Thr Thr Leu Tyr Ala Gln Lys Phe
     50                  55                  60

Arg Gly Arg Val Thr Leu Thr Arg Asp Thr Ser Val Ser Thr Ala Tyr
 65                  70                  75                  80

Met Glu Leu Ser Gly Leu Asp Ser Asp Thr Ala Leu Tyr Phe Cys
                 85                  90                  95

Ala Arg Gly Gly Arg Leu Ala Gly Ser Thr Val Phe Thr Pro Ala Phe
             100                 105                 110

Glu Tyr Trp Gly Arg Gly Thr Met Val Thr Val Ser Ser Gly Gly Gly
             115                 120                 125

Gly Ser Gly Gly Gly Gly Ser Gly Gly Gly Gly Ser Ala Gln Ala Val
     130                 135                 140

Leu Thr Gln Pro Ser Ser Val Ser Glu Ala Pro Arg Gln Arg Val Thr
145                 150                 155                 160

Ile Ser Cys Ser Gly Ser Ser Asn Ile Gly Asn Asn Ala Val Lys
                 165                 170                 175

Trp Tyr Gln Gln Leu Pro Gly Lys Ala Pro Lys Leu Leu Ile Tyr Tyr
                 180                 185                 190

Asp Asp Leu Leu Pro Ser Gly Val Ser Asp Arg Phe Ser Gly Ser Lys
             195                 200                 205

Ser Gly Thr Ser Ala Ser Leu Ala Ile Ser Gly Leu Gln Ser Glu Asp
     210                 215                 220

Glu Ala Asp Tyr Tyr Cys Ala Ala Trp Asp Asp Ser Leu Asn Gly Tyr
225                 230                 235                 240

Val Phe Gly Thr Gly Thr Lys Val Thr Val Leu Gly
                 245                 250

<210> SEQ ID NO 14
<211> LENGTH: 252
<212> TYPE: PRT
<213> ORGANISM: Artificial Sequence
<220> FEATURE:
<223> OTHER INFORMATION: A013B07 scFv

<400> SEQUENCE: 14

Glu Val Gln Leu Val Gln Ser Gly Ala Glu Val Lys Lys Pro Gly Ala
 1               5                  10                  15

Ser Val Lys Val Ser Cys Lys Thr Ser Gly Tyr Thr Phe Thr Asp Asn
             20                  25                  30

Tyr Met His Trp Val Arg Gln Ala Pro Gly Gln Gly Leu Glu Trp Met
         35                  40                  45

Gly Trp Ile Ser Pro Asn Ser Ser Thr Thr Leu Tyr Ala Gln Lys Phe
     50                  55                  60

Arg Gly Arg Val Thr Leu Thr Arg Asp Thr Ser Val Ser Thr Ala Tyr
 65                  70                  75                  80

Met Glu Leu Ser Gly Leu Asp Ser Asp Thr Ala Leu Tyr Phe Cys
                 85                  90                  95

Ala Arg Gly Gly Arg Leu Ala Gly Ser Thr Val Phe Thr Pro Ala Phe
             100                 105                 110

Glu Tyr Trp Gly Gln Gly Thr Met Val Thr Val Ser Ser Gly Gly Gly
             115                 120                 125

Gly Ser Gly Gly Gly Gly Ser Gly Gly Gly Gly Ser Ala Gln Ser Val
     130                 135                 140

Leu Thr Gln Pro Pro Ser Val Ser Glu Ala Pro Arg Gln Arg Val Thr
```

```
                 145                 150                 155                 160
Ile Ser Cys Ser Gly Ser Ser Asn Ile Gly Ala Asn Ala Val Asn
                165                 170                 175

Trp Tyr Gln Gln Leu Pro Gly Lys Ala Pro Lys Leu Leu Ile Tyr Phe
            180                 185                 190

Asp Asp Leu Leu Pro Ser Gly Val Ser Asp Arg Phe Ser Gly Ser Lys
            195                 200                 205

Ser Gly Thr Ser Ala Ser Leu Ala Ile Ser Gly Leu Gln Ser Glu Asp
            210                 215                 220

Glu Ala Asp Tyr Tyr Cys Ala Ala Trp Asp Asp Ser Leu Asn Gly Val
225                 230                 235                 240

Val Phe Gly Gly Gly Thr Lys Leu Thr Val Leu Gly
                245                 250

<210> SEQ ID NO 15
<211> LENGTH: 245
<212> TYPE: PRT
<213> ORGANISM: Artificial Sequence
<220> FEATURE:
<223> OTHER INFORMATION: A004G02 scFv

<400> SEQUENCE: 15

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Ser Tyr
            20                  25                  30

Gly Ile Arg Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Tyr Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asn Pro Gln Tyr Asp Ala Phe Asp Ile Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Ser Tyr Val Leu Thr Gln Pro Pro Ser Val
    130                 135                 140

Ser Gly Thr Pro Gly Gln Arg Val Thr Val Ser Cys Ser Gly Gly Arg
145                 150                 155                 160

Ser Asn Ile Gly Ser Asn Thr Val Lys Trp Tyr Gln Gln Leu Pro Gly
                165                 170                 175

Thr Ala Pro Lys Leu Leu Ile Tyr Gly Asn Asp Gln Arg Pro Ser Gly
            180                 185                 190

Val Pro Asp Arg Phe Ser Gly Ser Lys Ser Gly Asn Thr Ala Ser Leu
            195                 200                 205

Thr Val Ser Gly Leu Gln Val Glu Asp Glu Ala Asp Tyr Tyr Cys Gln
            210                 215                 220

Ser Tyr Asp Ser Ser Leu Arg Gly Ser Val Phe Gly Gly Gly Thr Lys
225                 230                 235                 240

Leu Thr Val Leu Gly
                245
```

-continued

```
<210> SEQ ID NO 16
<211> LENGTH: 242
<212> TYPE: PRT
<213> ORGANISM: Artificial Sequence
<220> FEATURE:
<223> OTHER INFORMATION: A027A11 scFv

<400> SEQUENCE: 16
```

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Thr Trp Val Arg Gln Ala Pro Gly Gln Gly Leu Glu Trp Met
        35                  40                  45

Gly Asp Ile Ile Pro Val Phe Gly Ile Pro Asn Tyr Ala Gln Met Phe
    50                  55                  60

Gln Asp Arg Val Thr Ile Thr Ala Asp Glu Ser Thr Ser Thr Ala Tyr
65                  70                  75                  80

Leu Glu Leu Asn Ser Leu Gly Ala Glu Asp Thr Ala Val Tyr Tyr Cys
                85                  90                  95

Ala Arg Gly Ser Gln Ala Phe Glu Ile Trp Gly Lys Gly Thr Thr Val
            100                 105                 110

Thr Val Ser Ser Gly Gly Gly Ser Gly Gly Gly Ser Gly Gly
        115                 120                 125

Gly Gly Ser Gln Ser Val Leu Thr Gln Pro Ala Ser Val Ser Gly Ser
    130                 135                 140

Pro Gly Gln Ser Ile Thr Ile Ser Cys Thr Gly Thr Ser Ser Asp Val
145                 150                 155                 160

Gly Gly Tyr Asn Tyr Val Ser Trp Tyr Gln Gln His Pro Gly Lys Ala
                165                 170                 175

Pro Lys Leu Met Ile Tyr Glu Gly Ser Lys Arg Pro Ser Gly Val Ser
            180                 185                 190

Asn Arg Phe Ser Gly Ser Lys Ser Gly Asn Thr Ala Ser Leu Thr Ile
        195                 200                 205

Ser Gly Leu Gln Ala Glu Asp Glu Ala Asp Tyr Tyr Cys Ser Ser Tyr
    210                 215                 220

Thr Thr Arg Ser Thr Arg Val Phe Gly Gly Gly Thr Lys Leu Thr Val
225                 230                 235                 240

Leu Gly

```
<210> SEQ ID NO 17
<211> LENGTH: 248
<212> TYPE: PRT
<213> ORGANISM: Artificial Sequence
<220> FEATURE:
<223> OTHER INFORMATION: A034G03 scFv

<400> SEQUENCE: 17
```

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Asp Thr Pro Asn Tyr Ala Gln Lys Phe
    50                  55                  60

Gln Gly Arg Val Thr Ile Thr Ala Asp Glu Ser Thr Ser Thr Ala Tyr

```
                65                  70                  75                  80
Met Glu Leu Ser Ser Leu Arg Ser Glu Asp Thr Ala Val Tyr Tyr Cys
                        85                  90                  95

Ala Arg Gly Asn Thr Gly Pro Arg Pro Phe Asp Pro Trp Gly Gln Gly
                100                 105                 110

Thr Leu Val Thr Val Ser Ser Gly Gly Gly Ser Gly Gly Gly Gly
                115                 120                 125

Ser Gly Gly Gly Ser Ala Gln Ala Val Leu Thr Gln Pro Ser Ser
        130                 135                 140

Val Ser Gly Ala Pro Gly Gln Arg Val Thr Ile Ser Cys Ser Ala Thr
145                 150                 155                 160

Ser Pro Asn Ile Gly Ala Gly Asp Glu Ile His Trp Tyr Gln Val Ser
                165                 170                 175

Pro Gly Lys Ala Pro Lys Leu Leu Ile Tyr Gly Asp Ile Lys Arg Pro
                180                 185                 190

Ser Gly Val Ser Asp Arg Phe Ser Gly Ser Lys Ser Gly Thr Thr Ala
                195                 200                 205

Ser Leu Ala Ile Thr Gly Leu Arg Pro Glu Asp Glu Ala Asp Tyr Tyr
        210                 215                 220

Cys Gln Ser Tyr Asp Arg Thr Leu Ser Gly Ser Val Val Phe Gly Gly
225                 230                 235                 240

Gly Thr Lys Val Thr Val Leu Gly
                245

<210> SEQ ID NO 18
<211> LENGTH: 249
<212> TYPE: PRT
<213> ORGANISM: Artificial Sequence
<220> FEATURE:
<223> OTHER INFORMATION: A034H05 scFv

<400> SEQUENCE: 18

Glu Val Gln Leu Val Gln Ser Gly Ala Glu Val Lys Lys Pro Gly Ser
1               5                   10                  15

Ser Val Lys Val Ser Cys Lys Val Ser Gly Gly Ser Phe Pro Asn Tyr
                20                  25                  30

Ala Ile Asn Trp Val Arg Gln Ala Pro Gly Gln Gly Leu Glu Trp Met
            35                  40                  45

Gly Ser Leu Val Pro Val Phe Leu Thr Pro Asn Tyr Ala Glu Arg Phe
        50                  55                  60

Gln Asp Arg Val Thr Ile Thr Ala Asp Glu Ser Thr Ser Thr Ala Tyr
65                  70                  75                  80

Met Glu Leu Arg Ser Leu Arg Ser Asp Asp Thr Ala Val Phe Tyr Cys
                        85                  90                  95

Ala Arg Ser Gly Gly Asp Gly Tyr Arg Asp Tyr Gly Met Asp Leu Trp
                100                 105                 110

Gly Arg Gly Thr Leu Val Thr Val Ser Ser Gly Gly Gly Ser Gly
                115                 120                 125

Gly Gly Gly Ser Gly Gly Gly Gly Ser Ala Gln Ser Val Leu Thr Gln
        130                 135                 140

Pro Pro Ser Ala Ser Gly Thr Pro Gly Gln Arg Val Thr Ile Ser Cys
145                 150                 155                 160

Ser Gly Ser Ser Ser Asn Ile Gly Arg Asn Thr Val Asn Trp Phe Gln
                165                 170                 175

Gln Leu Pro Gly Thr Ala Pro Lys Leu Leu Ile Tyr Ser Ser Asn Gln
```

```
                   180                 185                 190
Arg Pro Ser Gly Val Pro Asp Arg Phe Ala Gly Ser Lys Ser Gly Thr
            195                 200                 205

Ser Ala Ser Leu Ala Ile Ser Gly Leu Gln Ser Glu Asp Glu Ala Asp
        210                 215                 220

Tyr Tyr Cys Ala Ala Trp Asp Ser Leu Asn Gly Leu Val Phe Gly
225                 230                 235                 240

Gly Gly Thr Lys Leu Thr Val Leu Gly
                245

<210> SEQ ID NO 19
<211> LENGTH: 248
<212> TYPE: PRT
<213> ORGANISM: Artificial Sequence
<220> FEATURE:
<223> OTHER INFORMATION: A053H04 scFv

<400> SEQUENCE: 19

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Thr Gly Pro Arg Pro Phe Asp Pro Trp Gly Lys Gly
            100                 105                 110

Thr Thr Val Thr Val Ser Ser Gly Gly Gly Gly Ser Gly Gly Gly Gly
        115                 120                 125

Ser Gly Gly Gly Gly Ser Ala Gln Ala Val Leu Thr Gln Pro Ser Ser
    130                 135                 140

Val Ser Gly Ala Pro Gly Gln Arg Val Thr Val Ser Cys Thr Gly Ser
145                 150                 155                 160

Ser Ser Asn Ile Gly Ala Gly Tyr Glu Val Asn Trp Tyr Gln Gln Leu
                165                 170                 175

Pro Gly Thr Ala Pro Lys Leu Leu Ile Tyr Gly Asp Thr Asn Arg Pro
            180                 185                 190

Ser Gly Val Pro Asp Arg Phe Ser Gly Ser Lys Ser Gly Thr Ser Ala
        195                 200                 205

Ser Leu Ala Ile Thr Gly Leu Gln Ala Glu Asp Glu Ala Asn Tyr Tyr
    210                 215                 220

Cys Gln Ser Tyr Asp Ser Gly Pro Gly Pro Val Val Phe Gly Gly
225                 230                 235                 240

Gly Thr Lys Leu Thr Val Leu Gly
                245

<210> SEQ ID NO 20
<211> LENGTH: 250
<212> TYPE: PRT
<213> ORGANISM: Artificial Sequence
<220> FEATURE:
<223> OTHER INFORMATION: A030D09 scFv
```

-continued

<400> SEQUENCE: 20

```
Gln Val Gln Leu Gln Gln Ser Gly Ala Glu Val Lys Lys Pro Gly Ser
1               5                   10                  15
Ser Val Lys Val Ser Cys Lys Thr Ser Gly Gly Ala Phe Ser His Tyr
            20                  25                  30
Ala Ile His Trp Val Arg Leu Ala Pro Gly Gln Gly Leu Glu Trp Met
        35                  40                  45
Gly Asp Ile Ile Pro Val Tyr Gly Ser Thr Thr Tyr Ala Gln Lys Phe
    50                  55                  60
Gln Asp Arg Val Thr Ile Ser Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Trp Tyr Tyr Asp Ile Leu Thr Gly Tyr Trp Asp Tyr Tyr
            100                 105                 110
Tyr Met Asp Val Trp Gly Lys Gly Thr Leu Val Thr Val Ser Ser Gly
        115                 120                 125
Gly Gly Gly Ser Gly Gly Gly Ser Gly Gly Gly Ser Ser Glu
    130                 135                 140
Leu Thr Gln Asp Pro Ala Val Ser Val Ala Leu Gly Gln Thr Val Arg
145                 150                 155                 160
Ile Thr Cys Gln Gly Asp Ser Leu Arg Ser Tyr Tyr Ala Ser Trp Tyr
                165                 170                 175
Gln Gln Lys Pro Gly Gln Ala Pro Val Leu Val Ile Tyr Gly Lys Asn
            180                 185                 190
Asn Arg Pro Ser Gly Ile Pro Asp Arg Phe Ser Gly Ser Ser Ser Gly
        195                 200                 205
Asn Thr Ala Ser Leu Thr Ile Thr Gly Ala Gln Ala Glu Asp Glu Ala
    210                 215                 220
Asp Tyr Tyr Cys Asn Ser Arg Asp Ser Ser Gly Asn His Val Val Phe
225                 230                 235                 240
Gly Gly Gly Thr Lys Leu Thr Val Leu Gly
                245                 250
```

<210> SEQ ID NO 21
<211> LENGTH: 241
<212> TYPE: PRT
<213> ORGANISM: Artificial Sequence
<220> FEATURE:
<223> OTHER INFORMATION: A010D09 scFv

<400> SEQUENCE: 21

```
Gln Val Gln Leu Val Gln Ser Gly Ala Glu Val Lys Lys Leu Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
```

```
Ala Arg Asp Leu Ser Arg Leu Gly Met Asp Val Trp Gly Gln Gly Thr
            100                 105                 110

Thr Val Thr Val Ser Ser Gly Gly Gly Gly Ser Gly Gly Gly Gly Ser
            115                 120                 125

Gly Gly Gly Gly Ser Asp Ile Gln Met Thr Gln Ser Pro Ser Thr Leu
        130                 135                 140

Ser Ala Ser Ile Gly Asp Arg Val Thr Ile Thr Cys Arg Ala Ser Glu
145                 150                 155                 160

Gly Ile Tyr His Trp Leu Ala Trp Tyr Gln Gln Lys Pro Gly Lys Ala
                165                 170                 175

Pro Lys Leu Leu Ile Tyr Lys Ala Ser Ser Leu Ala Ser Gly Ala Pro
            180                 185                 190

Ser Arg Phe Ser Gly Ser Gly Ser Gly Thr Asp Phe Thr Leu Thr Ile
            195                 200                 205

Ser Ser Leu Gln Pro Asp Asp Phe Ala Thr Tyr Tyr Cys Gln Gln Tyr
        210                 215                 220

Ser Asn Tyr Pro Leu Thr Phe Gly Gly Gly Thr Lys Leu Glu Ile Lys
225                 230                 235                 240

Arg

<210> SEQ ID NO 22
<211> LENGTH: 240
<212> TYPE: PRT
<213> ORGANISM: Artificial Sequence
<220> FEATURE:
<223> OTHER INFORMATION: A027B01 scFv

<400> SEQUENCE: 22

Gln Val Gln Leu Leu Gln Ser Ala Ala Glu Val Lys Lys Pro Gly Ser
1               5                   10                  15

Ser Val Lys Val Ser Cys Lys Thr Ser Gly Gly Thr Phe Arg Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ile Ser Ala Gly Met Asp Val Trp Gly Arg Gly Thr Leu
            100                 105                 110

Val Thr Val Ser Ser Gly Gly Gly Gly Ser Gly Gly Gly Gly Ser Gly
            115                 120                 125

Gly Gly Gly Ser Asp Ile Gln Met Thr Gln Ser Pro Ser Phe Leu Ser
        130                 135                 140

Ala Ser Ile Gly Asp Arg Val Thr Ile Thr Cys Arg Ala Ser Glu Gly
145                 150                 155                 160

Ile Tyr His Trp Leu Ala Trp Tyr Gln Gln Lys Pro Gly Lys Ala Pro
                165                 170                 175

Lys Leu Leu Ile Tyr Lys Ala Ser Ser Leu Ala Ser Gly Ala Pro Ser
            180                 185                 190

Arg Phe Ser Gly Ser Gly Ser Gly Thr Asp Phe Thr Leu Thr Ile Ser
            195                 200                 205

Ser Leu Gln Pro Asp Asp Phe Ala Thr Tyr Tyr Cys Gln Gln Tyr Ser
```

```
            210                 215                 220
Asn Tyr Pro Leu Thr Phe Gly Gly Thr Lys Leu Glu Ile Lys Arg
225                 230                 235                 240

<210> SEQ ID NO 23
<211> LENGTH: 239
<212> TYPE: PRT
<213> ORGANISM: Artificial Sequence
<220> FEATURE:
<223> OTHER INFORMATION: A027H08 scFv

<400> SEQUENCE: 23

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Thr Pro Gly Gln Gly Leu Glu Trp Met
        35                  40                  45

Gly Gly Ile Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala His
65                  70                  75                  80

Met Glu Leu Ser Ser Leu Arg Ser Glu Asp Thr Ala Val Tyr Tyr Cys
                85                  90                  95

Ala Arg Gly Ile Ser Gly Gly Met Asp Val Trp Gly Lys Gly Thr Leu
            100                 105                 110

Val Thr Val Ser Ser Gly Gly Gly Ser Gly Gly Gly Ser Gly Gly
        115                 120                 125

Gly Gly Ser Asp Ile Gln Met Thr Gln Ser Pro Ser Thr Leu Ser Ala
    130                 135                 140

Ser Ile Gly Asp Arg Val Thr Ile Thr Cys Arg Ala Ser Glu Gly Ile
145                 150                 155                 160

Tyr His Trp Leu Ala Trp Tyr Gln Gln Lys Pro Gly Lys Ala Pro Lys
                165                 170                 175

Leu Leu Ile Tyr Lys Ala Ser Ser Leu Ala Ser Gly Ala Pro Ser Arg
            180                 185                 190

Phe Ser Gly Ser Gly Ser Gly Thr Asp Phe Thr Leu Thr Ile Ser Ser
        195                 200                 205

Leu Gln Pro Asp Asp Phe Ala Thr Tyr Tyr Cys Gln Gln Tyr Ser Asn
    210                 215                 220

Tyr Pro Leu Thr Phe Gly Gly Gly Thr Lys Leu Glu Ile Lys Arg
225                 230                 235

<210> SEQ ID NO 24
<211> LENGTH: 254
<212> TYPE: PRT
<213> ORGANISM: Artificial Sequence
<220> FEATURE:
<223> OTHER INFORMATION: A024G01 scFv

<400> SEQUENCE: 24

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Ser Asp
            20                  25                  30

Ser Ile Thr Trp Val Arg Gln Ala Pro Gly Gln Gly Leu Glu Trp Val
        35                  40                  45
```

```
Gly Gly Leu Ile Pro Ala Leu Gly Thr Ala Asn Tyr Ala Gln Lys Phe
         50                  55                  60

Gln Gly Arg Val Thr Met Thr Ala Asp Arg Ser Thr Gly Thr Ala Tyr
 65                  70                  75                  80

Met Glu Leu Arg Ser Leu Lys Phe Asp Asp Thr Ala Val Tyr Tyr Cys
                 85                  90                  95

Ala Arg Val Ser Arg Thr Ser Tyr Tyr Asp Val Leu Thr Asp Asn Asn
                100                 105                 110

Arg Tyr Ser Tyr Tyr Met Asp Val Trp Gly Lys Gly Thr Leu Val Thr
                115                 120                 125

Val Ser Ser Gly Gly Gly Ser Gly Gly Gly Ser Gly Gly
        130                 135                 140         Gly

Gly Ser Ala His Val Ile Leu Thr Gln Pro Ser Val Ser Val Ser
145                 150                 155                 160

Pro Thr Gln Thr Ala Thr Ile Thr Cys Ser Gly Asp His Leu Gly Arg
                165                 170                 175

Lys Ser Leu Ser Trp Tyr Gln Lys Pro Gly Gln Ser Pro Val Leu
                180                 185                 190

Val Ile Tyr Glu Asp Phe Lys Arg Pro Ser Gly Ile Pro Glu Arg Phe
            195                 200                 205

Ser Ala Ser Asn Ser Gly Tyr Thr Ala Thr Leu Thr Ile Ser Gly Thr
210                 215                 220

Gln Ala Met Asp Glu Ala Asp Tyr Tyr Cys Gln Ala Trp Asp Asn Arg
225                 230                 235                 240

Ala Val Val Phe Gly Gly Gly Thr Lys Leu Thr Val Leu Gly
                245                 250

<210> SEQ ID NO 25
<211> LENGTH: 16
<212> TYPE: PRT
<213> ORGANISM: Homo Sapiens

<400> SEQUENCE: 25

Gly Gly Arg Leu Ala Gly Ser Thr Val Phe Thr Pro Ala Phe Glu Tyr
1               5                   10                  15

<210> SEQ ID NO 26
<211> LENGTH: 10
<212> TYPE: PRT
<213> ORGANISM: Homo Sapiens

<400> SEQUENCE: 26

Ser Asn Pro Gln Tyr Asp Ala Phe Asp Ile
1               5                   10

<210> SEQ ID NO 27
<211> LENGTH: 7
<212> TYPE: PRT
<213> ORGANISM: Homo Sapiens

<400> SEQUENCE: 27

Gly Ser Gln Ala Phe Glu Ile
1               5

<210> SEQ ID NO 28
<211> LENGTH: 10
<212> TYPE: PRT
<213> ORGANISM: Homo Sapiens

<400> SEQUENCE: 28
```

```
Gly Asn Thr Gly Pro Arg Pro Phe Asp Pro
1               5                   10
```

<210> SEQ ID NO 29
<211> LENGTH: 13
<212> TYPE: PRT
<213> ORGANISM: Homo Sapiens

<400> SEQUENCE: 29

```
Ser Gly Gly Asp Gly Tyr Arg Asp Tyr Gly Met Asp Leu
1               5                   10
```

<210> SEQ ID NO 30
<211> LENGTH: 18
<212> TYPE: PRT
<213> ORGANISM: Homo Sapiens

<400> SEQUENCE: 30

```
Ser Trp Tyr Tyr Asp Ile Leu Thr Gly Tyr Trp Asp Tyr Tyr Tyr Met
1               5                   10                  15

Asp Val
```

<210> SEQ ID NO 31
<211> LENGTH: 9
<212> TYPE: PRT
<213> ORGANISM: Homo Sapiens

<400> SEQUENCE: 31

```
Asp Leu Ser Arg Leu Gly Met Asp Val
1               5
```

<210> SEQ ID NO 32
<211> LENGTH: 8
<212> TYPE: PRT
<213> ORGANISM: Homo Sapiens

<400> SEQUENCE: 32

```
Gly Ile Ser Ala Gly Met Asp Val
1               5
```

<210> SEQ ID NO 33
<211> LENGTH: 8
<212> TYPE: PRT
<213> ORGANISM: Homo Sapiens

<400> SEQUENCE: 33

```
Gly Ile Ser Gly Gly Met Asp Val
1               5
```

<210> SEQ ID NO 34
<211> LENGTH: 22
<212> TYPE: PRT
<213> ORGANISM: Homo Sapiens

<400> SEQUENCE: 34

```
Val Ser Arg Thr Ser Tyr Tyr Asp Val Leu Thr Asp Asn Asn Arg Tyr
1               5                   10                  15

Ser Tyr Tyr Met Asp Val
                20
```

<210> SEQ ID NO 35
<211> LENGTH: 1717
<212> TYPE: DNA

<213> ORGANISM: Homo Sapiens

<400> SEQUENCE: 35

```
acctctgtcc ttagagggga ctggaaccta attctcctga gcctgaggga gggtggaggg      60
tctcaagaca acgctgtccc cacgacggag tgccaggagc actaacagta cccttagatt     120
gctttcctcc tccctccttt tttattttca agttcctttt tatttctcct tgcgtaacaa     180
ccttcttccc ttctgcacca ctgcccgtac ccttacccgc gccgccacct ccttgctaca     240
ccactcttga aaccacagct gttggcaggg tcccccagct catgccagcc tcatctcctt     300
tcttgctagc ccccaaaggg cctccaggca acatggggggg cccagtcaga gagccggcac     360
tctcagttgc cctctggttg agttgggggg cagctctggg ggccgtggct tgtgccatgg     420
ctctgctgac ccaacaaaca gagctgcaga gcctcaggag agaggtgagc cggctgcaga     480
ggacaggagg ccctcccag aatggggaag ggtatccctg gcagagtctc ccggagcaga      540
gttccgatgc cctggaagcc tgggagaatg gggagagatc ccggaaaagg agagcagtgc     600
tcacccaaaa acagaagaag cagcactctg tcctgcacct ggttcccatt aacgccacct     660
ccaaggatga ctccgatgtg acagaggtga tgtggcaacc agctcttagg cgtgggagag     720
gcctacaggc ccaaggatat ggtgtccgaa tccaggatgc tggagtttat ctgctgtata     780
gccaggtcct gtttcaagac gtgactttca ccatgggtca ggtggtgtct cgagaaggcc     840
aaggaaggca ggagactcta ttccgatgta taagaagtat gccctcccac ccggaccggg     900
cctacaacag ctgctatagc gcaggtgtct tccatttaca ccaagggat attctgagtg      960
tcataattcc ccgggcaagg gcgaaactta acctctctcc acatggaacc ttcctggggt    1020
ttgtgaaact gtgattgtgt tataaaaagt ggctcccagc ttggaagacc agggtgggta    1080
catactggag acagccaaga gctgagtata taaaggagag ggaatgtgca ggaacagagg    1140
cgtcttcctg ggtttggctc cccgttcctc acttttccct tttcattccc accccctaga    1200
ctttgatttt acggatatct tgcttctgtt ccccatggag ctccgaattc ttgcgtgtgt    1260
gtagatgagg ggcgggggac gggcgccagg cattgtccag acctggtcgg ggcccactgg    1320
aagcatccag aacagcacca ccatctagcg gccgctctag aggatccctc gagggggccca    1380
agcttacgcg tgcatgcgac gtcatagctc tctccctata gtgagtcgta ttataagcta    1440
gcttgggatc tttgtgaagg aaccttactt ctgtggtgtg acataattgg acaaactacc    1500
tacagagatt taaagctcta aggtaaatat aaaatttta agtgtataat gtgttaaact    1560
agctgcatat gcttgctgct tgagagtttg gcttactgag tatgattatg aaaatattat    1620
acacaggagc tagtgatcta tgttggtttt agatcaagcc aaggtcattc aggcctcagc    1680
tcaagctgtc atgatcatat cagcatacaa ttgtgag                             1717
```

<210> SEQ ID NO 36
<211> LENGTH: 233
<212> TYPE: PRT
<213> ORGANISM: Homo Sapiens

<400> SEQUENCE: 36

```
Met Gly Gly Pro Val Arg Glu Pro Ala Leu Ser Val Ala Leu Trp Leu
1               5                   10                  15
Ser Trp Gly Ala Ala Leu Gly Ala Val Ala Cys Ala Met Ala Leu Leu
            20                  25                  30
Thr Gln Gln Thr Glu Leu Gln Ser Leu Arg Arg Glu Val Ser Arg Leu
        35                  40                  45
```

```
Gln Arg Thr Gly Gly Pro Ser Gln Asn Gly Glu Gly Tyr Pro Trp Gln
 50                  55                  60

Ser Leu Pro Glu Gln Ser Ser Asp Ala Leu Glu Ala Trp Glu Asn Gly
 65                  70                  75                  80

Glu Arg Ser Arg Lys Arg Arg Ala Val Leu Thr Gln Lys Gln Lys Lys
                 85                  90                  95

Gln His Ser Val Leu His Leu Val Pro Ile Asn Ala Thr Ser Lys Asp
            100                 105                 110

Asp Ser Asp Val Thr Glu Val Met Trp Gln Pro Ala Leu Arg Arg Gly
            115                 120                 125

Arg Gly Leu Gln Ala Gln Gly Tyr Gly Val Arg Ile Gln Asp Ala Gly
        130                 135                 140

Val Tyr Leu Leu Tyr Ser Gln Val Leu Phe Gln Asp Val Thr Phe Thr
145                 150                 155                 160

Met Gly Gln Val Val Ser Arg Glu Gly Gln Gly Arg Gln Glu Thr Leu
                165                 170                 175

Phe Arg Cys Ile Arg Ser Met Pro Ser His Pro Asp Arg Ala Tyr Asn
            180                 185                 190

Ser Cys Tyr Ser Ala Gly Val Phe His Leu His Gln Gly Asp Ile Leu
        195                 200                 205

Ser Val Ile Ile Pro Arg Ala Arg Ala Lys Leu Asn Leu Ser Pro His
210                 215                 220

Gly Thr Phe Leu Gly Phe Val Lys Leu
225                 230

<210> SEQ ID NO 37
<211> LENGTH: 250
<212> TYPE: PRT
<213> ORGANISM: Homo Sapiens

<400> SEQUENCE: 37

Met Pro Ala Ser Ser Pro Phe Leu Leu Ala Pro Lys Gly Pro Pro Gly
 1               5                  10                  15

Asn Met Gly Gly Pro Val Arg Glu Pro Ala Leu Ser Val Ala Leu Trp
                20                  25                  30

Leu Ser Trp Gly Ala Ala Leu Gly Ala Val Ala Cys Ala Met Ala Leu
            35                  40                  45

Leu Thr Gln Gln Thr Glu Leu Gln Ser Leu Arg Arg Glu Val Ser Arg
 50                  55                  60

Leu Gln Arg Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                 85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190
```

```
Leu Phe Arg Cys Ile Arg Ser Met Pro Ser His Pro Asp Arg Ala Tyr
            195                 200                 205

Asn Ser Cys Tyr Ser Ala Gly Val Phe His Leu His Gln Gly Asp Ile
        210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
            245                 250

<210> SEQ ID NO 38
<211> LENGTH: 285
<212> TYPE: PRT
<213> ORGANISM: Homo sapiens

<400> SEQUENCE: 38

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 39
<211> LENGTH: 177
<212> TYPE: PRT
```

<213> ORGANISM: Homo sapiens

<400> SEQUENCE: 39

```
Met Cys Leu Ser His Leu Glu Asn Met Pro Leu Ser His Ser Arg Thr
 1               5                  10                  15
Gln Gly Ala Gln Arg Ser Ser Trp Lys Leu Trp Leu Phe Cys Ser Ile
            20                  25                  30
Val Met Leu Leu Phe Leu Cys Ser Phe Ser Trp Leu Ile Phe Ile Phe
        35                  40                  45
Leu Gln Leu Glu Thr Ala Lys Glu Pro Cys Met Ala Lys Phe Gly Pro
 50                  55                  60
Leu Pro Ser Lys Trp Gln Met Ala Ser Ser Glu Pro Pro Cys Val Asn
 65                  70                  75                  80
Lys Val Ser Asp Trp Lys Leu Glu Ile Leu Gln Asn Gly Leu Tyr Leu
                85                  90                  95
Ile Tyr Gly Gln Val Ala Pro Asn Ala Asn Tyr Asn Asp Val Ala Pro
            100                 105                 110
Phe Glu Val Arg Leu Tyr Lys Asn Lys Asp Met Ile Gln Thr Leu Thr
        115                 120                 125
Asn Lys Ser Lys Ile Gln Asn Val Gly Gly Thr Tyr Glu Leu His Val
130                 135                 140
Gly Asp Thr Ile Asp Leu Ile Phe Asn Ser Glu His Gln Val Leu Lys
145                 150                 155                 160
Asn Asn Thr Tyr Trp Gly Ile Ile Leu Leu Ala Asn Pro Gln Phe Ile
                165                 170                 175
Ser
```

<210> SEQ ID NO 40
<211> LENGTH: 251
<212> TYPE: PRT
<213> ORGANISM: Homo sapiens

<400> SEQUENCE: 40

```
Met Ala Glu Asp Leu Gly Leu Ser Phe Gly Glu Thr Ala Ser Val Glu
 1               5                  10                  15
Met Leu Pro Glu His Gly Ser Cys Arg Pro Lys Ala Arg Ser Ser Ser
            20                  25                  30
Ala Arg Trp Ala Leu Thr Cys Cys Leu Val Leu Leu Pro Phe Leu Ala
        35                  40                  45
Gly Leu Thr Thr Tyr Leu Leu Val Ser Gln Leu Arg Ala Gln Gly Glu
 50                  55                  60
Ala Cys Val Gln Phe Gln Ala Leu Lys Gly Gln Glu Phe Ala Pro Ser
 65                  70                  75                  80
His Gln Gln Val Tyr Ala Pro Leu Arg Ala Asp Gly Asp Lys Pro Arg
                85                  90                  95
Ala His Leu Thr Val Val Arg Gln Thr Pro Thr Gln His Phe Lys Asn
            100                 105                 110
Gln Phe Pro Ala Leu His Trp Glu His Glu Leu Gly Leu Ala Phe Thr
        115                 120                 125
Lys Asn Arg Met Asn Tyr Thr Asn Lys Phe Leu Leu Ile Pro Glu Ser
130                 135                 140
Gly Asp Tyr Phe Ile Tyr Ser Gln Val Thr Phe Arg Gly Met Thr Ser
145                 150                 155                 160
Glu Cys Ser Glu Ile Arg Gln Ala Gly Arg Pro Asn Lys Pro Asp Ser
                165                 170                 175
```

```
Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 41
<211> LENGTH: 281
<212> TYPE: PRT
<213> ORGANISM: Homo sapiens

<400> SEQUENCE: 41

Met Ala Met Met Glu Val Gln Gly Gly Pro Ser Leu Gly Gln Thr Cys
 1               5                  10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280
```

<210> SEQ ID NO 42
<211> LENGTH: 233
<212> TYPE: PRT
<213> ORGANISM: Homo sapiens

<400> SEQUENCE: 42

Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
 50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
210                 215                 220

Gln Val Tyr Phe Gly Ile Ile Ala Leu
225                 230

<210> SEQ ID NO 43
<211> LENGTH: 205
<212> TYPE: PRT
<213> ORGANISM: Homo sapiens

<400> SEQUENCE: 43

Met Thr Pro Pro Glu Arg Leu Phe Leu Pro Arg Val Arg Gly Thr Thr
 1               5                  10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
        35                  40                  45

Arg Gln His Pro Lys Met His Leu Ala His Ser Thr Leu Lys Pro Ala
 50                  55                  60

Ala His Leu Ile Gly Asp Pro Ser Lys Gln Asn Ser Leu Leu Trp Arg
 65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln

```
                  100                 105                 110
Val Val Phe Ser Gly Lys Ala Tyr Ser Pro Lys Ala Thr Ser Ser Pro
            115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
                195                 200                 205

<210> SEQ ID NO 44
<211> LENGTH: 281
<212> TYPE: PRT
<213> ORGANISM: Homo sapiens

<400> SEQUENCE: 44

Met Gln Gln Pro Phe Asn Tyr Pro Tyr Pro Gln Ile Tyr Trp Val Asp
  1               5                  10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
            35                  40                  45

Pro Pro Pro Pro Pro Leu Pro Pro Pro Pro Pro Pro Pro Pro Leu Pro
         50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270
```

```
Gln Thr Phe Phe Gly Leu Tyr Lys Leu
        275                 280
```

<210> SEQ ID NO 45
<211> LENGTH: 240
<212> TYPE: PRT
<213> ORGANISM: Homo sapiens

<400> SEQUENCE: 45

```
Met Glu Glu Ser Val Arg Pro Ser Val Phe Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

<210> SEQ ID NO 46
<211> LENGTH: 293
<212> TYPE: PRT
<213> ORGANISM: Homo sapiens

<400> SEQUENCE: 46

```
Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80
```

```
His Leu Leu Arg Asp Cys Ile Ser Cys Ala Ser Ile Cys Gly Gln His
                 85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
        290

<210> SEQ ID NO 47
<211> LENGTH: 184
<212> TYPE: PRT
<213> ORGANISM: Homo sapiens

<400> SEQUENCE: 47

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
        50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160
```

-continued

```
Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 48
<211> LENGTH: 8
<212> TYPE: PRT
<213> ORGANISM: Homo sapiens

<400> SEQUENCE: 48

Asp Tyr Lys Asp Asp Asp Asp Lys
1               5
```